United States Patent
Thomas et al.

(10) Patent No.: US 9,939,389 B2
(45) Date of Patent: Apr. 10, 2018

(54) DATA ACQUISITION SYSTEM USEFUL FOR INSPECTION OF TUBULARS

(71) Applicant: Extreme Hydro Solutions, L.L.C., New Iberia, LA (US)

(72) Inventors: William C. Thomas, Lafayette, LA (US); William J. Thomas, III, New Iberia, LA (US); Perry J. DeCuir, Jr., Rochester Hills, MI (US); Jeffrey R. Wheeler, Winchester, KY (US); Stuart J. Ford, Boise, ID (US)

(73) Assignee: Thomas Engineering Solutions & Consulting, LLC, New Iberia, LA (US)

( * ) Notice: Subject to any disclaimer, the term of this patent is extended or adjusted under 35 U.S.C. 154(b) by 317 days.

(21) Appl. No.: 14/039,448

(22) Filed: Sep. 27, 2013

(65) Prior Publication Data

US 2014/0092234 A1    Apr. 3, 2014

Related U.S. Application Data

(63) Continuation-in-part of application No. 13/832,340, filed on Mar. 15, 2013, now Pat. No. 9,200,490.

(Continued)

(51) Int. Cl.
*H04N 9/47* (2006.01)
*H04N 7/18* (2006.01)
(Continued)

(52) U.S. Cl.
CPC ............. *G01N 21/95* (2013.01); *B08B 1/008* (2013.01); *B08B 1/04* (2013.01); *B08B 9/023* (2013.01);
(Continued)

(58) Field of Classification Search
CPC ...... G01N 21/95; G01N 21/954; B24B 9/002; B24B 29/08; B08B 1/04; B08B 9/0433;
(Continued)

(56) References Cited

U.S. PATENT DOCUMENTS 3,822,429 A    7/1974    Thompson
4,041,773 A    8/1977    Hauldren et al.
(Continued)

FOREIGN PATENT DOCUMENTS

| CN | 200480012199.4 | 2/2009 |
|---|---|---|
| EP | 0131065 A2 | 1/1985 |

(Continued)

OTHER PUBLICATIONS

Technical Industries, Inc., "Vision Array" marketing brochure, publication date unknown.

(Continued)

Primary Examiner — Mohammed Rahaman
Assistant Examiner — Richard A Hansell, Jr.
(74) Attorney, Agent, or Firm — Zeman-Mullen & Ford, LLP

(57) ABSTRACT

A data acquisition system for determining the state of a tubular while the tubular rotates about its cylindrical axis. The tubular remains otherwise substantially stationary. Sensors travel up and down the length of the rotating tubular, interrogating the inside and outside of the tubular for data regarding the tubular's state. Sensors may take samples which may be associated with rotational reference information tying the sample to its absolute position on the internal or external surface of the tubular. A data processor processes the samples and other sensor data to produce a wide array of output, including data signatures of the tubular, maps of contour data regarding the internal or external surface of the tubular, and dimensional data regarding the tubular. Data (Continued)

acquisition is advantageously done in real time, and may further be done concurrently with internal or external cleaning operations.

19 Claims, 30 Drawing Sheets

Related U.S. Application Data

(60) Provisional application No. 61/707,780, filed on Sep. 28, 2012, provisional application No. 61/799,425, filed on Mar. 15, 2013.

(51) Int. Cl.
| | |
|---|---|
| *G01N 21/95* | (2006.01) |
| *B08B 1/00* | (2006.01) |
| *B08B 1/04* | (2006.01) |
| *B08B 9/023* | (2006.01) |
| *B08B 9/043* | (2006.01) |
| *B24B 29/08* | (2006.01) |
| *B24B 9/00* | (2006.01) |
| *G01N 21/954* | (2006.01) |
| *B08B 3/02* | (2006.01) |

(52) U.S. Cl.
CPC .......... *B08B 9/0433* (2013.01); *B08B 9/0436* (2013.01); *B24B 9/002* (2013.01); *B24B 29/08* (2013.01); *B08B 3/024* (2013.01); *G01N 21/954* (2013.01)

(58) Field of Classification Search
CPC ....... B08B 9/023; B08B 9/0436; B08B 1/008; B08B 3/024
USPC ...................................... 348/84, 85
See application file for complete search history.

(56) References Cited

U.S. PATENT DOCUMENTS

| | | | |
|---|---|---|---|
| 4,166,301 A | | 9/1979 | Smith |
| 4,205,407 A | | 6/1980 | King et al. |
| 4,800,104 A | * | 1/1989 | Cruickshank ......... B08B 9/0436 118/306 |
| 4,979,815 A | * | 12/1990 | Tsikos ................. G01B 11/2522 356/2 |
| 5,030,911 A | * | 7/1991 | Lam .................... G01N 27/9013 324/220 |
| 5,060,423 A | | 10/1991 | Klotz |
| 5,362,962 A | * | 11/1994 | Barborak ................ E21B 23/00 250/234 |
| 5,475,890 A | | 12/1995 | Chen |
| 5,947,134 A | | 9/1999 | Kim et al. |
| 5,963,030 A | | 10/1999 | Stark |
| 5,969,255 A | * | 10/1999 | McLean .................. B21C 51/00 73/622 |
| 6,158,074 A | | 12/2000 | Castille |
| 6,290,573 B1 | | 9/2001 | Suzuki |
| 6,425,276 B1 | | 7/2002 | Hirano et al. |
| 6,622,561 B2 | | 9/2003 | Lam et al. |
| 6,919,044 B1 | * | 7/2005 | Shibata .............. G01N 35/0092 422/63 |
| 7,263,887 B2 | | 9/2007 | Sfeir et al. |
| 7,401,518 B2 | | 7/2008 | Sfeir et al. |
| 7,552,640 B2 | | 6/2009 | Sfeir et al. |
| 7,765,632 B2 | | 8/2010 | Lawler et al. |
| 7,935,217 B2 | | 5/2011 | Yashiki et al. |
| 7,997,138 B2 | | 8/2011 | Sfeir et al. |
| 8,165,848 B2 | | 4/2012 | Knight et al. |
| 8,360,668 B1 | | 1/2013 | Hinnant |
| 8,467,049 B2 | * | 6/2013 | Thayer .................... G01B 11/24 356/241.1 |
| 9,062,964 B1 | * | 6/2015 | Arabi ................. G01B 11/0691 |
| 2003/0033881 A1 | * | 2/2003 | Lam .................... G01N 29/0609 73/627 |
| 2003/0198374 A1 | * | 10/2003 | Hagene ................ G01N 21/954 382/141 |
| 2004/0235391 A1 | | 11/2004 | Grivna |
| 2005/0235442 A1 | | 10/2005 | Molter |
| 2006/0066847 A1 | * | 3/2006 | Penza ................ G01N 21/8806 356/241.1 |
| 2006/0288756 A1 | * | 12/2006 | De Meurechy ...... G01N 17/006 73/1.01 |
| 2008/0021662 A1 | * | 1/2008 | Hinn ..................... G01M 3/005 702/34 |
| 2008/0142050 A1 | | 6/2008 | Hashish et al. |
| 2009/0114019 A1 | * | 5/2009 | Fatemi ................... G01B 17/08 73/587 |
| 2009/0217954 A1 | | 9/2009 | Hall |
| 2010/0180915 A1 | | 7/2010 | Patel et al. |
| 2011/0074332 A1 | | 3/2011 | Baker |
| 2011/0220151 A1 | | 9/2011 | Swinford |
| 2012/0006352 A1 | | 1/2012 | Holappa et al. |
| 2012/0028554 A1 | | 2/2012 | Weinberger et al. |
| 2012/0074110 A1 | | 3/2012 | Zediker et al. |
| 2013/0176418 A1 | * | 7/2013 | Pandey ..................... H04N 5/33 348/83 |
| 2013/0298950 A1 | | 11/2013 | Hann |

FOREIGN PATENT DOCUMENTS

| | | |
|---|---|---|
| WO | 2009-105898 A1 | 9/2009 |
| WO | 2009/105899 A1 | 9/2009 |

OTHER PUBLICATIONS

English version of claims from Chinese Patent No. 200480012199.4.

Decuir, Perry J., "Optimizing Hydraulic Presses Using Data Acquisition Systems", proposed IFPE Paper, actual publication date unknown but prior to Feb. 1, 2012.

International Search Report and the Written Opinion of the International Searching Authority in PCT/US2013/062778 dated Jan. 20, 2014 (8 pages).

DMW Industries marketing video. This reference may be seen at http://www.youtube.com/watch?v=k1T018nIVxw. The stated date of publication on YouTube is Sep. 11, 2012.

Aqua Energy marketing video. This reference may be seen at http://www.youtube.com/watch?v=0cplrXczdos. The stated date of publication on YouTube is Jul. 30, 2010.

\* cited by examiner

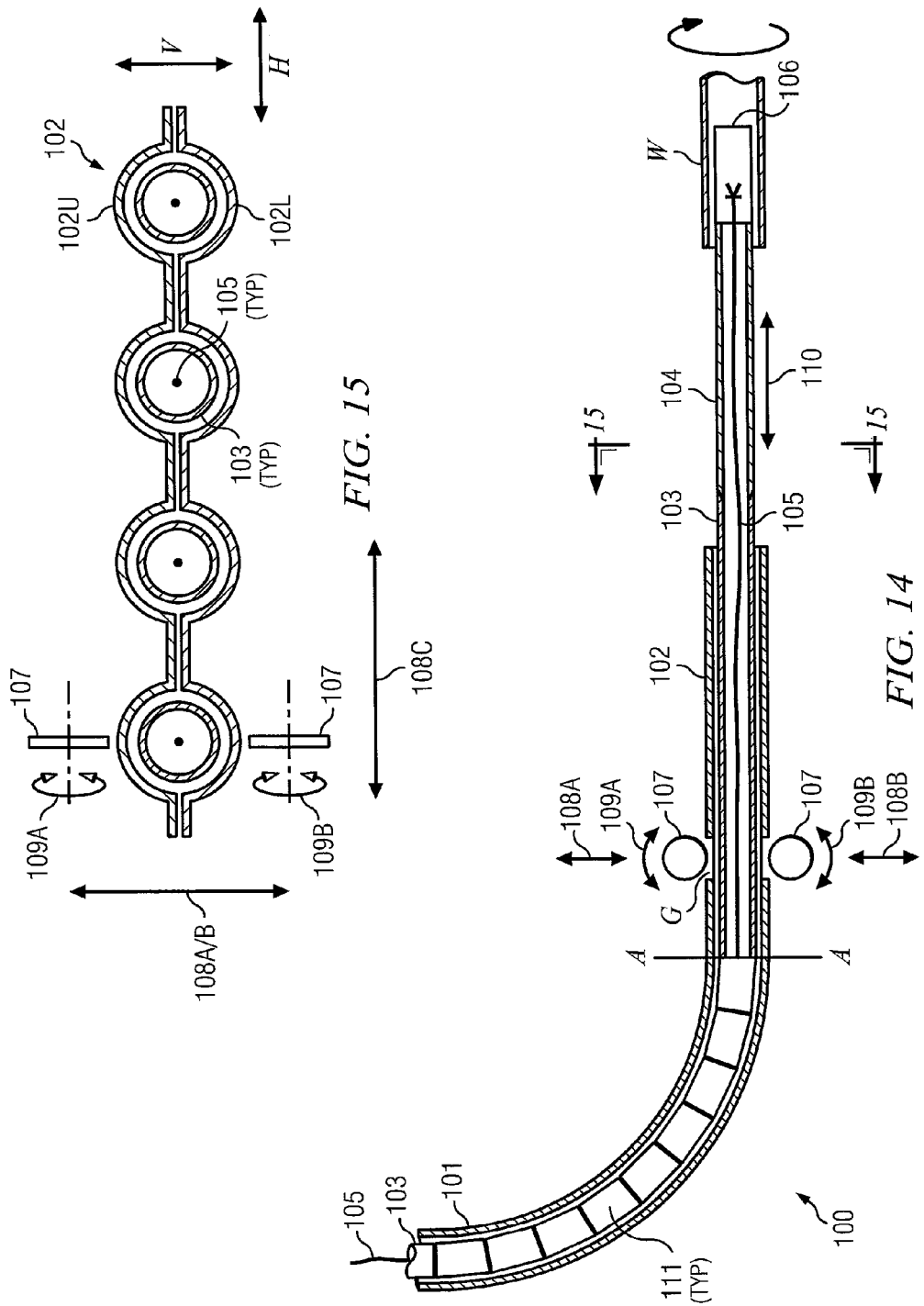

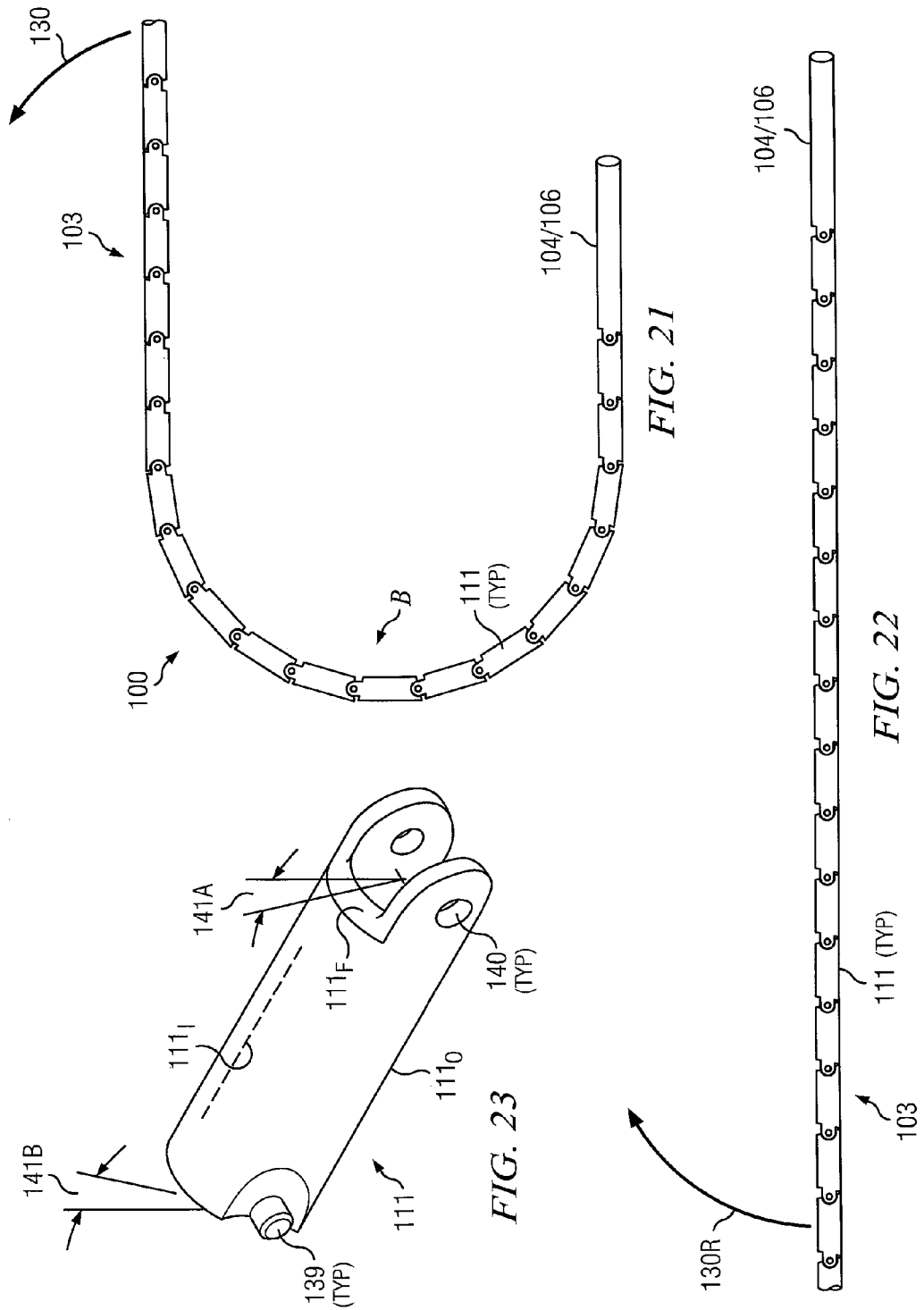

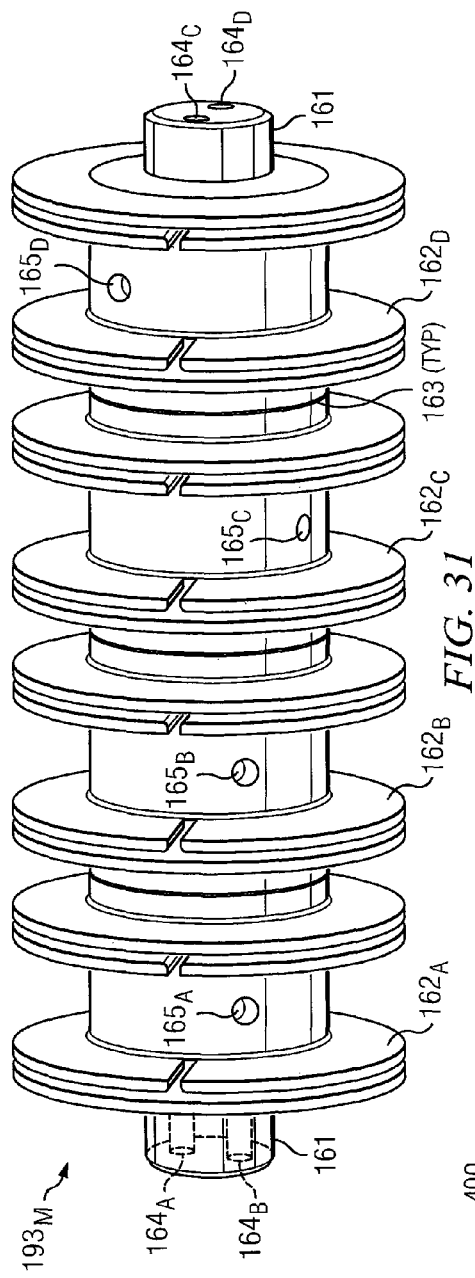
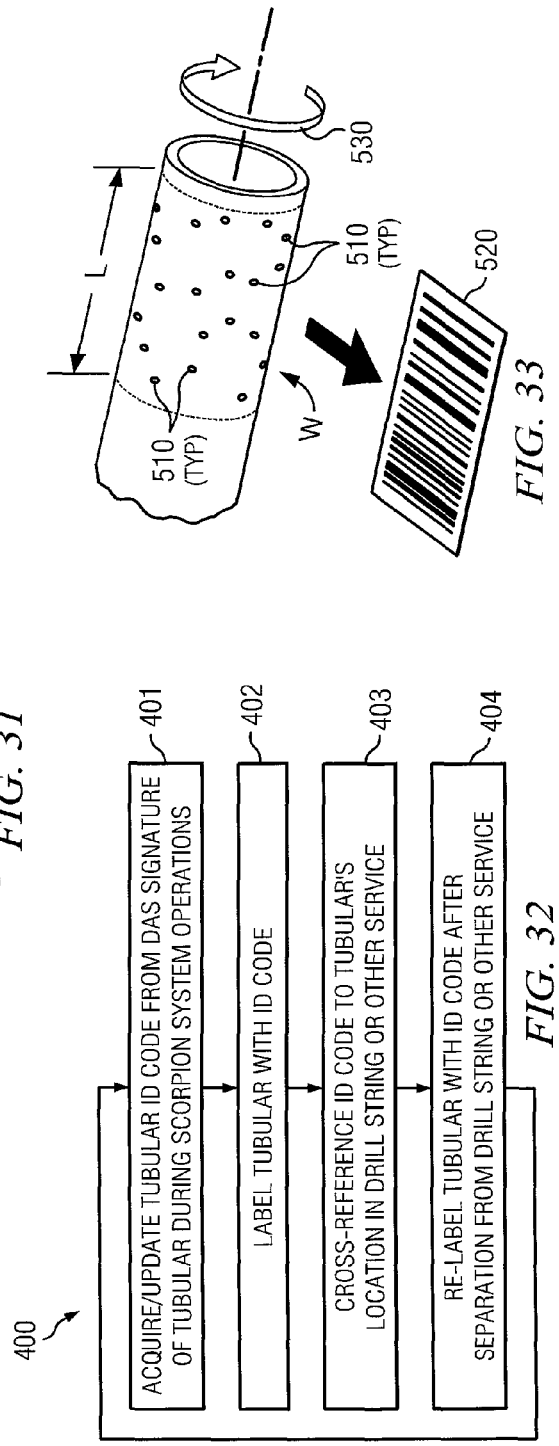
FIG. 31
FIG. 32
FIG. 33

DATA ACQUISITION SYSTEM USEFUL FOR INSPECTION OF TUBULARS

RELATED APPLICATIONS

This application claims the benefit of, and priority to, the following two (2) commonly-assigned U.S. Provisional Applications: (1) Ser. No. 61/707,780, filed Sep. 28, 2012, and (2) Ser. No. 61/799,425, filed Mar. 15, 2013.

This application is also a continuation-in-part of commonly-assigned U.S. Utility application Ser. No. 13/832,340, filed Mar. 15, 2013.

This application incorporates herein by reference the disclosures of the foregoing three applications in their entirety.

FIELD OF THE INVENTION

This disclosure is directed generally to technology useful in tubular cleaning and inspection operations in the oil and gas exploration field, and more specifically to cleaning and inspecting the external and internal surfaces of tubulars such as drill pipe, workstring tubulars, and production tubulars.

BACKGROUND

Throughout this disclosure, the term "Scorpion" or "Scorpion System" refers generally to the disclosed Thomas Services Scorpion brand proprietary tubular management system as a whole.

One drawback of conventional tubular cleaning apparatus is that, with the cleaning apparatus stationary and the tubular drawn longitudinally across, the apparatus requires a large building. Range 3 drilling pipe is typically 40-47 feet long per joint, which means that in order to clean range 3 pipe, the building needs to be at least approximately 120 feet long A further drawback of the prior art is that external cleaning operations are generally completely separate operations from inspection or other data gathering operations regarding the tubular.

Yet another drawback of the prior art is that when ultrasonic sensing alone is used, an intermediate fluid, or water coupling, is often required between the tubular and the ultrasonic sensor. Still further, surface anomalies such as pits and cracks may go undetected. Additionally, a zero degree reference line may need to be drawn on the external surface of the tubular prior to ultrasonic measurement.

SUMMARY

Aspects of the Scorpion System disclosed and claimed in this disclosure address some of the above-described drawbacks of the prior art. In preferred embodiments, the Scorpion System rotates the tubular to be cleaned (hereafter, also called the "Work" in this disclosure) while keeping the Work stationary with respect to the cleaning apparatus. The Scorpion then moves the cleaning apparatus up and down the length of the Work while the Work rotates.

In currently preferred embodiments, the Work is typically rotated at speeds in a range of about 100-300 rpm, and potentially within a range of between about 0.01 rpm and about 1,750 rpm under certain criteria. However, nothing in this disclosure should be interpreted to limit the Scorpion System to any particular rotational speed of the Work. Currently preferred embodiments of the Scorpion System further draw the cleaning apparatus up and down the length of the Work at speeds within a range of about 0.001 linear inches per second and about and 10.0 linear feet per second, depending on the selected corresponding rotational speed for the Work. Again, nothing in this disclosure should be interpreted to limit the Scorpion System to any particular speed at which the cleaning apparatus may move up or down the length of the Work.

The Scorpion System as described in this disclosure is designed to achieve the following operational goals and advantages:

Versatility.

The Scorpion System as disclosed herein is described with respect to currently preferred embodiments. However, as will be noted repeatedly in this disclosure, such currently preferred embodiments are exemplary only, and many of the features, aspects and capabilities of the Scorpion System are customizable to user requirements. As a result the Scorpion System is operable on many diameters of tubular in numerous alternative configurations. Some embodiments may be deployed onto a U.S. Department of Transport standard semi-trailer for mobile service.

Substantially Lower Footprint of Cleaning Apparatus.

As noted above, conventionally, the cleaning of range 3 drill pipe requires a building at least 120 feet long. Certain configurations of the Scorpion System can, for example, clean range 3 pipe in a building of about half that length. Similar footprint savings are available for rig site deployments. As also noted above, a mobile embodiment of the Scorpion System is designed within U.S. Department of Transportation regulations to be mounted on an 18-wheel tractor-trailer unit and be transported on public roads in everyday fashion, without requirements for any special permits.

Dramatically Increased Production Rate in Cleaning.

An operational goal of the Scorpion System is to substantially reduce conventional cleaning time. Further, the integrated yet independently-controllable design of each phase of cleaning operations allows a very small operator staff (one person, if need be) to clean numerous tubulars consecutively in one session, with no other operator involvement needed unless parameters such as tubular size or cleaning requirements change. It will be further understood that in order to optimize productivity, consistency, safety and quality throughout all tubular operations, the systems enabling each phase or aspect of such operations are designed to run independently, and each in independently-selectable modes of automatic, semi-automatic or manual operation. When operator intervention is required, all adjustments to change, for example, modes of operation or tubular size being cleaned, such adjustments are advantageously enabled by hydraulically-powered actuators controlled by system software.

Improved Quality of Clean.

It is anticipated that the Scorpion System will open up the pores of the metal tubular much better than in conventional cleaning, allowing for a more thorough clean. In addition, the high rotational speed of the tubular during cleaning operations allows for a thorough clean without a spiral effect even though cleaning may optionally be done in one pass.

The Scorpion System provides an outer delivery system (ODS) to clean and inspect the external surface of the Work. The ODS generally comprises a "buggy"-like device that travels back and forth above the Work while the Work rotates beneath. Embodiments of the ODS are disclosed in which the buggy travels on a track. The buggy carries structure for performing operations on the external surface of the Work as the buggy travels above the Work. Such structure includes jets for delivery of fluids such as, for example, steam, fluid-borne abrasives, high and low pressure water, compressed air and drying gas (e.g. nitrogen). Such structure further includes brushes and other abrasives for abrasive cleaning or buffing. Such structure further includes data acquisition structure for inspecting and measuring the tubular, such as, for example, lasers, optical cameras, sensors and probes.

It is therefore a technical advantage of the disclosed ODS to clean the exterior of pipe and other tubulars efficiently and effectively. By passing different types of interchangeable cleaning apparatus on a track-mounted assembly over a stationary but rotating tubular, considerable improvement is available for speed and quality of external cleaning of the tubular over conventional methods and structure.

A further technical advantage of the disclosed ODS is to reduce the footprint required for industrial tubular cleaning. By moving cleaning apparatus over of a stationary but rotating tubular, reduced footprint size is available over conventional cleaning systems that move a tubular over stationary cleaning apparatus. Some embodiments of the ODS may be deployed on mobile cleaning systems.

A further technical advantage of the disclosed ODS is to enhance the scope, quality and reliability of inspection of the exterior of the tubular before, during or after cleaning operations. Data acquisition structure such as sensors, probes and lasers may be deployed on the track-mounted assembly passing over the stationary but rotating tubular. Such data acquisition structure may scan or nondestructively examine the exterior of the tubular, either while the tubular is rotating, and/or while the exterior is being cleaned, or otherwise.

A further technical advantage of the disclosed ODS is to reduce the incidence of damage to tubulars during brushing or other abrasive contact operations. Stresses occur when brushing structure passes over a rotating tubular where the tubular's local contour or diameter is greater than nominal. The disclosed ODS provides brushing structure configured to adapt to local variations in contour and diameter of the tubular, including suspending brushes on springs in user-controllable spring equilibrium above the tubular. The brushing pressure for a nominal tubular diameter may be set, per user selection, and the spring suspensions then enable the brushing structure to adapt to local variations in contour and diameter of the tubular. The disclosed ODS also provides other contour-adapting structure such as an articulated drive shaft for a train of brushes, and a swiveling brush including an oblate spheroid-shaped brush profile.

A further technical advantage of the disclosed ODS is to reduce the incidence of areas or features on the external surface of the rotating tubular that may be "missed" by brushing structure as it passes by. Local variations in contour or diameter of the tubular, or sag or bow of the tubular, may cause areas of the tubular's external surface to lose brushing contact (or lose the desired brushing pressure). The features described in the immediately preceding paragraph for brush structure to adapt to local variations in the tubular's contour or diameter are also useful for causing brushing structure to maintain contact (or pressure) with the external surface of the tubular when the external surface momentarily "moves away" from the brushing structure.

A further technical advantage of the disclosed ODS is to maintain an optimal distance between fluid jets operating on the tubular and the external surface of the tubular. Fluid jets are provided on the ODS in order deliver fluids (in liquid or gaseous state) for cleaning and other operational purposes. An electronic control system gathers real time data regarding the local contours in the tubular's external surface and maintains an optimal distance between the fluid jets and the external surface, so that the operating effectiveness of the fluid jets is maximized without causing damage to the tubular's surface.

The Scorpion System further provides a multi-lance injector assembly (MLI) to clean and inspect the internal surface of the Work. The MLI provides a series of extendable and retractable lances that move up and down the internal surface of the Work as it rotates. Each lance provides tool hardware to perform a desired lance function. Examples of lance functions may include, individually or in combinations thereof, and without limitation: hydroblasting, steam cleaning, washing and rinsing, high and low volume compressed air blowing, gas drying (such as nitrogen drying), rattling head cutters, abrasive cleaning, brushing, API drift checking, sensor or other data acquisition (including visual video inspection, thermal imaging, acoustic examination, magnetic resistivity examination and electromagnetic flux examination). Data acquisition may be in the form of static or streaming data acquisition. Lances may have amplifiers on board to boost sensed or generated signals. The MLI enables extension and retraction of individual lances, one at a time, in and out of the Work. The MLI further enables a user-selected sequence of internal surface cleaning and related operations by moving different lances, according to the sequence, into and out of position for extension and retraction in and out of the Work.

Tool hardware on any particular lance may provide for single or shared operations on the lance. For example, in some exemplary embodiments, data acquisition regarding the condition of the internal surface of the Work may be via sensors provided on tool hardware shared with cleaning operations. In other embodiments, the MLI may provide a lance dedicated to data acquisition.

Similarly, in some exemplary embodiments, API drift checking may be advantageously combined with other operations on a single lance. Running an API-standard drift on a lance in and out of the Work is useful not only, to check for dimensional compliance of the Work with API standards, but also to locate and hold other operational tool hardware in a desired position relative to the Work as the lance extends and retracts. Especially on larger diameter Work, it may be advantageous (although not required within the scope of this disclosure) to attach a drift-like assembly to other lance tooling in order to accomplish several advantages. A drift or drift-like assembly: (1) protects more fragile internal parts of the lance and drift mechanisms; (2) minimizes friction, especially in view of the rotational speed of the Work; and (3) keeps the lance stabilized and positioned correctly inside the Work.

In a currently preferred embodiment, the MLI provides four (4) separate lances for internal surface cleaning and related operations. Nothing in this disclosure, however, should be interpreted to limit the MLI to any particular number of lances. In the currently preferred embodiment, the four lances are provided with tooling to accomplish the following exemplary operations:

Lance 1: High pressure water blast for concrete removal and general hydroblasting operations, or steam cleaning, especially on severely rusted or scaled interior surfaces of the Work.

Lance 2: Low pressure/high temperature wash, for general tubular cleaning operations, including salt wash and rust inhibitor coating.

Lance 3: Steel Wire Brushes and/or rattling/cutter head abrasive treatment.

Lance 4: Data probes, sensors, thermal imaging devices or specialized still/video camera probes.

Referring to Lance 3 in more detail, rotating steel wire brushes and/or steel rattling heads are provided for further internal surface cleaning after high pressure and/or low pressure washing phases. In another embodiment, data sensors may be deployed instead to share Lance 2 with the above described low pressure/hot wash function. In another alternative embodiment, high or low volume compressed air or nitrogen may be deployed to Lance 3 for drying and/or expelling debris. The compressed air may also supply pneumatic tools deployed on the lance.

Yet further alternative embodiments may deploy a variety of inspection hardware on various of the lances. For example, acoustic sensors may be deployed for sonic inspection. Magnetic resistivity sensors and magnetic flux sensors (such as a hall effect sensor) may be deployed for magnetic flux inspection. Amplifiers may be deployed to boost signals.

The range of inspection options envisioned in various embodiments of the MLI is varied. For example, visual inspection via video or still cameras may identify and analyze lodged objects in the wall of the Work in real time. Geometry and circularity of the Work may be measured and tagged in real time. Visual inspection video or still cameras may also be used to examine areas of interest on the internal wall of the Work more closely. Such areas of interest may be identified and tagged by visual examination, or by other examination (earlier or at the same time) by, for example, thermal, imaging, acoustic analysis or magnetic flux/resistivity analysis. Such areas of interest may include loss in tubular wall thickness, or other conditions such as pitting, cracking, porosity and other tubular wall damage.

It will be further appreciated that inspection and examination data acquired during MLI operations may also be coordinated (either in real time or later) with other data acquired regarding the Work at any other time. In particular, without limitation, inspection and examination data may be, for example, (1) coordinated with earlier data regarding the Work to provide a history on the Work, or (2) coordinated in real time with comparable data obtained concurrently regarding the exterior surface of the Work to provide a yet more detailed and high resolution analysis of the state of the Work. The scope of this disclosure is not limited in this regard.

Again, nothing in this disclosure should be interpreted to limit the MLI lances to be assigned any specific tooling to perform any specific operations. Any lance may perform any operation(s) per user selection, and may deploy any tooling suitable to perform such user-selected operation(s).

In currently preferred embodiments of the Scorpion System, the lances provided by the MLI are not self-propelling up and down within the interior of the Work. The lances are moved up and down the interior of the Work as further described in this disclosure. However, nothing in this disclosure should be interpreted to limit the lances to a non-self-propelling embodiment. Other embodiments within the scope of this disclosure may have full or partial lance propulsion functionality, including propulsion apparatus that gains traction on the interior surface of the Work.

It is therefore a technical advantage of the disclosed MLI to clean the interior of pipe efficiently and effectively. By extending and retracting interchangeable tooling on multiple lances into and out of a stationary but rotating tubular, considerable improvement is available for speed and quality of internal cleaning of the tubular over conventional methods and structure.

A further technical advantage of the disclosed MLI is to reduce the footprint required for industrial tubular cleaning. By extending and retracting lances into and out of a stationary tubular, reduced footprint size is available over conventional cleaning systems that move a tubular over stationary cleaning apparatus. Some embodiments of the MLI may be deployed on mobile cleaning systems.

A further technical advantage of the disclosed MLI is to enhance the scope, quality and reliability of inspection of the interior of the tubular before, during or after cleaning operations. Data acquisition structure may be deployed on one or more of the extendable or retractable lances. Such data acquisition structure may scan or nondestructively examine the interior of the tubular, either while the tubular is rotating or otherwise. Such data acquisition structure may include sensors, specialized visual inspection probes (such as video cameras), and/or thermal imaging probes.

The foregoing has outlined rather broadly some of the features and technical advantages of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should be also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIG. 14 is a functional cross-section view of aspects of one embodiment of the MLI;

FIG. 15 is a cross-section view as shown on FIG. 14;

FIGS. 21, 22, 23 and 24 illustrate aspects and features of embodiments of KJL assemblies 103;

FIG. 31 is an isometric view of aspects of an embodiment of MLR axle assembly $193_M$;

FIG. 32 is a flow chart illustrating one embodiment of a "tubular tracking" method; and FIG. 33 is a functional diagram illustrating a "rotational bar code".

DETAILED DESCRIPTION

External Cleaning Sand Inspection

FIGS. 1 through 4 illustrate a first embodiment of an ODS assembly (or "buggy"), designated generally on FIGS. 1 through 4 as ODS assembly 201. FIGS. 5 through 13B illustrate a second embodiment of an ODS assembly, designated generally on FIGS. 5 through 13B as ODS assembly 220. Nothing in this disclosure should be interpreted to limit the ODS to the embodiments of ODS assemblies 201 and 220 or the structural features and aspects disclosed thereon.

Figure 1:
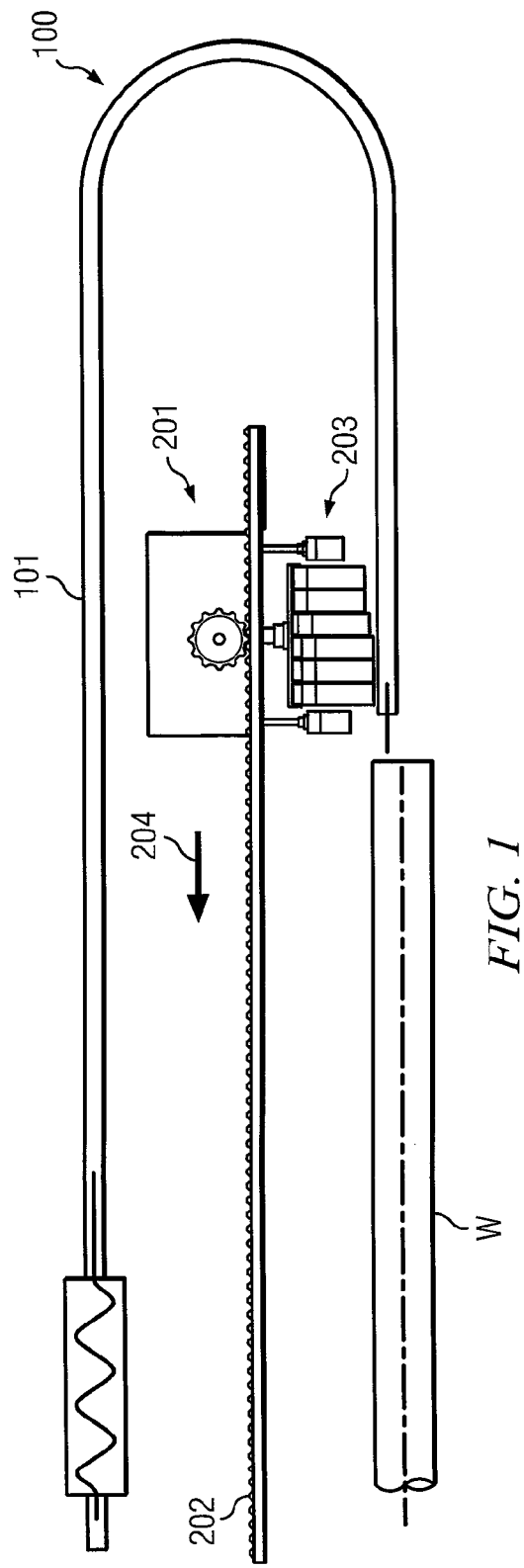
FIG. 1 is a functional-level general arrangement of one embodiment of the ODS in a combination deployment with an MLI 100.

FIG. 1 is a general arrangement drawing that illustrates, in an elevation view, an exemplary embodiment in which the ODS assembly 201 is disposed above tubular W (the Work). It will be seen and understood on FIG. 1 that ODS assembly 201 travels along track 202 while tubular W rotates. As will be described in greater detail further on, ODS assembly 201 provides a plurality of shrouded heads 203 comprising tooling that may perform a user-selected sequence of operations (including cleaning and data acquisition operations) on tubular W. As ODS assembly 201 travels along track 202 while tubular W rotates, it will be seen from FIG. 1 that ODS assembly 201 enables such user-selected sequence of operations by providing heads and associated tooling in a corresponding sequence as ODS assembly 201 comes to bear upon tubular W.

The exemplary embodiment illustrated in FIG. 1 also shows, solely for reference purposes, guide tubes 101 from a Multi-Lance Injector (MLI) assembly 100 in "curved tube" mode, as is fully described in greater detail later on in this disclosure, with reference to "Internal Cleaning and Inspection". In this way, FIG. 1 illustrates an embodiment of the Scorpion System, in which both MLI structure and ODS structure are provided together in one machine. It will be appreciated however, that nothing in this disclosure should be interpreted to require that MLI structure be combined with ODS structure in one machine. Other embodiments, not illustrated or described in this disclosure in any detail, may provide MLI structure and/or ODS structure in stand-alone machines Referring again to FIG. 1, it will be understood that certain conventional structure has been omitted for clarity. For example, ODS assembly 201, track 202 and guide tubes 101, for example, are advantageously supported by structural steel and other conventional support means (including, in some embodiments, a gantry for maintenance access), all of which has been omitted for clarity. Operation of the ODS is advantageously accomplished using conventional hydraulic, pneumatic or electrical apparatus (including geared drive motor apparatus to cause ODS assembly 201 to travel track 202 as illustrated by arrow 204 on FIG. 1), all of which has been also omitted for clarity.

Figure 2:
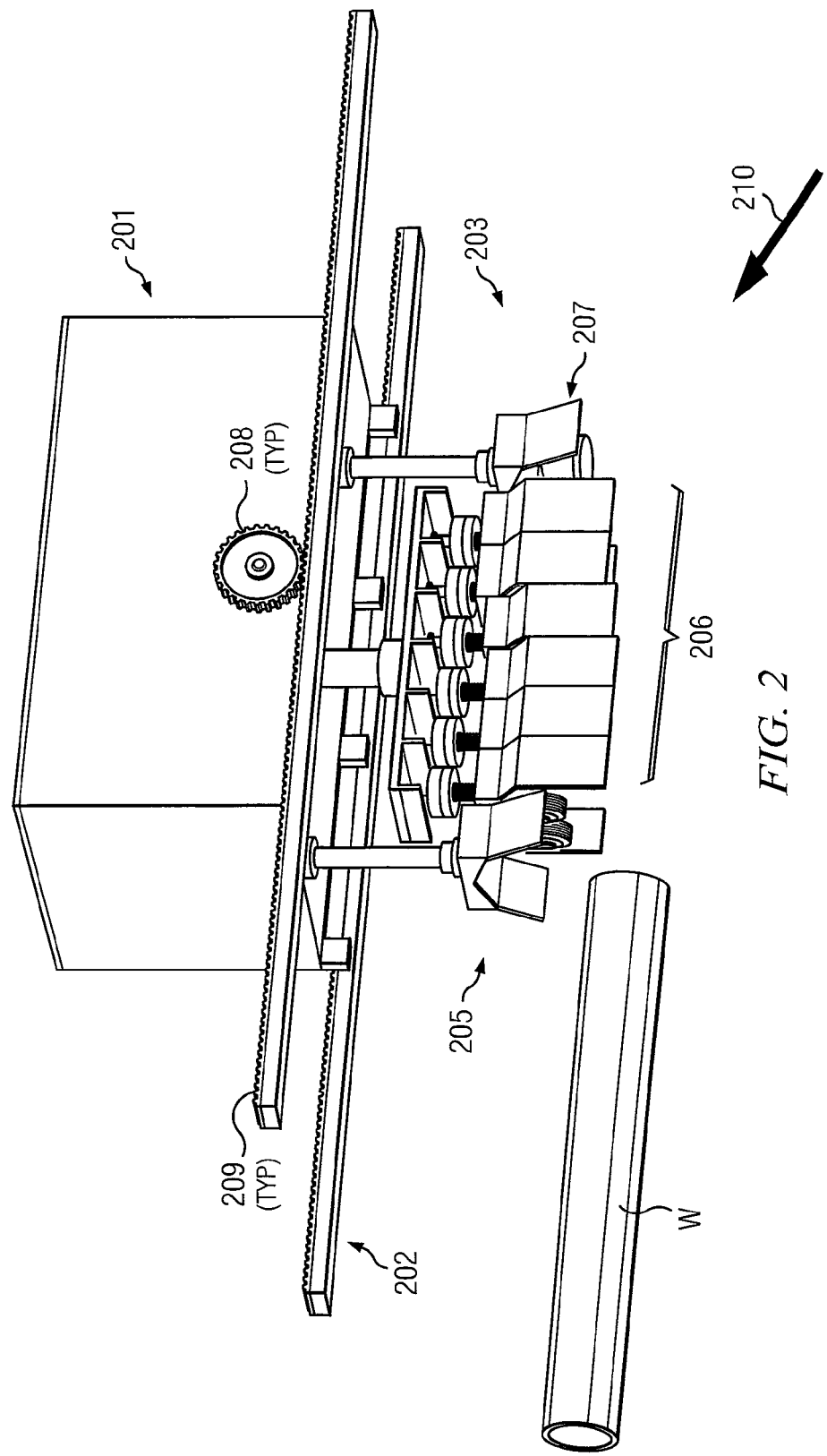
FIG. 2 is an enlargement of FIG. 1 in isometric view.

Turning now to FIG. 2, an embodiment of ODS assembly 201 is illustrated in more detail. It will be appreciated that FIG. 2 is a perspective view of the embodiment shown on FIG. 1, looking back at ODS assembly 201 from tubular W, slightly from underneath. The embodiment of FIG. 2 illustrates ODS assembly 201 operable to move up and back along track 202 via motorized gear wheels 208 on either side of ODS assembly 201 (only one side's gear wheel 208 visible on FIG. 2), whereby motorized gear wheels 208 run in geared rails 209 deployed on track 202. It will be understood, however, that the motorized gear propulsion mechanism for ODS assembly 201 illustrated on FIG. 2 is exemplary only, and any other operable propulsion mechanism for ODS assembly 201 is within the scope of this disclosure.

FIG. 2 also depicts shrouded heads 203 in more detail. Each of shrouded heads 203 comprises tooling surrounded by a shroud. A primary purpose of the shroud is to prevent by-products from the operation of the tooling (e.g. steam, water, dirt and rust removed from the outside of tubular W) from dispersing excessively into the airspace surrounding ODS assembly 201.

The tooling included in shrouded heads 203 is user-selectable according to operational needs. In the exemplary embodiment illustrated in FIG. 2, shrouded heads 203 comprise nozzle head 205, then six abrasive heads 206, and then probe head 207. Nothing in this disclosure should be interpreted, however, to limit the ODS to any particular type or amount of tooling, or the number of shrouded heads on which it is embodied, or the sequence in which it is brought to bear on tubular W.

Figure 3:
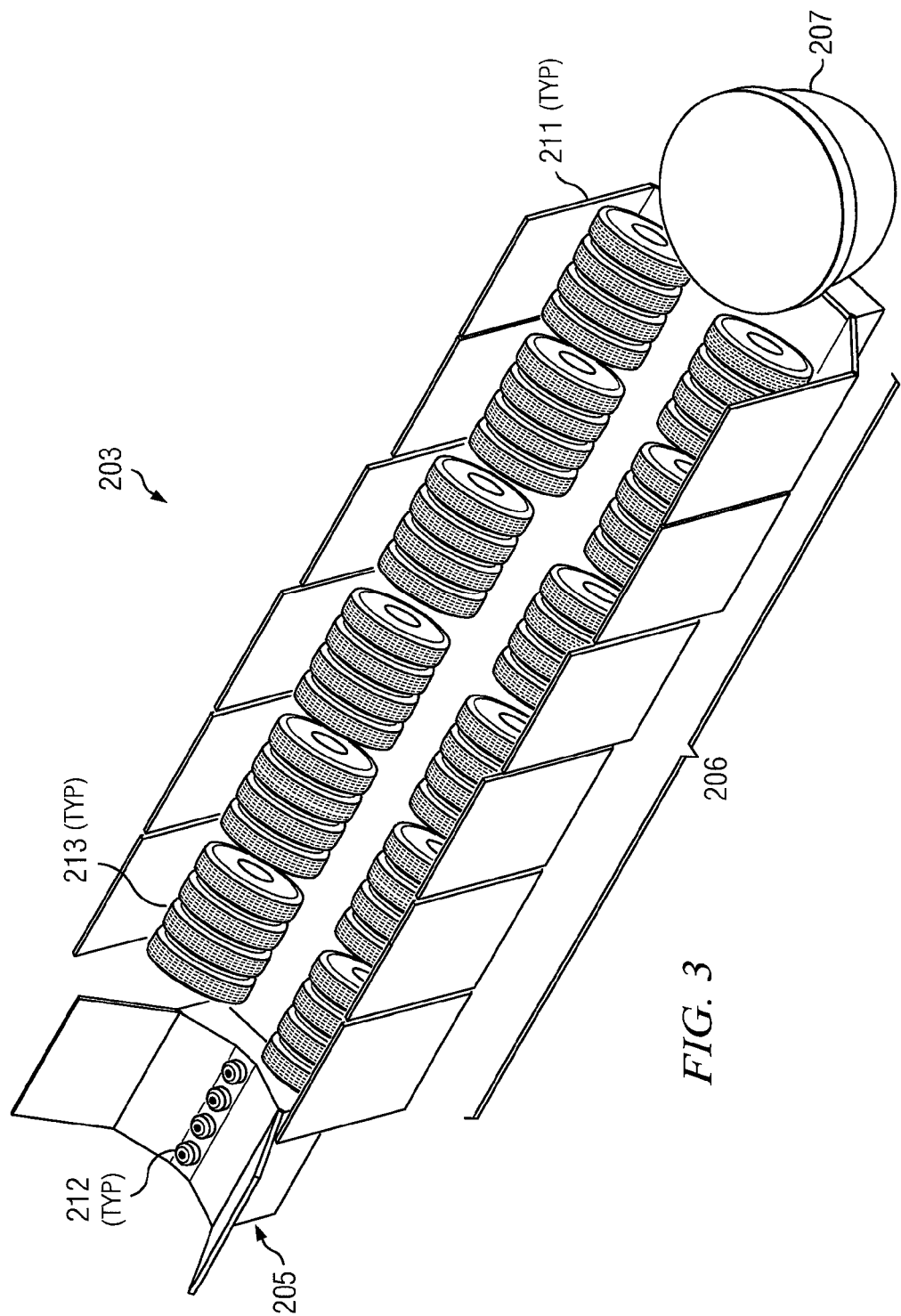
FIG. 3 depicts the underside of one embodiment of the ODS from the view of arrow 210 on FIG. 2.

Reference is now made to FIG. 3, which illustrates the tooling in the exemplary embodiment of FIG. 2 in more detail. FIG. 3 depicts shrouded heads 203 as also shown on FIGS. 1 and 2 from underneath, in the direction of arrow 210 as shown on FIG. 2. Nozzle head 205, abrasive heads 206 and probe head 207 may be seen on FIG. 3, as also seen on FIG. 2. FIG. 3 also depicts each shrouded head 203 comprising tooling surrounded by a shroud (the shrouds labeled reference numeral 211 on FIG. 3).

Referring back briefly to FIGS. 1 and 2 together, it will be seen that when ODS assembly 201 begins its travel in the direction of arrow 204 on FIG. 1 and comes to bear on tubular W, the currently preferred embodiment of the ODS provides nozzle head 205 as the first of shrouded heads 203 to operate on tubular W. Abrasive heads 206 follow nozzle head 205, and probe head 207 follows abrasive heads 206. This exemplary user-selected sequence of shroud heads 203 reflects the following sequence of tubular cleaning and data acquisition operations (although nothing herein should be construed to limit the ODS to the following operational sequence):

Nozzle Head 205—First Nozzle Group:

High pressure water blast (nominally at about 20,000 psi but not limited to any such pressure) for concrete removal and general hydroblasting operations, especially if tubular W has a severely rusted or scaled outer surface.

Nozzle Head 205—Second Nozzle Group:

Low pressure/high temperature wash, nominally at 3,000 psi/300 deg F. but not limited to any such pressure or temperature), for general tubular cleaning operations, including salt wash and rust inhibitor coating.

Abrasive Heads 206:

Abrasive surface cleaning and treatment of outer surface of tubular W via steel wire brush and/or flap wheels for removal, for example, of protruding steel burrs on the outer surface of tubular W.

Probe Head 207:

Data acquisition devices and/or sensors examining outer surface of tubular W.

Looking now at FIG. 3 in greater detail, it will be seen that nozzle head 205 comprises one or more nozzles 212. FIG. 3 depicts four (4) nozzles 212, in a line off center. However, such configuration of nozzles 212 on FIG. 3 is exemplary only, and nothing in this disclosure should be construed to limit nozzle head 205 to provide any particular number of nozzles 212 in any particular configuration. Other embodiments, consistent with the scope of this disclosure, might provide fewer or greater than four (4) nozzles 212, and might deploy them on center or in different locations off center.

Relating nozzle head 205 as shown on FIG. 3 to the exemplary ODS operational sequence described above, it will be seen that nozzles 212 on nozzle head 205 may enable both the high pressure wash and the low pressure wash. It will be further appreciated that different embodiments of nozzle head 205, wherein each nozzle head 205 provides different numbers, locations and configurations of nozzles 212, may enable different combination of operations (such as steam clean, wash, rinse, spray, coat, etc.) according to user selection.

Relating abrasive heads 206 as shown on FIG. 3 to the exemplary ODS sequence described above, it will be appreciated that abrasive heads 206 may provide steel brushes, rattling heads, flap wheels or any other abrasive tooling in any combination or sequence to further clean, treat or smooth the outer surface of tubular W. FIG. 3 depicts abrasives 213 on abrasive heads 206 in generic form for this reason. In a currently preferred embodiment of the ODS, for example only, the three (3) abrasive heads 206 nearest nozzle head 205 provide abrasives 213 in the form of rotating steel brushes, while the three (3) abrasive heads 206 nearest probe head 207 provide abrasives 213 in the form of rotating flap wheels. In this embodiment, optionally, a nozzle 212 on neighboring nozzle head 205, or on any of abrasive heads 206 themselves, may also be provided and dedicated to cleaning the steel brushes embodying abrasives 213. Nothing in this disclosure should be construed, however, to limit the ODS to this embodiment, or to any configuration, type or number of abrasives 213 or abrasive heads 206.

Probe head 207 as shown on FIG. 3 provides data acquisition probes and sensors for examining and acquiring information about tubular W's outer surface, condition, wall thickness and other parameters. This examination and information gathering process is disclosed in greater detail below in paragraphs later on in this disclosure describing the Data Acquisition System ("DAS"). Probe head 207 may provide all types of sensors, including, without limitation, magnetic, ultrasonic, laser and other types of sensors. Nothing in this disclosure should be interpreted to limit the type or number of sensors provided by probe head 207.

Although not illustrated, other embodiments of the ODS may supplement the data acquisition capability of probe head 207 by optionally providing additional sensors on the inside of shrouds 211. For reference, shrouds 211 are called out on FIG. 3.

Sensor data from probe head 207 and shrouds 211 may be further enhanced or supplemented by the optional addition of imaging technology positioned to scan tubular W's outer surface during ODS operations (such optional imaging technology not illustrated). For example, a thermal imaging camera ("infrared thermography") may be used to detect, record and quantify temperature differentials in the outer surface of tubular W. Such temperature differentials may typically (1) indicate excess moisture found in cracks and pores in tubular W, and (2) measure rates of heat exchange in steel densities and volumes. The imaging data may thus be used easily and conventionally to detect cracks, thickness variations, and porosity in the wall or on the surface of tubular W.

Advantageously, the imaging data may be in the form of a Gaussian (i.e. rainbow) color swath, conventionally displaying lower temperatures in "cooler" colors such as blue, green and cyan, and higher temperatures in "hotter"/ "brighter" colors such as red, yellow and magenta. Anomalies in tubular W such as a surface crack, subsurface crack, porous pipe wall (i.e. less dense wall), and/or variation in wall thickness may be identified via detection of a corresponding temperature gradient (caused by excess moisture and thus lower temperatures in and around the anomaly) when compared to the temperature gradient of a healthy/ continuous run of steel. While such temperature gradient analysis is available at ambient temperatures, the sensitivity (and corresponding efficacy) of the analysis is enhanced if hot water is applied prior to scanning.

Referring back now to FIG. 1, it will be appreciated that although not illustrated in FIG. 1, the Scorpion System's ODS is operable via conventional positioning apparatus to position tubular W with respect to ODS assembly 201 ready for operations. In a preferred embodiment, such positioning apparatus may move ODS assembly 201 with respect to tubular W so as to correctly position the operational tooling on ODS assembly 201 with respect to the external surface of tubular W. In other embodiments, such positioning apparatus may alternatively, or also, position the tubular W with respect to ODS assembly 201.

Figure 4:
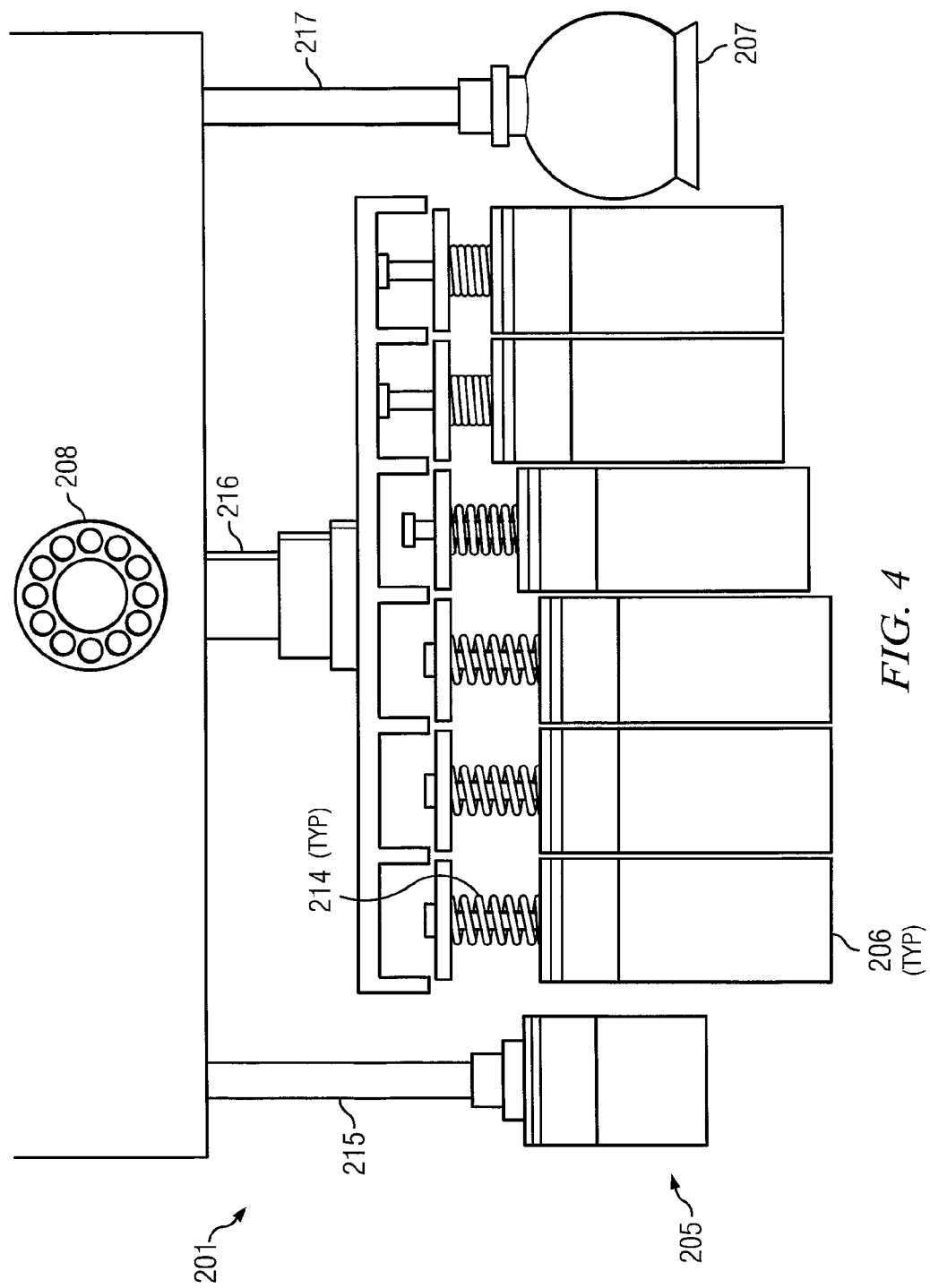
FIG. 4 illustrates one embodiment of the ODS in elevation view.

FIG. 4 illustrates additional, more precise positioning apparatus once ODS assembly 201 is initially positioned with respect to tubular W by conventional positioning apparatus, per the previous paragraph. FIG. 4 is an enlargement of ODS assembly 201 shown more generally on FIG. 1, and depicts aspects of ODS assembly 201 in greater detail. FIG. 4 further depicts ODS assembly 201, nozzle head 205, abrasive heads 206, probe head 207 and gear wheel 208 consistent with the correspondingly-numbered features shown on FIGS. 1 and 2 (and such features' accompanying disclosure herein).

Referring now to FIG. 4, it will be seen that nozzle head 205 is suspended on nozzle head piston 215, while probe head 207 is suspended on probe head piston 217. Abrasive heads 206 generally, as a group, are suspended on abrasive head piston 216. Abrasive heads 206 are then further suspended individually via corresponding abrasive head springs 214. In this way, each of nozzle head 205, abrasive heads 206 and probe head 207 may be more precisely positioned, independently of one another, with respect to the outer surface of tubular W (tubular W omitted for clarity on FIG. 4) according to user selection.

With respect to nozzle head 205, FIG. 4 shows that independent extension and retraction of nozzle head piston 215, as required, will allow nozzle head 205 to be positioned to a precise user-selected location above the outer surface of tubular W. Likewise, FIG. 4 shows that independent extension and retraction of probe head piston 217, as required, will allow probe head 207 to be positioned to a precise user-selected location above the outer surface of tubular W.

With respect to abrasive heads 206, as a group, FIG. 4 shows that extension and retraction of abrasive head piston 216 will allow abrasive heads 206, as a group, to be positioned to a precise user-selected location above the outer surface of tubular W. Further, via compression and release of abrasive head springs 214, FIG. 4 shows that abrasives 213 on abrasive heads 206 (see FIG. 3) may be kept in spring pressure contact with the outer surface of tubular W while abrasive heads 206 operably move along tubular W. Further, the independent suspension of each abrasive head 206 on its own abrasive head spring 214 allows each abrasive head 206 (and corresponding abrasives 213) to conform to the local shape or contour of the outer surface of tubular W as it operably moves along tubular W.

Although FIG. 4 illustrates an embodiment of ODS assembly 201 in which each abrasive head 206 has one corresponding abrasive head spring 214, it will be understood that the scope of this disclosure is not limited in this regard. It will be appreciated that suspension on additional springs may allow individual abrasive heads 206 to conform yet more closely (e.g., via pivoting) to the local shape or contour of the outer surface of tubular W as it operably moves along tubular W. In other embodiments, some described with reference to FIGS. 5 through 11, neighboring individual abrasive heads 206 may be connected together via, for example, an articulated connection, to create a similar effect.

Referring again to nozzle head piston 215, abrasive head piston 216 and probe head piston 217 on FIG. 4, it will be understood that the scope of this disclosure is not limited to extending or retracting these pistons to position their corresponding heads solely prior to commencing operations. It will be appreciated that further extensions or retractions of pistons 215, 216 and/or 217 may alter, as required, the precise position of nozzle head 205, abrasive heads 206 and probe head 207 with respect to the outer surface of tubular W while ODS assembly 201 is moving with respect to tubular W. It will be further understood, however, that in some embodiments, lasers and magnetic proximity sensors (not illustrated) are a primary means of adjustment for contours in the outer surface or tubular W, rather than extensions or retractions of pistons 215, 216 and/or 217 on the fly.

Reference is now made to FIGS. 5 through 13B, which illustrates ODS assembly 220 as an alternative embodiment to ODS assembly 201 as illustrated on FIGS. 1 through 4. It will be appreciated that the disclosure above to general principles, features and aspects of the ODS, regardless of the embodiment of ODS assembly or "buggy", applies equally to the embodiments disclosed below with reference to FIGS. 5 though 13B.

Figure 5:
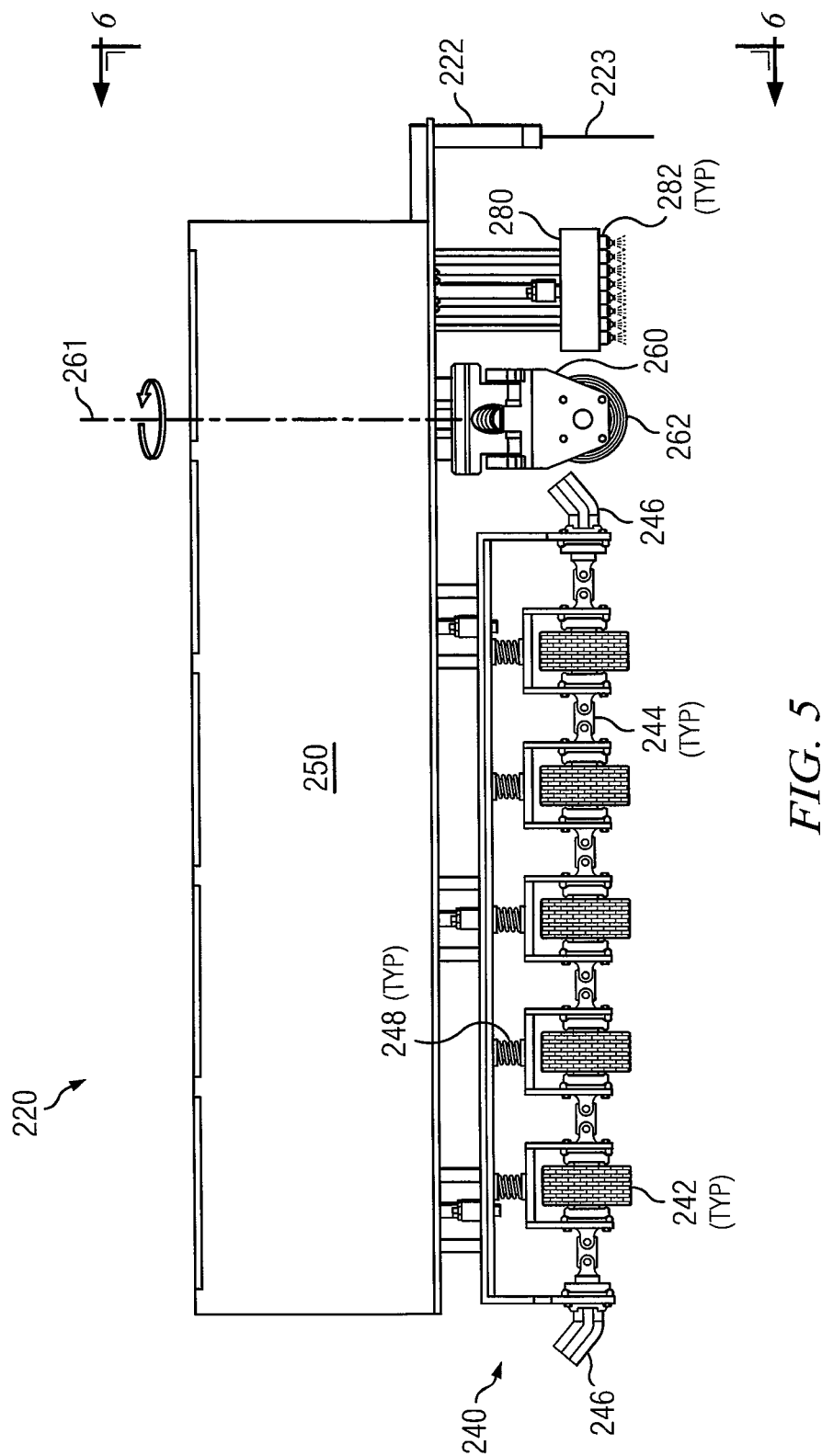
FIG. 5 illustrates another embodiment of the ODS in elevation view.

Further, for the avoidance of confusion on FIGS. 5 though 13B, it will be understood that, for illustration purposes on this disclosure only, alternative ODS assembly embodiments 201 and 220 are illustrated to run in opposite directions from a default rest position (such default resting position defined for purposes of this paragraph only as resting ready to begin engaging a tubular). ODS assembly 201 embodiment on FIGS. 1 through 4 is illustrated to run right-to-left on the page from a default rest position (see arrow 204 on FIG. 1 and associated disclosure above). In contrast, ODS assembly 220 embodiment of FIGS. 5 though 13B is illustrated to run left-to-right on the page from such a default rest position.

Thus, with reference to FIG. 5, as ODS assembly 220 moves and engages a tubular beneath, ODS laser 222 first detects the end of the tubular and then ODS laser 222's field of view 223 begins to scan the external surface of the tubular below as the tubular rotates. Information from scanning by ODS laser 222 is used by ODS assembly 220's control system (not illustrated) to inspect and analyze characteristics of the tubular as described in greater detail below. Currently-preferred embodiments of ODS assembly 220 further include an optical camera also deployed in combination with ODS laser 222. The optical camera also scans the tubular beneath within field of view 223 as illustrated on FIG. 5 (and other Figures) and receives corresponding images of the tubular for processing in combination with information from ODS laser 222. For the avoidance of doubt, the term "ODS laser 222" as used hereafter in this disclosure refers to a combination of a laser and an optical camera scanning the tubular in field of view 223. The operation of the laser and optical scanner in combination is discussed further below in this disclosure.

FIG. 5 further depicts ODS assembly 220 providing fluid jet assembly 280 next to ODS laser 222. Fluid jet assembly 280 provides jets 282, which spray or blast fluids (in gaseous or liquid state) onto the external surface of a rotating tubular beneath. Individual jets 282 are user-selectable according to operational needs. By way of example only, and without limitation, jets 282 may provide: (1) a steam blast, a high pressure water blast (nominally at about 20,000 psi but not limited to any such pressure) or even a fluid-borne abrasive blast for operations such as concrete removal or hydroblasting operations, especially if tubular W has a severely rusted or scaled outer surface; (2) a low pressure/high temperature wash (nominally at 3,000 psi/300 deg F. but not limited to any such pressure or temperature), for general tubular cleaning operations, including salt wash and rust inhibitor coating; and/or (3) a compressed air or gas (such as nitrogen) blast, for drying or (in the case of compressed air) removal of surface debris. Fluid jet assembly 280 is described in greater detail below with reference to FIGS. 13A and 13B.

FIG. 5 further depicts swivel brush assembly 260 next to fluid jet assembly 280 on ODS assembly 220. Swivel brush assembly 260 provides swivel brush 262 (which may, per further disclosure below, be a laminate of planar brushes) at the point of contact with the external surface of a rotating tubular beneath. Swivel brush assembly 260 further provides axle structure and conventional power apparatus (such as hydraulic, electric or pneumatic motors) to power-rotate the swivel brush 262 at user-selected speeds on user-selected speed cycles. Swivel brush 262 may be of any suitable size, profile or construction, per user selection, and this disclosure is not limited in this regard. In the embodiments illustrated on FIGS. 5 though 13B, swivel brush assembly 260 provides one swivel brush 262 having an oblate spheroid shape and profile, although swivel brush 262 is not limited to a single brush in other embodiments.

Swivel brush assembly 260 may further be rotated, per user control and selection, about its vertical axis 261 as shown on FIG. 5. In this way, swivel brushes (including, on FIG. 5, swivel brush 262) may be caused to abrade the external surface of a tubular at any user-selected angle relative to the axis of the tubular's rotation. Changes may be made to the angle of abrasion on the fly. This feature acknowledges that certain common oilfield tubulars, such as drill pipe, are conventionally turned in a clockwise direction as drilling into the earth progresses. This drilling rotation causes helical scratching and scarring on the external surface of the tubular. The ability to set and adjust the angle of abrasion on swivel brush assembly 260 permits a more effective cleaning of external surfaces that may have a helical scratch or scar pattern.

Swivel brush assembly 260 on FIG. 5 is also disposed to "tilt" or pivot so that swivel brush 262 follows the contour of a rotating tubular beneath. Such "tilting" or pivoting is about a substantially horizontal axis. Once the general height of swivel brush assembly 260 above a tubular is set, "tilting" or pivoting structure takes over to allow swivel brush assembly 260 to follow the contour of the tubular, while spring structure on swivel brush assembly 260 permits the swivel brush (or brushes) to maintain a substantially constant contact on the surface of the tubular as they pass over local variations in the tubular's diameter. Swivel brush assembly 260 (including the "tilting"/pivoting feature and the contouring feature) is described in greater detail below with reference to FIGS. 12A through 12E.

FIG. 5 further depicts fixed brush train 240 next to swivel brush assembly 260 on ODS assembly 220. Fixed brush train 240 comprises fixed brushes 242, each configured to rotate generally about an axis parallel to the longitudinal axis of a tubular beneath. In illustrated embodiments, fixed brushes 242 provide circular ("wheel"-like) brushes at the point of contact with the external surface of a rotating tubular beneath. Fixed brush train 240 further connects fixed brushes 242 together into a concatenated train thereof via articulated brush joints 244. Embodiments of articulated joints may include conventional u-joints or any other structure suitable for connecting neighboring fixed brushes 242 in articulated fashion. As shown on FIG. 5 (and subsequent Figures), articulated brush joints 244 form an articulated drive shaft which drives fixed brushes 242 to rotate in unison. Individual fixed brushes 242 are thus permitted to move vertically semi-independently of one another, while still all being driven in unison by the articulated drive shaft formed by articulated brush joints 244. Conventional power apparatus (such as hydraulic, electric or pneumatic motors) at either or both ends of fixed brush train 240 may power-rotate all of the fixed brushes in unison at user-selected speeds on user-selected speed cycles. Fixed brushes 242 may be of any suitable number, size, profile or construction, per user selection, and this disclosure is not limited in this regard. In the embodiments illustrated on FIGS. 5 through 11, fixed brushes 242 have a conventional cylindrical shape and profile. Alternatively one or more fixed brushes 242 may have the oblate spheroid ("football") shape described above with respect swivel brush 262 elsewhere in this disclosure, or any user-selected design. It will be also understood that this disclosure is not limited to the number of fixed brushes 242 that may deployed on fixed brush train 242. In the embodiments illustrated on FIGS. 5 though 13B, fixed brush train 240 provides five (5) fixed brushes 242 concatenated into an articulated train, separated by articulated brush joints 244 and driven by two fixed brush motors 246. Nothing in this disclosure should be interpreted, however, to limit fixed brush train 240 to any specific number of fixed brushes 242 and/or brush motors 246.

The concept of the term "fixed" on fixed brush train 240 (as opposed to the term "swivel" on swivel brush assembly 260 described above) refers to the fact that fixed brushes 242 on fixed brush train 240 do not rotate about a vertical axis normal to the axis of rotation of the tubular, and are further constrained from doing so by the interconnection provided by articulated brush joints 244. Fixed brushes 242 on fixed brush train 240 instead form a series of abrading surfaces that rotate in unison on the external surface of the rotating tubular beneath, where the angle of abrasion is consistently normal to the longitudinal axis of the tubular.

FIG. 5 further illustrates that fixed brush train 240 suspends fixed brushes 242 from shock absorbers 248. In the embodiments illustrated on FIGS. 5 to 13B, shock absorbers 248 are spring mechanisms, and fixed brush train 240 provides one shock absorber 248 for each fixed brush 242, although this disclosure is not limited in this regard. It will be appreciated from FIG. 5 that shock absorbers 248 further regulate the semi-independent vertical movement provided to each fixed brush 242 by articulated brush joints 244. The semi-independent vertical movement permits each individual fixed brush 242 the independent freedom to follow the local contour of the rotating tubular beneath as fixed brushes 242 pass over the tubular. Fixed brush motors 246 may nonetheless still drive all fixed brushes 242 in unison. Shock absorbers 248 regulate the independent vertical movement of each fixed brush 242, requiring each fixed brushes 242 to maintain a substantially constant contact on the surface of the tubular as it passes over local variations in the tubular's diameter. Once the general height of fixed brush train 240 above a tubular is set, shock absorbers 248 take over to allow each fixed brush 242 to follow the local contour of the tubular as it passes by beneath. Fixed brush train 240 is described in greater detail below with reference to FIG. 11.

It should be noted that although the above disclosure has referred, with respect to FIG. 5, to swivel brush assembly 260 and fixed brush train 240, nothing in this disclosure should be interpreted to limit swivel brush assembly 260 and fixed brush train 240 to "brushes" in the sense of an abrasion tool with bristles. Swivel brush 262 and fixed brushes 242 may be any abrasive tool, including, but not limited to, wire brushes, flap wheels, or abrasive stone or composite wheels.

FIG. 5 further illustrates top shroud 250 covering structure above fixed brush train 240, swivel brush assembly 260 and fluid jet assembly 280. Top shroud 250 protects against steam, dust, debris, fluid overspray and other by-products of cleaning operations below. Fluid jet assembly 280 is also advantageously covered by a shroud (omitted on FIGS. 5 through 13B for clarity) during operations in order to contain steam, fluid overspray, debris, etc., caused by the operation of jets 282. A further containment structure advantageously deployed about the entire operation of ODS assembly 220 (again, omitted on FIGS. 5 though 13B for clarity) restrains steam, fluid overspray, dust, debris, etc. from contaminating the general surroundings, and further enables recycling of recyclable fluids after jets 282 may have administered them.

Figure 6:
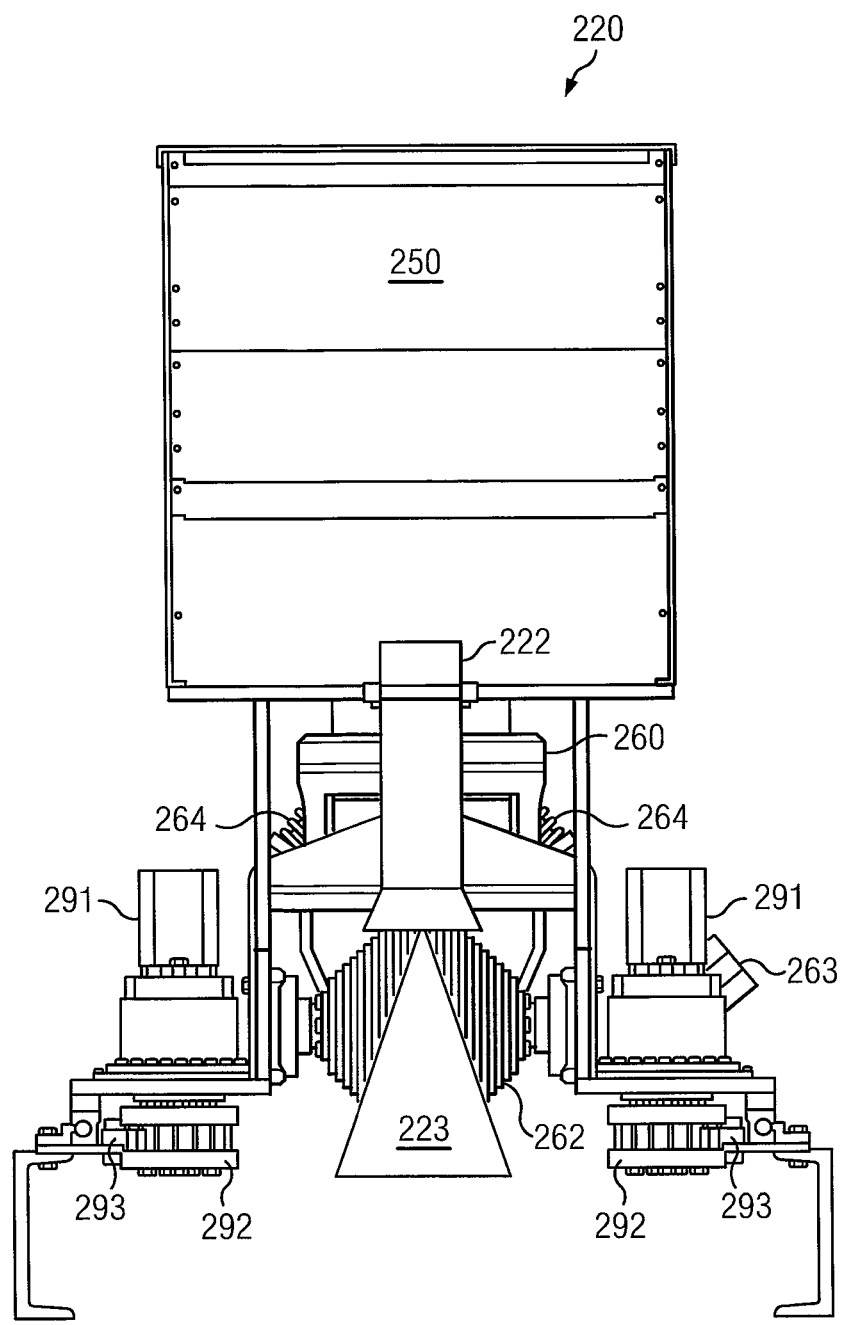
FIG. 6 is an end view as shown on FIG. 5.

FIG. 6 is an end view of ODS assembly 220 as shown on FIG. 5. FIG. 6 illustrates features and aspects of ODS assembly 220 as also shown on FIG. 5. FIG. 6 also illustrates features and aspects of ODS assembly 220 that were omitted from FIG. 5 for clarity. Fluid jet assembly 280, however, which was shown and described above with reference to FIG. 5, is omitted for clarity from FIG. 6 so that features and aspects of swivel brush assembly 260 may be better seen.

FIG. 6 depicts ODS assembly with top shroud 250, ODS laser 222 and laser field of view 223, as described above more fully with reference to FIG. 5. Swivel brush assembly 260 may also be seen on FIG. 6, including swivel brush 262, as also described above with reference to FIG. 5. It will be seen on FIG. 6 more clearly that in the ODS assembly embodiment of FIGS. 5 though 13B, swivel brush 262 has been user-selected to be in the shape and profile of an oblate spheroid (although swivel brush 262 as disclosed herein is not limited to such a shape and profile). The oblate spheroid shape may be created by laminating together a plurality of planar circular brushes of gradually varying diameter. The laminate may vary from smallest diameter at the ends up to largest diameter in the middle.

The oblate spheroid (or colloquially, "football") shape and profile gives advantageous results when the angle of abrasion is rotated towards normal to the longitudinal axis of the tubular underneath. An optimal angle of attack may be found for abrading the external surface of the tubular, where the oblate spheroid shape maximizes contact and abrasive efficiency in view of the local contour or diameter of the tubular immediately below swivel brush 262. It will be appreciated that as the angle of abrading attack approaches normal (90 degrees) to the longitudinal axis of the tubular, the more the coned edge of the oblate spheroid shape comes to bear on contours on the tubular, reducing the potential brush pressure of swivel brush 262 on contours that increase the local diameter of the tubular. Tilting structure on swivel brush assembly 260, as described in more detail below, with reference to FIGS. 12A through 12E, further mitigates against damage to the tubular from swivel brush 262 contacting the external surface of the tubular too hard (especially during tubular contour changes that increase the tubular's local diameter). Tilting springs 264 (which are part of the tilting structure described in more detail with reference to FIGS. 12A through 12E) may be seen on FIG. 6, although partially hidden from view. Likewise swivel brush motor 263 (for power rotating swivel brush 262) may also be seen on FIG. 6, although again partially hidden from view. As noted above with reference to FIG. 5, swivel brush motor 263 may be any conventional power apparatus (such as a hydraulic, electric or pneumatic motor) to power-rotate swivel brush 262 at user-selected speeds on user-selected speed cycles.

It is useful to highlight some of the advantages provided by the ability of swivel brush assembly 260 and fixed brush train 240 to adapt to local variations in contour and diameter of the tubular beneath, as described above with reference to FIGS. 5 and 6. Without such ability to adapt to local variations in contour and diameter, "forcing" a rotating tubular under swivel brushes or fixed brushes may place undesirable local stress on, for example, the tubular, the ODS assembly, the structure for rotating the tubular, and the structure for supporting the tubular while it rotates. Over time, such undesirable stress may cause failures, or at least premature wear and tear on the tubular and/or the surrounding ODS and related structure. The ability of swivel brush assembly 260 and fixed brush train 240 to adapt to local variations in contour and diameter of the tubular thus mitigates against such stresses, wear and tear, and/or failures.

A further advantage provided by the ability of swivel brush assembly 260 and fixed brush train 240 to adapt to local variations in contour and diameter of the tubular is that, in combination with the ability to power-rotate swivel brush 262 and fixed brushes 242 in either direction, substantial improvements in the operational life of brushes become available. The ability of swivel brush assembly 260 and fixed brush train 240 to adapt to local variations assists in keeping swivel brush 262 and fixed brushes 242 at (or near) optimal brush pressure on the external surface of the tubular, avoiding premature brush wear by "crushing" the brushes and wear surfaces together. Further, the ability to periodically reverse the direction of rotation of swivel brush 262 and fixed brushes 242 during brushing operations (as may be required in ODS cleaning operation cycles anyway) further serves to enhance brush life by distributing brush wear more evenly.

Figure 10:
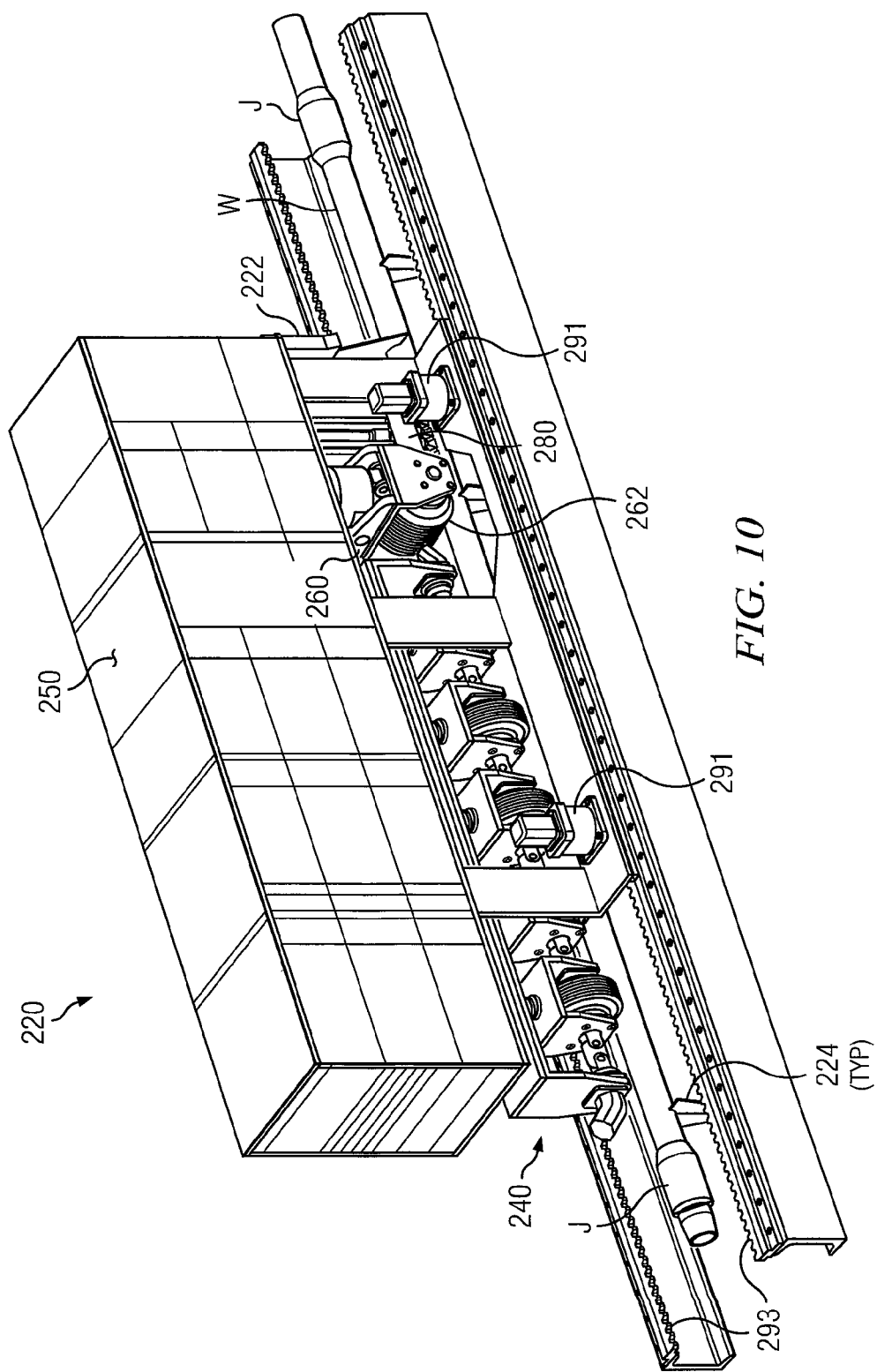
FIG. 10 is a further isometric view of ODS embodiment of FIGS. 5-7, with a propulsion drive and track detail added.

FIG. 6 also illustrates exemplary propulsion structure for ODS assembly 220. It will be appreciated that ODS assembly may be propelled back and forth above the external surface of a stationary but rotating tubular by any conventional method and/or structure. The propulsion structure illustrated on FIG. 6 (and elsewhere in FIGS. 5 though 13B) is by way of example only. FIG. 6 illustrates ODS propulsion motors 291 deployed either side of ODS assembly 220. Propulsion motors 291 may be any conventional power apparatus (such as hydraulic, electric or pneumatic motors). Propulsion motors 291 rotate roller pinions 292, which in turn are engaged on geared tracks 293. Note that on FIG. 6, geared tracks 293 may only be seen in section. However, with momentary reference to FIG. 10, geared tracks 293 may be seen in isometric view from above. FIG. 10 also illustrates propulsion motors 291, although roller pinions 292 are hidden from view on FIG. 10. It will be further appreciated from FIGS. 6 and 10 that in the embodiments of ODS assembly 220 illustrated and described, an example of four (4) propulsion motors 291 propel ODS assembly 220 up and back along two (2) geared tracks 293. This disclosure is not limited in this regard, however, and other embodiments may deploy other numbers of propulsion motors 291 in various configurations on various numbers of geared tracks 293, per user design. Although not illustrated in detail on FIGS. 6 and 10, it will be understood that the travel of ODS assembly 220 is further kept in a straight line parallel to the longitudinal axis of a tubular beneath by bearings and related conventional structure rolling on and between guide rails.

It will be also understood from FIGS. 6 and 10 that the operation of propulsion motors 291 may be controlled closely to allow a high level of corresponding control over the movement (and speed thereof) of ODS assembly 220 above a rotating tubular. Movement may be directed at any time, per user control, in a forward or backward direction at user-selected speeds. Such control over movement of ODS assembly 220 (and corresponding control over ODS operations) may be combined with control over concurrent internal tubular (MLI) operations and over rotation of the tubular to give a highly controlled cleaning, inspection and/or data analysis of the tubular at an enterprise level.

Figure 7:
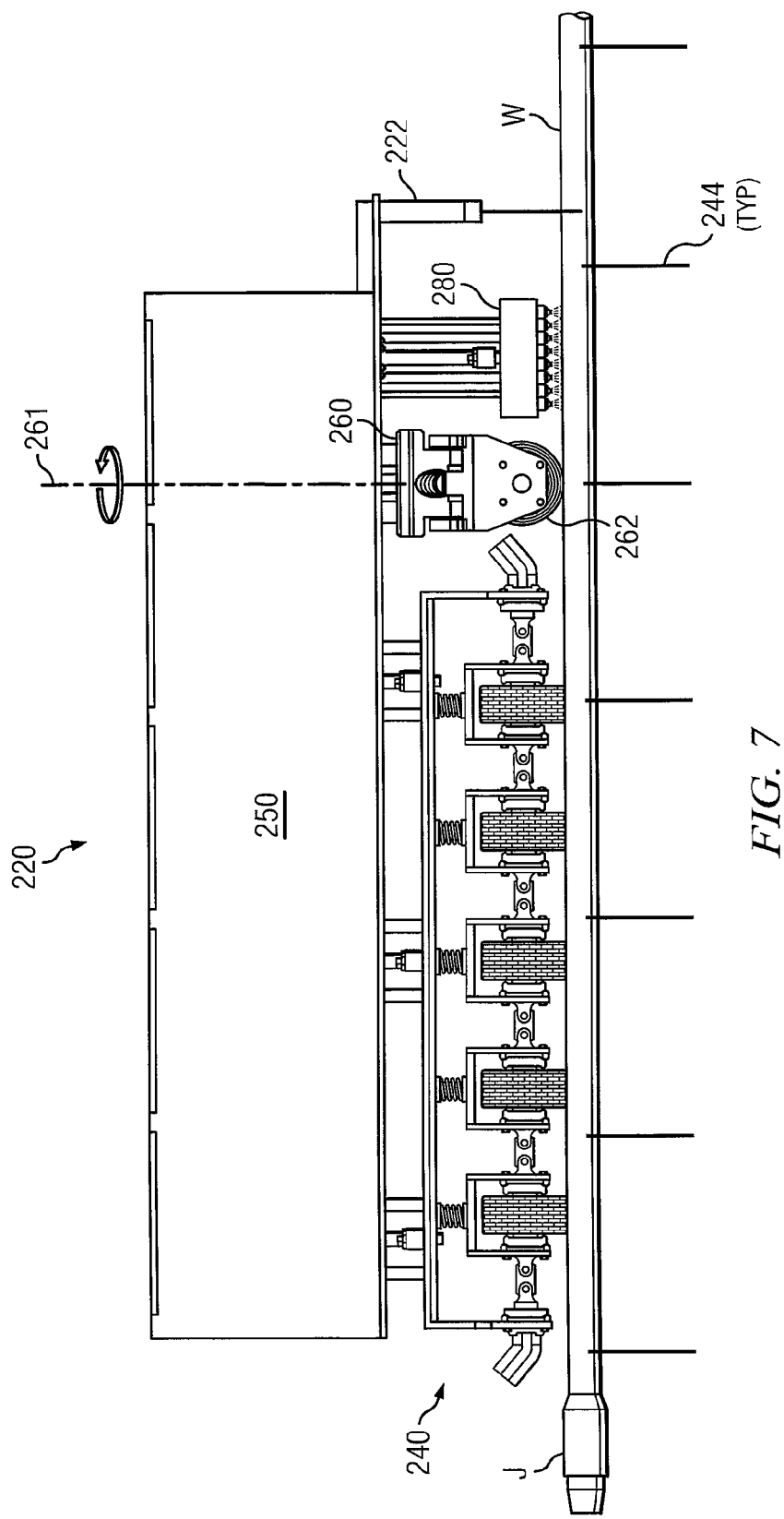
FIG. 7 illustrates the ODS embodiment of FIG. 5 disposed to operate on tubular W.
Figure 8:
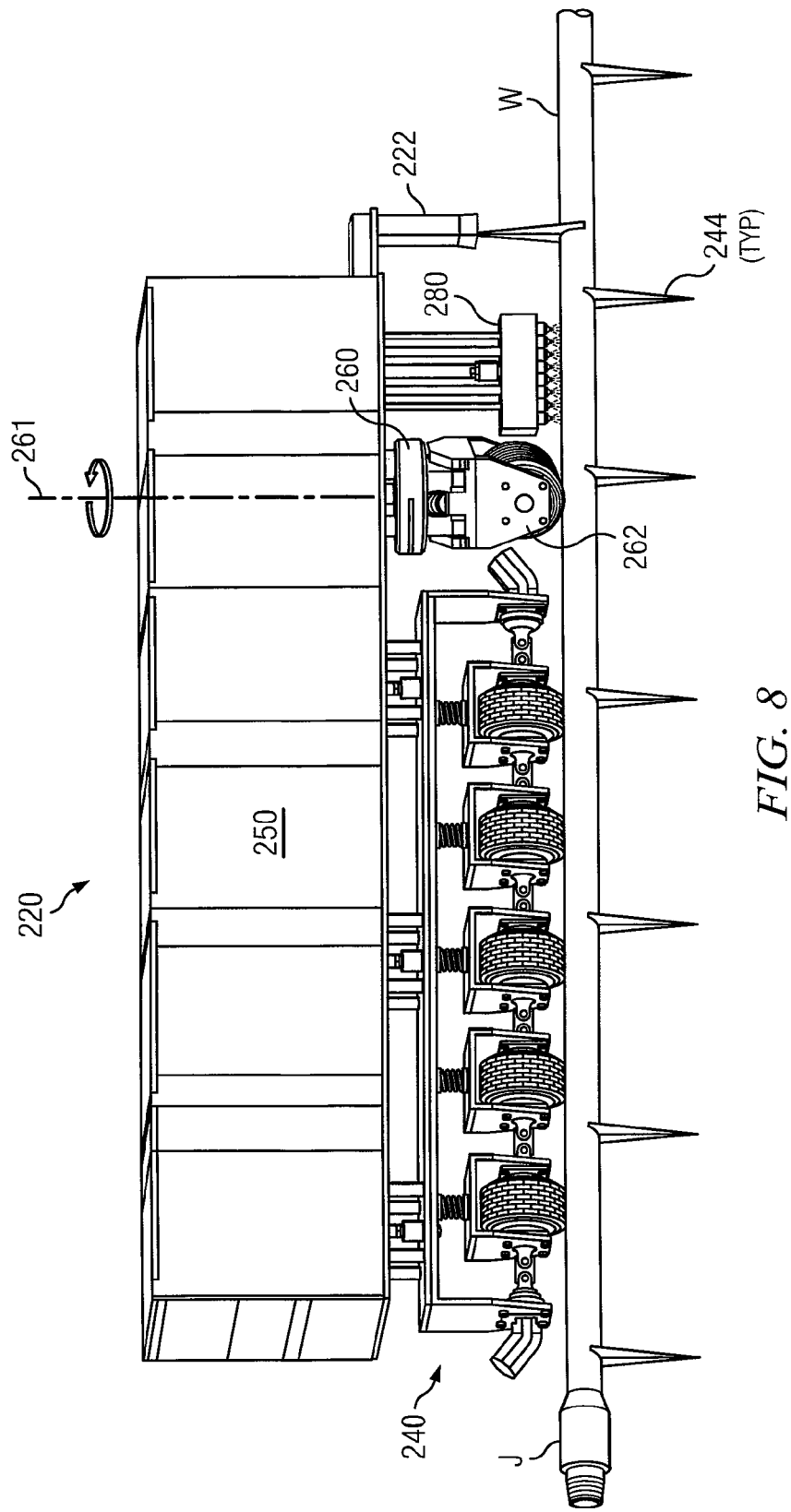
FIGS. 8 and 9 illustrate the ODS embodiment of FIGS. 5-7 in different isometric views.
Figure 9:
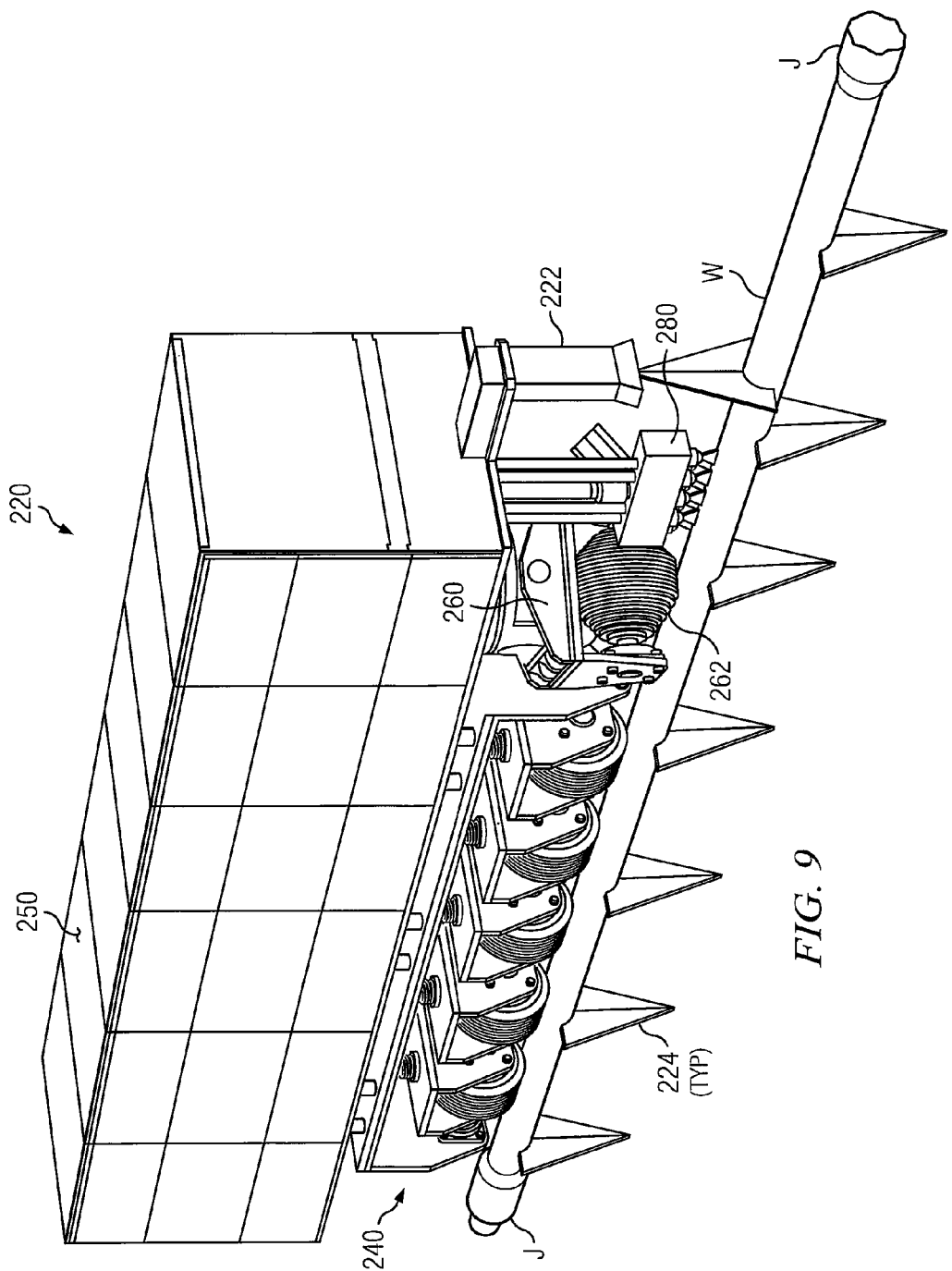

Reference is now made to FIGS. 7, 8 and 9 together. FIGS. 7, 8 and 9 illustrate substantially the same structure from different views. FIG. 7 is an elevation view. FIGS. 8 and 9 are isometric views from different angles.

FIGS. 7, 8 and 9 depict ODS assembly 220 in substantially identical form to ODS assembly 220 as depicted on FIG. 5 (including ODS laser 222, fluid jet assembly 280, swivel brush assembly 260, fixed brush train 240 and top shroud 250), except that on FIGS. 7, 8 and 9 also depict rotating tubular W beneath ODS assembly 220 and on which ODS assembly is operating. Tubular W includes at least one joint J. FIGS. 7, 8 and 9 further depict fixed lasers 224 beneath tubular W, whose fields of view scan the underside of tubular W as it rotates. It will be understood that fixed lasers 224 are stationary in user-selected fixed locations. Information gained from scans of fixed lasers 224 is advantageously combined with laser and optical camera information from ODS laser 222 as it moves back and forth above tubular W and coincides with (co-locates with) individual fixed lasers 224. The processing and use of laser and optical camera information is discussed in greater detail below.

All the disclosure above describing aspects and features of ODS 220 with reference to FIGS. 5 and 6 applies equally to ODS 220 as depicted on FIGS. 7, 8 and 9. With particular reference to swivel brush assembly 260, it will be seen on FIGS. 8 and 9 that swivel brush assembly 260 has been rotated about vertical swivel brush assembly axis 261 (shown on FIGS. 7 and 8) so that the plane of rotation of swivel brush 262 is at an angle to the longitudinal axis of tubular W. Referring back to disclosure associated with FIGS. 5 and 6, such rotation allows swivel brush 262 to take up a user-selected angle of attack when abrading the external surface of rotating tubular W, to account for features such as, for example, surface defects, helical wear patterns or discontinuities in diameter (such as at pipe joints J, described in more detail immediately below) on tubular W.

Pipe joints J illustrated on FIGS. 7, 8 an 9 illustrate examples of the variations in local contour and diameter that ODS assembly 220 may encounter during its travel back and forth while operating on the external surface of tubular W. Other changes in contour may be caused by, for example (and without limitation), bow or sag in tubular W, local out-of-roundness in the diameter of tubular W, or excessive wear, scarring or pitting at local points. As noted in earlier disclosure with reference to FIGS. 5 and 6, ODS assembly 220 is disposed to account for such local variations in contour and diameter of tubular W via articulated brush joints 244 and shock absorbers 248 on fixed brush train 240 (described in more detail below with reference to FIG. 11), and via tilting springs 264 and related structure on swivel brush assembly 260 (described in more detail below with reference to FIGS. 12A through 12E).

Propulsion features and aspects illustrated on FIG. 10 (including propulsion motors 291 and geared tracks 293) have already been described in association with earlier disclosure making reference to FIG. 6. Other features and aspects of ODS assembly 220 illustrated on FIG. 10 are substantially as also described above with reference to FIGS. 5 through 9. Features illustrated on FIG. 10 that are also illustrated on FIGS. 5 through 9. carry the same numeral throughout.

Figure 11:
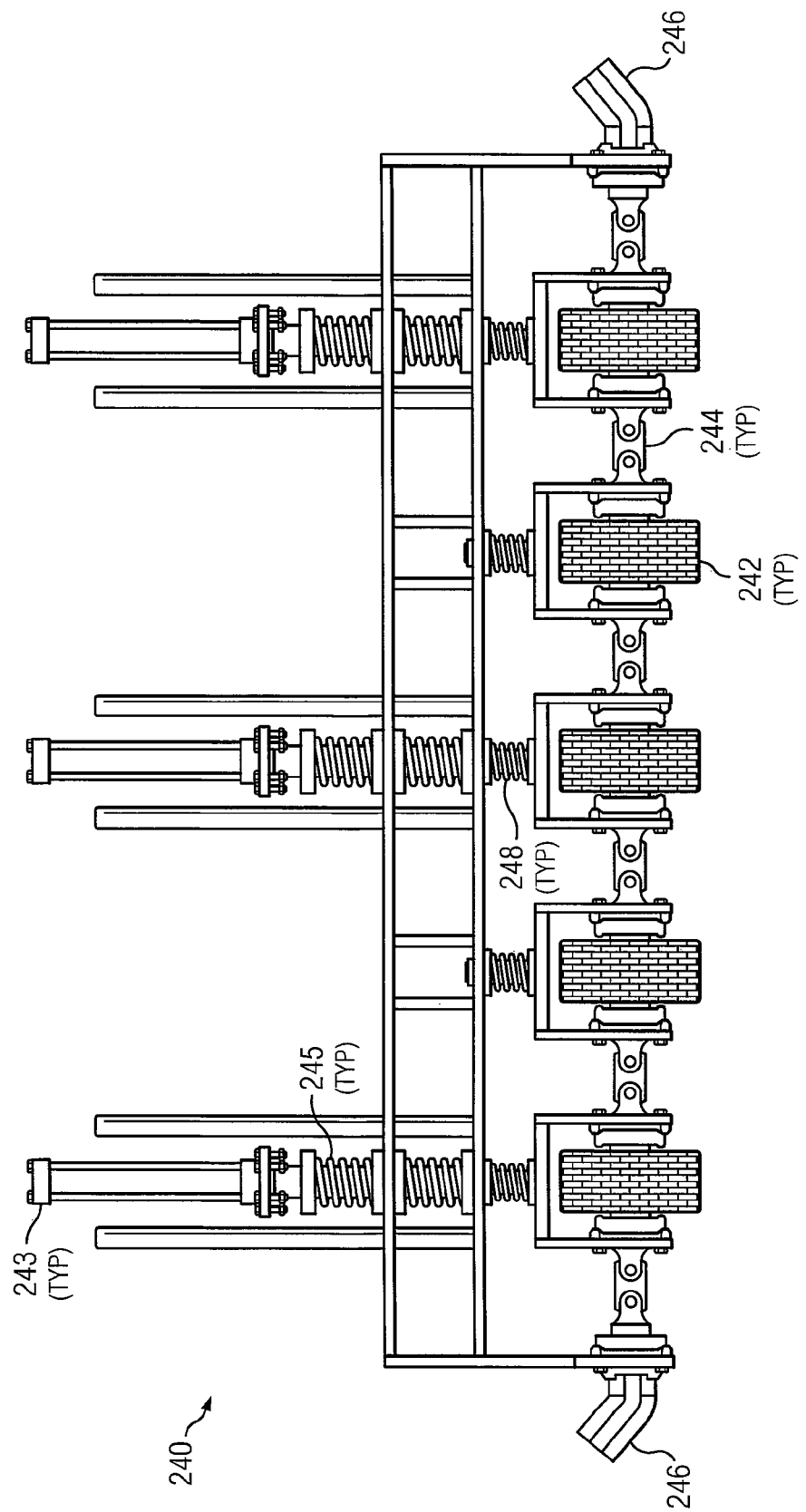
FIG. 11 is an isolated elevation view of fixed brush train 240.

FIG. 11 illustrates additional features of fixed brush train 240 from FIGS. 5 through 10, with some enlargement and in isolation, and with top shroud 250 removed. All earlier disclosure regarding fixed brush train 240 with reference to FIGS. 5 through 10 applies equally to FIG. 11. It will be recalled from such earlier disclosure that the concatenation of articulated brush joints 244 forms an articulated drive shaft for fixed brushes 242 driven by fixed brush motors 246 at either or both ends thereof. The articulated nature of the connections between fixed brushes 242 allows for semi-independent vertical movement of individual fixed brushes 242 while still permitting fixed brush motors 246 to rotate all fixed brushes 242 in unison. It will be further recalled that shock absorbers 248 further regulate the semi-independent vertical movement of individual fixed brushes 242 to enable fixed brushes 242 to maintain contact with the external surface of a tubular below despite local variations in tubular contour or tubular diameter.

FIG. 11 further illustrates fixed brush train lifts 243 for setting fixed brush train 240 at a general height above a tubular, according to user-selection. Fixed brush train lifts 243 may be any conventional lifting mechanism, such as a hydraulically-actuated cylinder, as illustrated on FIG. 11. It will be appreciated that fixed brush train lifts 243 may be actuated to set a desired elevation for fixed brushes 242 with respect, for example, to a desired amount of brush pressure on a tubular having a nominal diameter. Fixed brush train lifts 243 actuate against fixed brush train lift springs 245 in order to provide spring resistance to the actuation of train lifts 243. This spring resistance assists with smooth and precise actuation, which in turn assists with smooth and precise application of brush force by fixed brushes 242 on an expected nominal diameter tubular. As noted above, variations in local contour or diameter of the tubular may then be accounted for by semi-independent vertical movement of individual fixed brushes 242 provided by articulated joints 244 and shock absorbers 248.

It will be further appreciated from FIG. 11 that fixed brush lifts 243 are not limited to setting an elevation for fixed brushes 242 that is parallel to the longitudinal axis of the tubular. Angles for fixed brush train 240 may be set such that fixed brushes 242 may apply greater pressure to the tubular at one end rather than the other. It will also be understood that this disclosure is not limited to deploying three (3) fixed brush train lifts 243 on one installation, as illustrated on FIG. 11. The example of FIG. 11 is suitable for the exemplary fixed brush train 240 embodiment also illustrated on FIG. 11 with five (5) fixed brushes 242. Other embodiments of fixed brush train 240 may deploy more or fewer than two (3) fixed brush train lifts 243, and this disclosure is not limited in this regard.

Figures 12A, 12B:
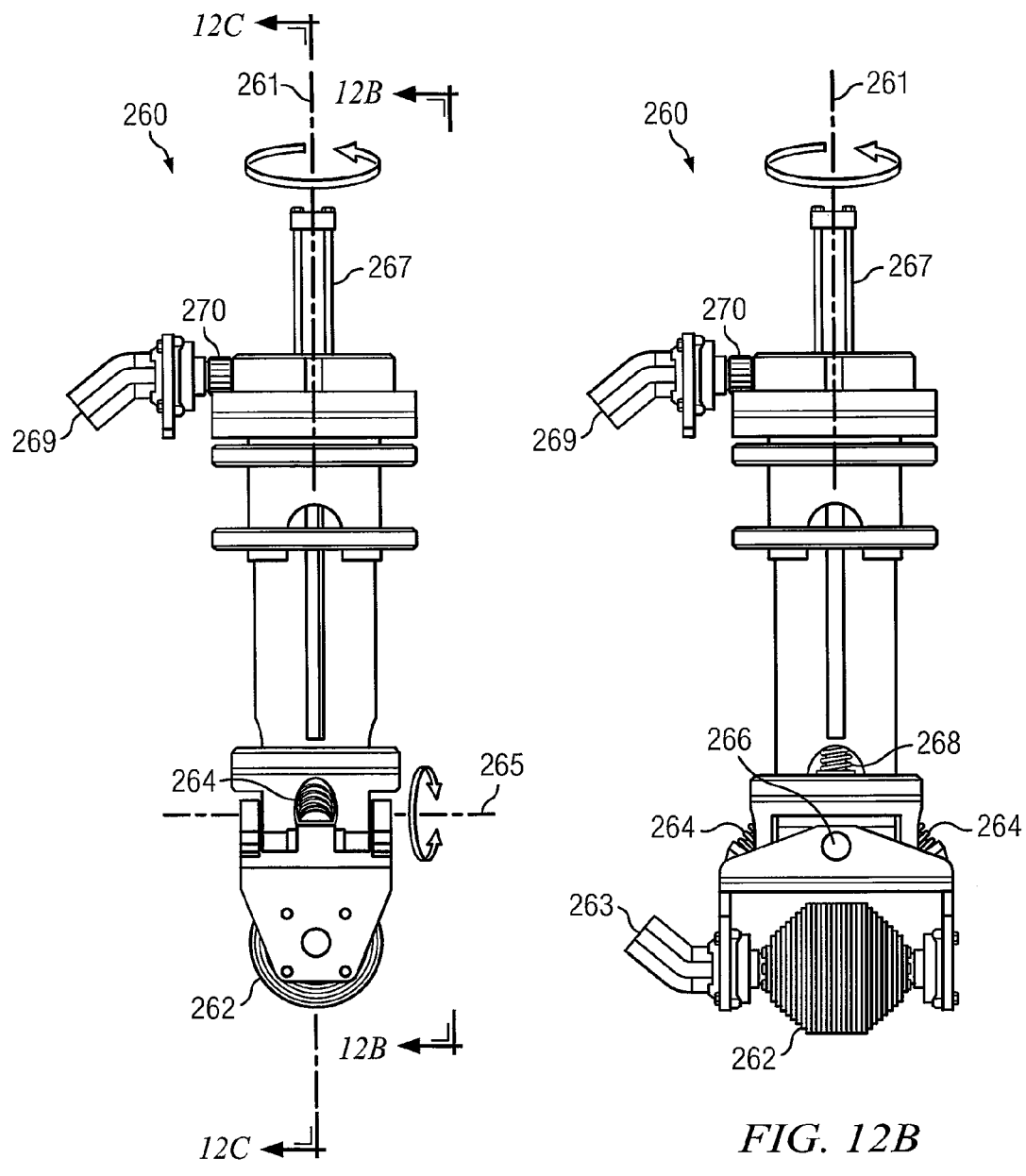
FIGS. 12A and 12B are isolated elevation views of swivel brush assembly 260.
Figure 12C:
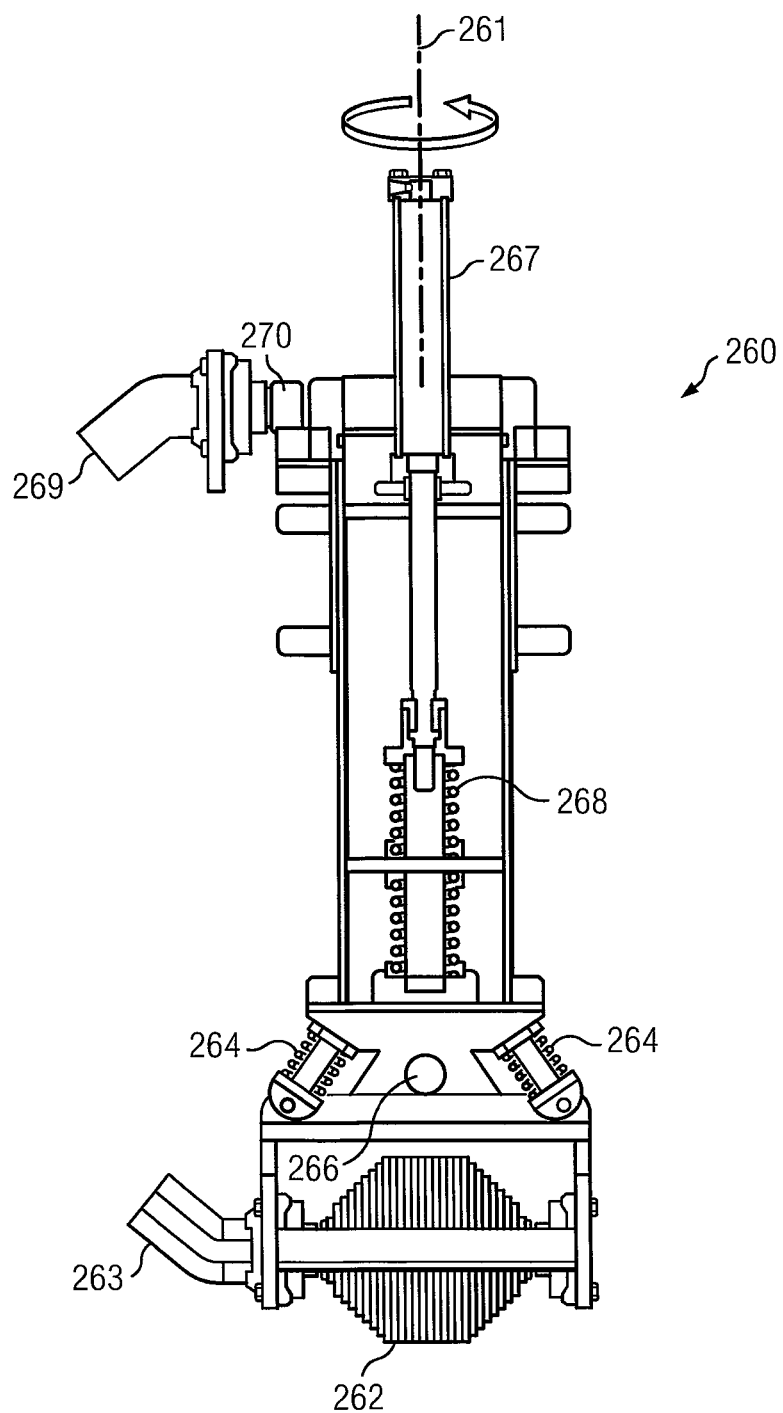
FIG. 12C is a cutaway view of swivel brush assembly 260.

FIGS. 12A through 12E should be viewed together. FIGS. 12A through 12E illustrate additional features of swivel brush assembly 260 from FIGS. 5 through 10, with some enlargement and in isolation, and with top shroud 250 removed. FIG. 12B is an elevation view of swivel brush assembly 220 as shown on FIG. 12A. FIG. 12C is a cutaway view of swivel brush assembly 220 also as shown on FIG. 12A. All earlier disclosure regarding swivel brush assembly 260 with reference to FIGS. 5 through 10 applies equally to FIGS. 12A through 12E. It will be recalled from such earlier disclosure (in particular with reference to FIGS. 5 and 6) that swivel brush 262 may be set to rotate and abrade at an angle to the longitudinal axis of a tubular beneath, per user selection via rotation of swivel brush assembly 262 about vertical swivel brush axis 261. It will also be recalled from earlier disclosure that illustrated embodiments of swivel brush assembly 260 deploy swivel brush 262 with an oblate spheroid (colloquially, "football") shape and profile for advantageous performance over variations in the tubular's local contour and diameter.

Earlier disclosure also described a "tilt" (or pivot) feature on swivel brush assembly 260 to assist swivel brush 262 in maintaining brush pressure while following the local contour of a rotating tubular beneath. FIGS. 12A through 12E describe the tilting feature in more detail. Referring to FIGS. 12A through 12E, tilting is about swivel brush assembly tilting axis 265 on FIG. 12A, also represented by pivot 266 on FIGS. 12B and 12C. Such tilting will thus be seen to be about a substantially horizontal axis. Tilting is regulated by tilting springs 264, seen on FIG. 12B to hold swivel brush 262 (and connected structure) in spring equilibrium about pivot 266. In this way, once the general height of swivel brush assembly 260 above a tubular is set, tilting springs 264 allow swivel brush 262 to tilt about pivot 266 as it encounters local variations in the contour or diameter of the tubular beneath, During such tilting, responsive to compression pressure from tilting springs 264, swivel brush 262 may still maintain a substantially constant contact on the surface of the tubular.

FIGS. 12A through 12E further illustrate swivel brush assembly lift 267 for setting swivel brush assembly 260 at a general height above a tubular, according to user-selection. Swivel brush assembly lift 267 may be any conventional lifting mechanism, such as a hydraulically-actuated cylinder, as illustrated on FIGS. 12A through 12B. It will be appreciated that swivel brush assembly lift 267 may be actuated to set a desired elevation for swivel brush 262 with respect, for example, to a desired amount of brush pressure on a tubular with nominal diameter below. As shown best on FIG. 12C, swivel brush assembly lift 267 actuates against swivel brush assembly lift spring 268 in order to provide spring resistance to the actuation of swivel brush assembly lift 267. This spring resistance assists with smooth and precise actuation, which in turn assists with smooth and precise application of brush force by swivel brushes 262 on an expected nominal diameter tubular. As noted above, variations in local contour or diameter of the tubular may then be accounted for by tilting springs 264 holding swivel brush 262 in spring equilibrium about pivot 266.

FIGS. 12A through 12E further illustrate structure to enable controlled rotation of swivel brush 262 about vertical swivel brush axis 261, further to more general disclosure above regarding such rotation. Swivel rotation motor 269 on FIGS. 12A through 12E operates swivel rotation gears 270 to rotate swivel brush 262 about axis 261. Swivel rotation motor 269 may be any conventional power apparatus (such as a hydraulic, electric or pneumatic motor) to power-rotate swivel brush 262 about axis 261 per user control.

Figure 12D:
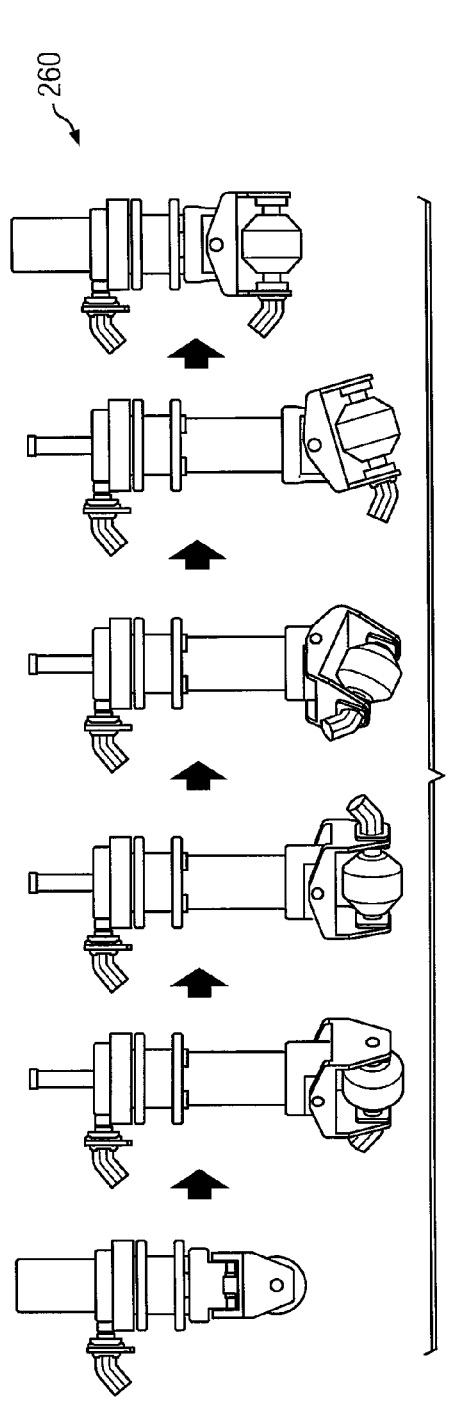
FIGS. 12D and 12E are stroboscopic views of swivel brush assembly 260.
Figure 12E:
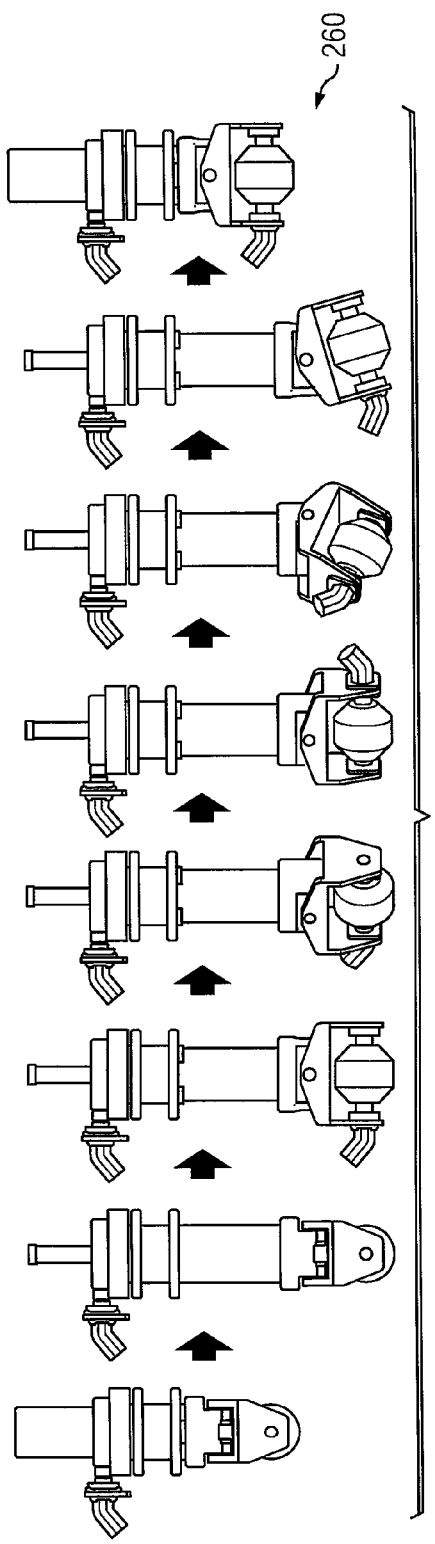

FIGS. 12D and 12E illustrate, in stroboscope or "freeze-frame" style, the various motions available to swivel brush assembly 260 during normal operation. FIGS. 12D and 12E illustrate (with further reference to FIGS. 12A through 12C): (1) actuation of swivel brush assembly lift 267 to set a general height for swivel brush 262, (2) rotation of swivel brush 262 about vertical swivel axis 261, and (3) tilting of swivel brush 262 about pivot 266.

Figures 13A, 13B:
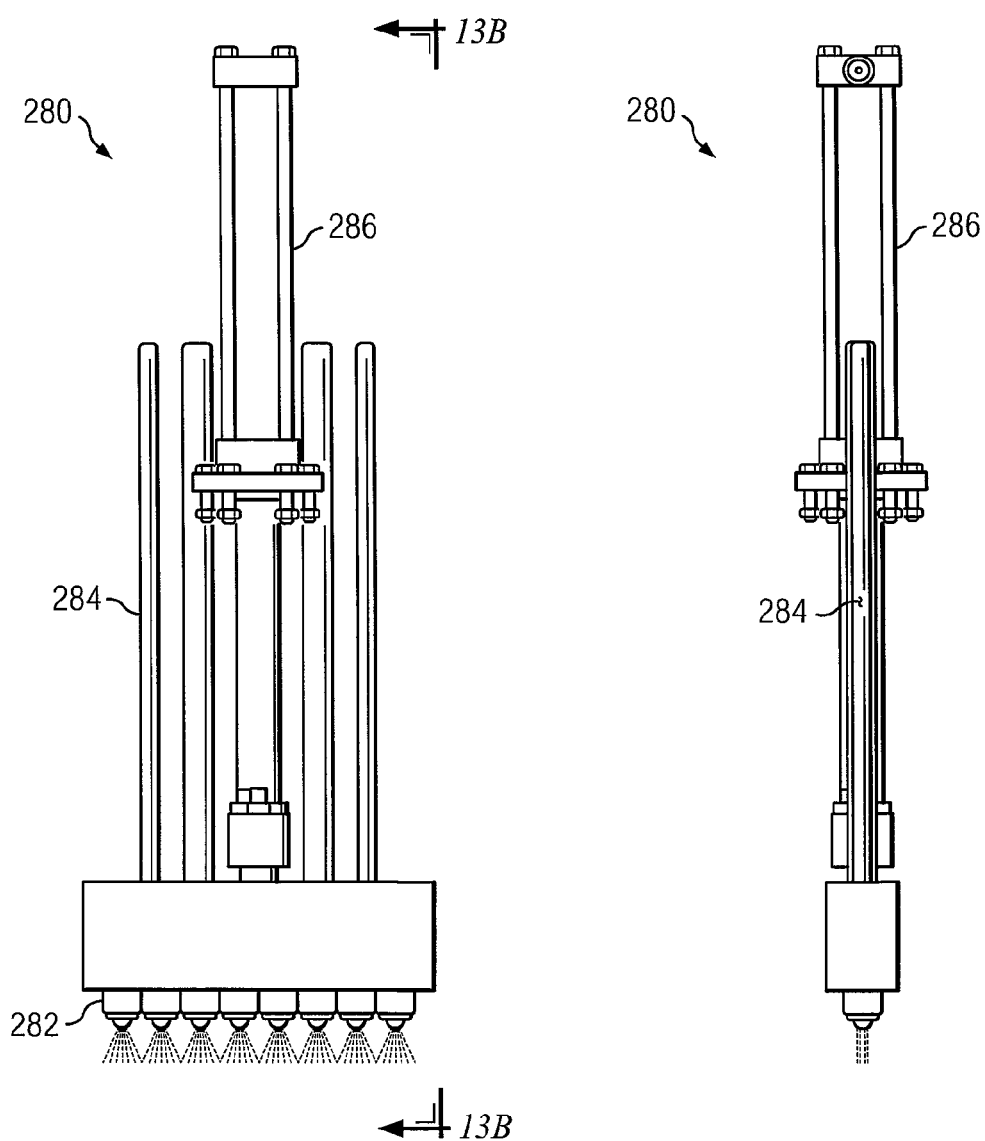
FIGS. 13A and 13B are isolated elevation views of fluid jet assembly 280.

FIGS. 13A and 13B should be viewed together. FIGS. 13A and 13B illustrate additional features of fluid jet assembly 280 from FIGS. 5 through 10, with some enlargement and in isolation, and with top shroud 250 removed. FIG. 13B is an elevation view of fluid jet assembly 280 as shown on FIG. 13A. All earlier disclosure regarding fluid jet assembly 280 with reference to FIGS. 5 through 10 applies equally to FIGS. 13A and 13B. It will be recalled from such earlier disclosure (in particular with reference to FIG. 5) that fluid jet assembly 280 provides jets 282, which spray or blast fluids (in gaseous or liquid state) onto the external surface of a rotating tubular beneath. Individual jets 282 are user-selectable according to operational needs.

FIGS. 13A and 13B further illustrate fluid jet assembly lift 286 for setting fluid jet assembly 280 at a general user-desired height above a tubular. Electronic control systems then, on the fly, make small changes in the elevation of jets 282 above the external surface of the tubular by actuating jet height control cylinders 284. In this way, a user-selected distance between jets 282 and the external surface of the tubular may be maintained, notwithstanding local variations in contour or diameter of the tubular that jets 282 may encounter during their travel along the length of the tubular.

The electronic control systems described above (for maintaining distance between jets 282 and external surface of tubular) utilize real time information regarding the tubular collected by ODS laser 222. Referring back to earlier disclosure associated with FIGS. 5 through 9, it will be recalled that as ODS assembly 220 travels back and forth above a rotating tubular, ODS laser 222 scans the external surface of the tubular. It will be further recalled that in currently preferred embodiments, ODS laser 222 includes both a laser and an optical camera to scan the external surface of the tubular. Laser scans by ODS laser 222 may identify contours and external surface anomalies on the tubular of all types in real time, including surface defects (such as, for example, scratches, gouges, divots, pitting, and laminations), as well as larger variations in tubular diameter such as pipe joints. Such laser scan data regarding the external surface of the tubular is also referred to in this disclosure as "contouring data" or "contour data", and is derived from laser data but not optical camera data. As will be described in greater detail below, contour data derived solely from laser scans is used for operational cleaning purposes (including for adjusting the height of fluid jet assembly 280, swivel brush assembly 260 and fixed brush train 240 above the tubular's surface) as well as for inspection purposes. On the other hand, optical camera data is used in combination with laser data from ODS laser 222, and further in combination with data from fixed lasers 224 beneath the tubular, in order to derive dimensional data regarding the outside diameter ("OD") of the tubular for inspection purposes. The advantages of optical camera data, and the use thereof in deriving OD dimensional data, are also discussed in more detail below.

Returning now to further consideration of contour data derived from laser scans (only) by ODS laser 222, it will be appreciated that substantial information regarding the contours of a tubular may be obtained. Given knowledge (1) of the absolute position of ODS laser 222 on a tubular at a particular moment in time, and (2) of the rotational speed of the tubular at such moment in time, ODS laser 222 may "map" the contours over the entire external surface of the tubular. Knowledge of the absolute position of ODS laser 222 may be obtained via methods that include (1) knowing when ODS laser 222 first encounters the tubular as it begins its first pass over the tubular, and (2) establishing relative position to the "first encounter" from sensors, such as optical sensors, deployed in the propulsions system (such as in, or attached to, roller pinions 292 and/or geared tracks 293 as illustrated and described above with reference to FIGS. 6 and 10). It will be appreciated that such optical sensors may conventionally translate measured speed and direction of travel of ODS assembly 220 into a position relative to the "first encounter".

Further consideration will now be given to data regarding the OD of the tubular derived for inspection purposes from both laser and optical camera data from ODS laser 222 (on FIGS. 5 through 10), in combination with laser data from fixed lasers 224 (on FIGS. 7 through 10). Such laser and optical camera data may be combined to obtain real time "caliper"-type measurements of the tubular at intervals along the tubular's length. Combined and coordinated laser data and optical camera data from ODS laser 222 and fixed lasers 224 may enable dimensional irregularities or anomalies in the tubular (such as sag, wobble or bow in the tubular, or areas where the tubular is out-of-round) to be identified and location-tagged along the tubular's length. This "caliper"-type data may be used in real time to correct (via adjustment and compensation): (1) overall dimensional data regarding the OD of the tubular and any point along its length, as well as (2) contour data obtained from laser data from ODS laser 222 as described in the immediately preceding paragraphs.

It is useful to highlight some of the aspects and advantages in combining optical camera data with laser data in obtaining information about the OD of the tubular, or "pipe" as used in the following optical camera discussion. Determining the outside diameter of a drill pipe optically is a challenge. As an object moves closer or farther from a fixed zoom lens, it grows and shrinks respectively. For measurement purposes on pipes of varying diameters and centerlines, simply taking a picture and determining the size of a pipe is not practical. However, the combined use of an optical lens with a range finding laser adds the axis of reference necessary to account for the varying centerline distances and calculation of diameters possible.

In order to achieve a pipe diameter measurement, an image is taken of the pipe using a line scan camera. The line scan camera captures a slice of the pipe. This slice contains a one dimensional array of information, essentially containing 'material' and 'non-material'. The 'material' being pipe, the "non-material" representing anything outside the pipe. The differentiation between the two is made using threshold values on the grayscale information contained in the array. For instance, given a grayscale color spectrum of 8 values, non-material may be any value below 3, while material would show 4 through 8. With the combination of a light source and a filter on the lens, only the light reflecting off pipe material will be allowed into the camera. This will allow for a fine resolution between "material and "non-material" and for fast image processing and information output.

Now, a calculation of the number of "material" pixels in the array divided by (material+non-material) pixels will give the percentage material in any particular slice of information. Without a frame of reference, this number is useless. However, the combination of this percentage with a range finding laser at each point a slice is taken allows for accurate calculation of length based on percentage of material.

As an example, if at 1 inch away from the lens, an image contains 50% material and the known size of the pixel array at 1 inch away is 1 inch, the object size may be calculated to be 0.5 inches. Taking this one step further, if at 10 inches away from the lens the pixel array is known to contain 10 inches of information, an image containing 5% material pixels will also be 0.5 inches. Now, using this concept in combination with a range finding laser and careful calibrations of the pixel array size to distance ratio, an image, or slice of a pipe, can be used to very accurately calculate diameter based on simply the data contained in a slice and the reference distance the lens is from the pipe, which is provided by the range finding laser.

Using a high scan rate and high resolution camera, very accurate calculations can be made as to the diameter of the pipe. Combining multiple line scan cameras will multiply the accuracy. This system will traverse the length of the pipe, taking slices of information quickly and accurately and allow for a novel way to determine pipe diameter information.

Returning now to consideration of contour data, it will thus be appreciated that contour data regarding the tubular acquired by laser scans by ODS laser 222 (and preferably corrected with "caliper"-type data) may then be fed in real time to control systems on other operating systems on ODS assembly 220. Such real time contour data may then be used to make corresponding adjustments to the operating systems. For example, and without limitation; such real time contour data may be used to make corresponding adjustments that include: (1) adjusting the distance between jets 282 and the external surface of the tubular in order to maintain a constant distance therebetween; (2) adjusting the angle of attack of swivel brush 262 in order to obtain optimum abrasion; (3) adjusting the general elevation of swivel brush assembly 260 or fixed brush train 240 in order to accommodate a large tubular diameter change such as a pipe joint; (4) adjusting the speed or direction of rotation of swivel brush 262 or fixed brushes 242 according to upcoming conditions; or (5) adjusting the speed or direction of travel of ODS assembly 220 according to upcoming conditions.

It is useful to highlight some of the advantages of maintaining a constant distance between jets 282 and the external surface of the tubular, notwithstanding local contour or diameter variations in the tubular. If jets 282 are too close to the tubular's external surface, even momentarily, then damage to the tubular's surface (such as steel erosion and cutting) may occur, especially during high pressure fluid blast cycles. Such damage occurs substantially immediately if the right conditions exist. On the other hand, if jets 282 are too far away, again even momentarily, then fluid jet assembly 280's operations (such as cleaning, rinsing, coating, drying, etc.) may be less than fully effective, and possibly compromised. As distance between jets 282 and the tubular's surface increases, operating effectiveness decreases exponentially.

It is therefore highly advantageous to maintain an optimal distance between jets 282 and the external surface of the tubular, so that the operating effectiveness of jets 282 is maximized without causing damage to the tubular's surface. The electronic control system using data that includes real time contour data obtained by laser data from ODS laser 222, as described above, is useful to maintain that optimal distance.

It will be further appreciates that the ODS contour data acquisition and processing system, and related electronic control systems, described in the preceding paragraphs, may also be combined and coordinated in real time with concurrent data regarding the internal surface and diameter of the tubular. Exemplary internal data acquisition structure and technology is described further below with reference to "Internal Cleaning and Inspection". Such concurrent data may supplement ODS contour data to provide additional information regarding the tubular in real time, including, for example, tubular wall thickness information and further analysis of points of interest such as apparent cracks, etc.

It may be advantageous in ODS operations to acquire ODS contour data in a first pass over the tubular, and then return (or go back on a second pass) for more information. Further data regarding the OD of the tubular may be gathered in order to prepare a summary thereof. Additionally further investigation may be conducted on points of interest (such as cracks, pitting, gouges, etc.) identified and location-tagged on a previous pass. Second- (or subsequent-) pass investigations may call for the ODS to pass by points of interest more slowly, or at a different tubular rotation speed, than might be optimal for cleaning operations on an previous pass.

The following sections of this disclosure now focus a mechanical inspection data acquisition system useful in conjunction with the ODS technology also disclosed herein. The ODS contour data acquisition and processing system, and related electronic control systems, described in the preceding paragraphs, dovetail into the disclosed mechanical inspection Data Acquisition System ("DAS"). The following DAS disclosure should also be read in conjunction with associated disclosure set forth further below with reference to "Internal Cleaning and Inspection". Note, however, that although disclosed as part of the Scorpion System, the DAS technology could be used independently in many tubular processing operations. It is not limited to deployment on a tubular cleaning system.

Conventional technology calls for pipe joints and other tubulars to receive regular EMI (Electro-Magnetic Inspection or equivalent nomenclature) analysis to check the integrity of the joint. EMI analysis provides data, ideally in a graph format, interpretable to see, for example, if the tubular's wall thickness has fallen below a certain acceptable thickness at any point, or if the tubular has any unacceptable defects such as pits or cracks.

EMI is conventionally provided by passing electromagnetic sensors over a stationary tubular, such as a joint of drill pipe. Alternatively, the tubular can be conventionally passed over a stationary electromagnetic sensor apparatus. This operation can be done in the shop or in the field. If an anomaly is found, the EMI sweep operation has to stop in order to pinpoint the anomaly. Further analysis is then done manually at the site of the anomaly (usually sonic analysis) to determine whether the pipe joint is in or out of specification. In some embodiments of the ODS, an EMI sweep operation may be configured by deploying an EM "donut" ring on ODS assembly 220 as shown on FIGS. 5 though 10. The donut ring may sweep the tubular as ODS assembly 220 moves up and back above the rotating tubular.

The Scorpion System's DAS is an optional add-on to the other aspects of the Scorpion System disclosed elsewhere in this disclosure. The DAS provides sensors at suitable locations (such as, without limitation, on drift tooling or dedicated sensor lances on the MLI, or on the insides of shrouds or on a dedicated probe head on some embodiments of the ODS according to FIGS. 1 through 4, or as recorded by laser(s) and optical camera(s) onboard ODS laser 222 and by fixed lasers 224 on other embodiments of the ODS according to FIGS. 5 through 10). These sensors are provided to analyze the state of the rotating tubular. A further particularly advantageous sensor placement (without limitation) would be to locate a resistivity tool in an internal drift.

The DAS sensors may be of any suitable type for inspecting the tubular. The DAS sensors may be, for example, electromagnetic sensors, sonic sensors, lasers, cameras (still or video, optical or otherwise) accelerometers, or any other type of sensor, and the DAS is expressly not limited in this regard. Examination of the tubular by the sensors may be done at the same time that cleaning operations are done, or alternatively during separate inspection passes of the MLI or the ODS along the tubular.

It will be appreciated that the DAS may be enabled by any suitable data acquisition system capable of taking multiple sensor readings at high sampling rates, and then converting those readings into human-interpretable qualitative and quantitative data regarding the sampled specimen. Such data acquisition systems are well known in the art. The software also compares the sampled data with stored data, again in real time. As will be described in further detail below, the stored data may include, for example, earlier inspections of the same specimen, or paradigms such as theoretical scans of a specimen that meets applicable performance specifications.

A primary principle of the DAS is to acquire, in real time, sufficient data regarding the state of a tubular to have generated a unique and highly-individualized data "signature" of the tubular representing its current state as sampled. The signature represents any recorded and repeatable combination of sampled information points regarding the state of the tubular. Such sampled information points may include, by way of example and without limitation, qualitative and quantitative data regarding:

(a) location, shape and nature of anomalies on interior and/or exterior walls of tubular (such as scratches, scars, pits, gouges, repairs or cuts from prior service, or manufacturing defects of a similar nature);

(b) location and nature of variations in wall thickness of tubular;

(c) location and nature of variations in cross-sectional shape of the tubular; or (d) location and nature of cracks or other points of weakness within the tubular.

The foregoing data is advantageously in high resolution. The more sampled information points regarding a tubular are combined into a signature, the more unique and highly-individualized the signature is likely to be. It will be appreciated that the "sample-richness" or "granularity" of the DAS signature of a tubular may be further enhanced by combining synchronous sampling of the exterior and interior of the tubular. One option for data acquisition in an illustrated embodiment of the Scorpion System is for an MLI lance with data acquisition capability and the ODS probe head or laser (as described elsewhere in this disclosure) to be run synchronously down the tubular with all such sensors (internal and external) being in data communication with each other. In this way, the DAS may acquire real time data regarding the tubular in which the data quality is enhanced by concurrent and substantially co-located sampling from both sides of the wall of the tubular. The DAS software and hardware is configured to allow a user to zoom in on points of interest on a graphical display in order to classify and measure anomalies.

A further feature in preferred embodiments of the DAS is a "stop/start curtain" that may be provided on embodiments of the ODS. The stop/start curtain is particularly advantageous in embodiments of the Scorpion System where "synchronous" examination (as described above) of the interior and exterior of the tubular is available. However, the curtain feature is not limited to such embodiments. The curtain feature refers to one or more sensors placed on each end of the ODS, and may use the optical range to be in the form of a "light" curtain. These sensors detect when the tubular is present underneath, and when it is not. The sensors may be lasers or lights (hence the colloquial reference to a "curtain") or any other sensor capable of such detection. As the ODS moves toward the tubular to commence operations, the curtain at the near end of the ODS detects the end of the tubular and synchronizes/coordinates DAS processing to this event. As the ODS nears completion of its travel over the tubular, the curtain at the near end of the ODS detects the end of the tubular and warns the DAS of this event. The curtain at the far end of the DAS eventually detects the end of the tubular and notifies that DAS that a full sweep of the tubular has been completed. It will be appreciated that the curtain feature may then be operated in reverse for a pass of the ODS along the tubular in the opposite direction.

Once acquired, the signature of the tubular may then be compared with the expected corresponding signature of a paradigm. The paradigm may be anything from the expected signature of a brand new, perfectly-manufactured tubular (the "perfect pipe"), to the expected signature of a tubular that meets all applicable performance specifications for the tubular when in service (for example, minimum wall thickness over a certain percentage of the tubular and no more than a certain number of pits, cracks or other anomalies above a certain size or depth). A summary report may then be produced that may summarize and highlight key points of interest in the comparison, including anomalies in OD measurements. In addition, the Scorpion System may generate "One-Way Tracking Tags" that may be affixed to each length of tubular processed by the System. Each tag advantageously includes serial number information (which may be in the form of bar codes) that ties the tubular to any corresponding cleaning and inspection information collected or generated by the Scorpion System.

It will be appreciated that with regard to comparison to the expected signature of a tubular that meets all applicable performance specifications, the DAS provides an advantageous substitute to conventional EMI analysis. Information regarding the condition of the tubular may be obtained concurrently with cleaning operations, potentially obviating the need for additional, separate EMI analysis after cleaning.

The current signature of the tubular may also be compared with earlier corresponding signatures of the same tubular to identify specific changes in the tubular since the previous inspection. Alternatively, the current signature of the tubular may be compared against stored data sets or other known signatures where such a comparison will be expected to identify areas of interest in the tubular such as deterioration of wall integrity, or other wear or damage. Such stored data sets or known signatures might include, for example, "perfect pipe" in one type of comparison, or tubulars with known defects or wear and tear in another type of comparison.

In the currently preferred embodiment, the signature of the tubular appears as a series of graphs and other visual media. This makes comparison with paradigms or previous signature of the tubular relatively straightforward. Nothing in this disclosure should be interpreted, however, to limit the DAS or the Scorpion System in this regard.

The disclosed "tubular signature acquisition" aspect of the DAS also provides further advantages in the field of tubular tracking. There has been a long-felt but unsolved need in the art for a predictable, durable and cost-effective technique for marking and then tracking tubulars. Prior art systems have used physical stamping of the tubular metal, etching, magnetic flux and other techniques in attempts to mark tubulars with individual, unique identity codes. The codes can then be used to track tubulars through histories of operational service, cleaning, inspection, repair and other events. The codes can also be used to track inventory.

As noted, a predictable, durable, simple, cost-effective technique for marking and then tracking tubulars has so far eluded the industry. All of the techniques described above to mark and "read" an identity code on a tubular have had limited success. The heavy duty manner in which tubulars are stored, transported and managed, and the aggressive service into which they are put, all contribute to rapid deterioration, corruption or degradation of an identity code placed on the tubular by conventional means.

The unique and highly-individualized "signature" of a tubular acquired and stored by the DAS, as described above, provides an identifier which may be used in tracking tubulars through their lifetimes of service, cleaning, storage, inspection and repair. An exemplary tubular tracking methodology is disclosed below with reference to FIG. 32, and is made available by tracking the DAS's signature of the tubular. This exemplary tubular tracking methodology provides an advantage over conventional tracking systems in that it does not require identifying markings on the tubular to survive the rigors of downhole service. Nothing in this disclosure should be interpreted, however, to limit the availability and use of DAS tubular signatures to the methodology disclosed below with reference to FIG. 32.

FIG. 32 is a flow chart illustrating tubular tracking method 400 comprising Blocks 401-404. Tracking begins with the Scorpion System's DAS, as described in this disclosure, providing a unique ID code for a tubular (block 401). The ID code may be the full "signature" of the tubular (as described above), or a summarized, abbreviated or alternative unique ID code.

Moving to block 402 on FIG. 32, the tubular is then physically labeled with the ID code. This labeling may be robust but temporary, and may be enabled by any labeling technology. The labeling should be able to survive normal handling, storage and transport of the tubular, but need not be expected to survive service in a drill string or other rigorous environment. Examples of suitable labeling include adhering a sticker to the outside of the tubular's surface, or water-stenciling, etching, painting or punching an ID code into the tubular's wall. The disclosure of method 400 is not limited in this regard, however. The label may optionally provide the ID code in multiple formats, including human-readable characters (such as a series of numbers and/or letters) and/or a machine-readable bar code.

Preferably, to avoid potential loss of traceability, the tubular may be labeled shortly after cleaning and other operations by the Scorpion System. For example, either as part of an ODS cycle or separately, apparatus may be provided to label the tubular immediately after cleaning operations are completed by the Scorpion System.

Once labeled, the tubular may be tracked via the label through handling, storage, transport, and/or any other non-service phase of its life cycle.

Referring now again to FIG. 32, method 400 uses the example of the tubular next being put into service as part of a drill string in a downhole operation. It will be appreciated, however, that method 400 is not limited to such service for the tubular. As part of being placed into service, the tubular (and its associated ID code) is cross referenced with its location in the drill string or other service (block 403). In this way, per block 404, even if the service removes the tubular's ID code label (or otherwise renders the label illegible), the tubular may be relabeled, if necessary, upon separation from the drill string or other service, based upon its known location in the drill string or other service.

Once relabeled, the tubular may again be tracked through handling, storage, transport, etc., through to its next cycle of cleaning and/or inspection operations, preferably by the Scorpion System. The Scorpion System's DAS may compare the post-service condition of the tubular with its records of the pre-service condition. If the tubular's ID code is dependent on or derived from the DAS signature of the tubular, the ID code may need updating to begin the next cycle of tracking.

Although not illustrated on FIG. 32, it will be appreciated that in the event that re-labeling in block 404 does not occur, the Scorpion System's DAS may still be able to re-identify the tubular by comparison of the post-service DAS signature with other stored signatures in its records. Preferably, the tubular may be able to be re-identified via simple correlation of signatures. However, where a tubular's post-service signature may suggest more than one tubular candidates based on historical records, a process of elimination based upon a known tracked location of some of the candidates may further help identify the tubular under review.

It will be appreciated that, with reference to FIG. 32, method 400 is not limited to use with a tubular ID code provided by and/or updated by the Scorpion System's DAS. Method 400 has equivalent applicability using a unique ID code assigned to the tubular by any other method.

There are numerous advantages to tracking a tubular in a manner such as has been disclosed. For example, a tubular may carry with it a history of service, examination and physical condition via such tracking. Inventory management is assisted via such tracking. Tubulars that indicate a problem during service may be tagged for later examination via such tracking. These advantages are exemplary only, and the foregoing list thereof is not exhaustive.

Other embodiments of the tubular tracking aspect of the Scorpion System's DAS may also optionally employ a "rotational bar code" to identify and track tubulars. As noted elsewhere in this disclosure, the Scorpion System rotates the tubular at high speeds. This high rotational speed presents an opportunity to mark tubulars with a unique "rotational bar code" and then reliably read the code. This technique allows the rotational bar code to stand a better chance than found in the prior art to withstand heavy duty handling, storage and service without degradation or corruption. It will be appreciated, however, that the rotational bar code disclosed herein is not limited to use with the Scorpion System, and may be used with any other apparatus that can rotate a tubular and sense for marks on the tubular during rotation.

FIG. 33 illustrates the "rotational bar code" technique, in which a tubular inspection system, such as the DAS system described in this disclosure, analyzes a predetermined length L of the tubular W, and identifies point marks 510 found randomly around the outer circumference of tubular W. The predetermined length L may be any length on the tubular W, located at any predetermined longitudinal location on the tubular, up to and including the entire length of the tubular W. The point marks 510 may be made by any conventional means, such as (without limitation) dots, dimples or notches cut or etched into the metal, or stained with a permanent ink permeating the substrate of the metal. As noted, the point marks 510 are located completely randomly around the outer circumference of the predetermined length L of the tubular W, and there are no upper and lower limits on the number of point marks 510 that may be made.

When the tubular W is rotated fast enough (per arrow 530 on FIG. 33), the point marks begin to appear as "lines" to sensor technology that may be located along the predetermined length L of tubular. The greater the number of point marks 510 made on the tubular W, the greater the number of lines. These lines combine to form a "bar code" along the predetermined length of tubular, illustrated functionally as item 520 on FIG. 33. This bar code 520 may be read by any technology sensitive to the presence of the point marks 510 or the lines comprising the bar code 520. Since the point marks were made on the tubular W on a random basis, the bar code 520 should be random and unique to the tubular W on which it is deployed.

Based on a series of randomly placed point marks 510, this bar code 520 identifier will be less susceptible to degradation or corruption than its predecessors in the prior art. Point marks, by their nature, are less likely to suffer damage from handling or storage. Corrosive or aggressive service is less likely to deteriorate a point mark to the point of eradication. Technologies may be used to make point marks that are unavailable for making more sophisticated and precisely-shaped marks than a simple point. These technologies may make more permanent marks in corrosive or aggressive service.

Additionally, with further reference to FIG. 33, the longer the predetermined length of tubular L over which the point marks 510 are made, and the greater the number of point marks 510 that are randomly made to the outer circumference of the tubular W, the longer the resulting bar code 520 will be when the tubular is rotated, and the more "dense" the lines will be in the bar code 520. Suppose a small number of point marks 510 deteriorate or become corrupted during handling or service. When the bar code 520 is long and highly dense with lines, such bar code is still likely to be unique and traceable to the tubular even though some of the point marks (lines) are missing or have become undetectable.

A further advantage of the DAS is that it is operable on a rotating tubular specimen. It will be appreciated that sensors scanning or sampling a rotating tubular are able to discern characteristics of the tubular that would either be undetectable or poorly detectable on a stationary tubular. For example, without limitation, the following characteristics are detectable (or better detectable) when the tubular is rotating:

(a) Vibrational frequency and amplitude;
    (b) Harmonic response characteristics;
    (c) Torsional displacement in response to torsional load; or
    (d) Responses to sonic, optical or magnetic radiation It will be further appreciated that by rotating the tubular during sensing or sampling, logs over the tubular become available that enable high resolution in pinpointing an item of interest, such as a defect or an anomaly, or a tubular identification or tracking tag. The sensing and sampling then goes well beyond accurate pinpointing, enabling real time qualitative analysis of the item of interest. As noted above, the DAS may obviate current manual electromagnetic and sonic analysis of lengths of tubulars, one-by-one.

Sensors on the DAS are connected to the processing unit by conventional telemetry, such as hard wire cables, wireless telemetry or optical cables. The telemetry selected will depend on environmental conditions such as distance over which telemetry is required, bandwidth and signal interference levels.

As disclosed earlier, the DAS may be embodied on any conventional data acquisition system whose performance matches the needs of the Scorpion System for obtaining, processing, comparing and displaying sensor readings and samples in real time. In a currently preferred embodiment of the DAS, however, the applicable software is advantageously customized to the Scorpion System via conventional programming to achieve the following operational goals and advantages:

(1) Receive and process a high sampling rate from many sensors, so as to effectively sample the tubular in real time with high resolution. Such high resolution comes not only from a high sample rate at each sensor, but also from concurrently processing samples from a high number of sensors.

(2) Display the output in easily-readable graphical formats, with the capability to "drill down" or "magnify" on areas of specific interest. The resolution level is able to support such magnification.

(3) Display the output against user selected paradigm(s) so that differences can be easily identified and characterized. The paradigms have the same resolution as the real time data so that magnification of areas of interest supports a true, full comparison with the paradigm.

(4) Display the output remotely, allowing review of data and comparisons away from the machine. Such remote review may be enabled by transmission of local data to remote terminals, or by linking remote terminals to local terminals via conventional terminal-sharing applications such as GoToMeeting by Citrix.

A paradigm for optimal Scorpion System operating efficiency includes being able to program the ODS to run automatically. That is, to repeat a cycle of tubular exterior processing operations (including cleaning and data acquisition operations) as a series of tubulars are automatically and synchronously: (1) placed into position at the beginning of the cycle, (2) ejected at the end of the cycle, and then (3) replaced to start the next cycle. It may also be advantageous in some embodiments (although the Scorpion System is not limited in this regard) to synchronize ODS and MLI operations. Specifically, embodiments of the electronic control system of the Scorpion System allow users to select a "Dirtiness Factor" for a tubular (or series thereof). The Dirtiness Factor reflects a weighted estimate including an assessment of the severity of the tubular's contamination and the level of clean required by the Scorpion System. All speeds, pressures, distances and other relevant factors for cleaning operations are then automatically generated according to the Dirtiness Factor and fed into the cleaning systems of the Scorpion System. The goal by applying and following the Dirtiness Factor regimen is to clean the tubular 100% to the level selected before cleaning in one pass, without having to return and re-clean. As a result, the Scorpion System's cleaning efficiency with respect to time and quality will be maximized, while still giving the desired level of clean. Similarly, the consumption of consumables such as brushes, liquids, fluids, etc., used in the cleaning process will be minimized, while still giving the desired level of clean.

In automatic mode on the ODS, the user may specify the sequence of ODS operations in a cycle on each tubular. The cycle of ODS operations will then be enabled and controlled automatically, including causing the ODS buggy to travel up and down above a tubular, with corresponding repositioning of ODS buggy (if required) with respect to the tubular. If applicable, the cycle may also include coordinating ODS operations in a cycle with concurrent MLI operations. The cycle may be repeated in automatic mode, as tubulars are sequentially placed into position. In semi-automatic mode, the operation may be less than fully automatic in some way. For example, a cycle may be user-specified to only run once, so that tubulars may be manually replaced between cycles. In manual mode, the user may dictate each ODS operation individually, and the ODS may then pause and wait for further user instruction.

For the avoidance of doubt, a "cycle" as described immediately above may comprise one pass or multiple passes of (1) the ODS, and/or of (2) user-selected lances in the MLI through each tubular, all in order to enable a user-selected sequence of operations. Nothing in this disclosure should be interpreted to limit the Scorpion System in this regard. Further, again for the avoidance of doubt, in a currently preferred embodiment of the Scorpion System, the ODS may run synchronously or asynchronously with some or all of the lances on the MLI, all according to user selection.

Throughout this disclosure, reference has been made to software-driven electronic control systems and data acquisition/processing systems. It will be understood that such systems may be embodied on software executable on conventional computers, networks, peripherals and other data processing hardware.

Also, throughout this disclosure, conventional control, power and hydraulic/pneumatic actuating systems for features and aspects of the disclosed technology have been omitted for clarity. Likewise, conventional support structure for features and aspects of the disclosed technology, such as structural steel, has been omitted for clarity.

Internal Cleaning and Inspection

Reference is now made to FIGS. 14 through 26 and FIGS. 21 through 24 in describing the currently preferred embodiment of the MLI.

It will be understood that the MLI, in a currently preferred embodiment, has a number of cooperating parts and mechanisms, including the Knuckle Jointed Lancer (KJL). FIGS. 14 and 15 are a functional cross-sectional representation of some of the main components included in a currently preferred embodiment of the MLI, and depict how such components cooperate in the MLI assembly. As functional representations, they will be understood not to be to scale even in a general sense. Rather, it will be appreciated that a primary purpose of FIGS. 14 and 15 is to illustrate cooperating aspects of the MLI in a conceptual sense (rather in a more structurally accurate sense), in order to facilitate better understanding of other, more structurally accurate illustrations of the MLI and KJL in this disclosure.

FIG. 14 illustrates MLI assembly 100 generally in cross-section, and depicts MLI assembly as generally comprising guide tube 101, stabbing guide tube 102, Knuckle Jointed Lancer (hereafter "KJL") 103, stinger 104, hose 105, tooling head 106 and stabbing wheels 107. In FIG. 14, MLI assembly is shown operable to clean the internal surface of tubular W. Tubular W is shown on FIG. 14 as longitudinally stationary but rotating, per earlier material in this disclosure.

With further reference to FIG. 14, KJL 103 provides stinger 104 and tooling head 106 at one end. KJL is operable to be "stabbed" into and out of rotating tubular W. It will be understood that by stabbing KJL 103 in and out of the entire internal length of rotating tubular W while tubular W rotates, MLI assembly 100 enables cleaning tools and other functional devices on tooling head 106 (such tools and devices not individually illustrated on FIG. 14) to clean, inspect, sense or otherwise perform work on the entire internal length of tubular W.

Stabbing wheels 107 on FIG. 14 enable KJL 103 to be stabbed in and out of tubular W. It will be appreciated from FIG. 14 that guide tube 101 and stabbing guide 102 generally encase KJL 103 up until the general area where stinger 104 and tooling head 106 lead the "stabbing" (that is, the extension and retraction) of KJL 103 into and out of tubular W. Stabbing guide 102 provides gaps G where the outside surface of KJL 103 is exposed. In a currently preferred embodiment, gaps G are rectangular openings in stabbing guide 102, although this disclosure is not limited in this regard. Directional arrows 108A and 108B on FIG. 14 represent where stabbing wheels 107 are operable to be moved together and apart so that, via gaps G, the circumferences (or "treads") of stabbing wheels 107 can engage and disengage the outer surface of KJL 103 on opposing sides. Thus, when stabbing wheels 107 are engaged on the outer surface of KJL 103 and rotated, per directional arrows 109A and 109B on FIG. 14, they become operable to move KJL 103 per directional arrow 110.

With further reference to FIG. 14, KJL 103 and stinger 104 encase 105. Hose 105 on FIG. 14 is a functional representation of any type of flexible supply that tooling on tooling head 106 may require, such as, purely for example, steam hoses, water hoses, air hoses, nitrogen gas hoses, or conduits comprising electrical power supply cords, data transfer wiring, solid conductors, coils or antennae. Nothing in this disclosure shall be interpreted to limit hose 105 to any particular type of flexible supply or combination thereof.

Discussing hose 105 in more detail, in currently preferred embodiments, the hoses are designed and manufactured for extended life in high temperature and high pressure service, and further comprise a customized armor system for protection on the outside, including an outer co-flex, stainless steel wall with flexible steel armoring and rigidity packing. The rigidity packing uses heat-shrinking material to form a solid ID-OD fusion bond in the hoses, while also filling the void between the outer armor system and the specially-designed high temperature and high pressure hoses. It will be appreciated, however, that these hose specifications are exemplary only, and that nothing in this disclosure should be interpreted to limit hose 105 on FIG. 14 to a particular specification.

It will be further understood that in embodiments where hoses 105 are specified per the example above for extended hose service life, the cost per unit length of the high-specification hose is significantly higher than the corresponding cost of conventional hose. In order to optimize this increased cost, hose 105 on FIG. 14 may, in some alternative embodiments, provide, a connector separating a portion of conventional hose from a portion of higher specification hose. Advantageously, the portion of high-specification hose is positioned within KJL 103 and stinger 104 at the distal end thereof, connected to tooling head 106, and is long enough so that when KJL 103 is extended all the way to the very far (distal) end of tubular W, the entire length of tubular W is served by high-specification hose. The remaining portion of hose 105 will then be understood to be resident in the portion of KJL 103 that remains in guide tube 101 even when KJL 103 is extended all the way to the very far end of tubular W. This remaining portion of hose 105 may be deployed as conventional hose since it is not subject to the rigors of service within tubular W.

Although FIG. 14 illustrates a single hose 105 deployed in KJL 103, it will be appreciated that this disclosure is not limited to any particular number of hoses 105 that may be deployed in a single KJL 103. Multiple hoses 105 may be deployed in a single KJL 103, according to user selection and within the capacity of a particular size of KJL 103 to carry such multiple hoses 105. This "multiple hose 105 per KJL 103" aspect of MLI 100 is described in greater detail further on in this disclosure, with reference to FIG. 14.

With reference now to graphical separator A-A on FIG. 14, it will be appreciated that the portion of KJL 103 to the right of A-A on FIG. 14 is in cross-section, while the portion to the left is not. FIG. 14, to the left of graphical separator A-A, thus illustrates that a portion of the length of KJL 103 comprises a concatenated and articulated series of hollow, generally trapezoidal KJL segments 111. KJL segments 111 (and their generally trapezoidal profile) will be described in detail further on in this disclosure. However, it will be seen from FIG. 14 that the concatenated, articulated nature and general trapezoidal profile of KJL segments 111 allow KJL 103, when the distal end thereof is being stabbed in and out of tubular W, to correspondingly slide around curved portions of guide tube 101 with reduced bending stress.

FIG. 15 is a cross-sectional view as shown on FIG. 14. Items depicted in both FIGS. 14 and 15 have the same numeral.

It will be immediately seen on FIG. 15 that, consistent with earlier material in this disclosure, a preferred embodiment of MLI assembly 100 provides 4 (four) separate and independent lances for cleaning, inspection, data acquisition and related operations (although as noted above, nothing in this disclosure should be construed to limit MLI assembly 100 to four lances). On FIG. 15, stabbing guide 102 includes upper and lower stabbing guide pieces 102U and 102L, which may be held together by conventional fasteners such as bolts and nuts. Stabbing guide 102 further encases 4 (four) separate KJL 103 assemblies. Each KJL 103 encases a hose 105. It will be understood that KJL 103, stinger 104 (not illustrated on FIG. 15), hose 105 and tooling head 106 (also not illustrated on FIG. 15) are functionally the same for each of the 4 (four) lance deployments illustrated on FIG. 15. It will be further appreciated that the disclosure above associated with FIG. 14 directed to extension and retraction of a single KJL 103 applies in analogous fashion to additional KJL assemblies 103 deployed on a particular embodiment of MLI assembly 100.

As also mentioned above with reference to FIG. 14, it will be appreciated that although FIG. 15 illustrates a single hose 105 deployed in each KJL 103, it will be appreciated that this disclosure is not limited to any particular number of hoses 105 that may be deployed in any single KJL 103. Multiple hoses 105 may be deployed in any single KJL 103, according to user selection and within the capacity of a particular size of KJL 103 to carry such multiple hoses 105. This multi-hose 105 and multi-size KJL 103 aspect of MLI 100 is described in greater detail further on in this disclosure, with reference to FIG. 14.

Although not illustrated on FIGS. 14 and 15, currently preferred embodiments of guide tubes 101 and stabbing guide 102 provide a low-friction coating on the internal surface thereof. This low-friction coating assists a sliding movement of KJL 103 through guide tubes 101 and stabbing guide 102 as KJL 103 is extended and retracted into and out of tubular W.

FIG. 15 also shows stabbing wheels 107. Consistent with FIG. 14, directional arrow 108A/B on FIG. 14 represents where stabbing wheels 107 are operable to be moved together and apart so that, via gap G (not shown on FIG. 15), the circumferences (or "treads") of stabbing wheels 107 can engage and disengage the outer surface of KJL 103 on opposing sides. Directional arrows 109A and 109B on FIG. 15 represent, consistent with FIG. 14, that rotation of stabbing wheels 107 when engaged on the outer surface of KJL 103 will cause KJL 103 to extend and retract.

Directional arrow 108C on FIG. 15 represents that when stabbing wheels 107 are disengaged, stabbing guide 102 (or, in other embodiments, stabbing wheels 107) is/are further operable to be moved laterally to bring any available KJL 103, according to user selection, between stabbing wheels 107. In this way, any available KJL 103, according to user selection, may be called up for engagement by stabbing wheels 107 and subsequent extension into and retraction out of tubular W.

Directional arrows H and V on FIG. 15 represent generally that the entire MLI assembly 100 as described on FIGS. 14 and 15 may be adjusted horizontally and vertically to suit size (diameter), wall thickness and relative position of tubular W into which KJL 103 assemblies are to be inserted. Such adjustment allows MLI assembly 100 to work on a wide range of different sizes and thicknesses of tubulars W.

Figure 16:
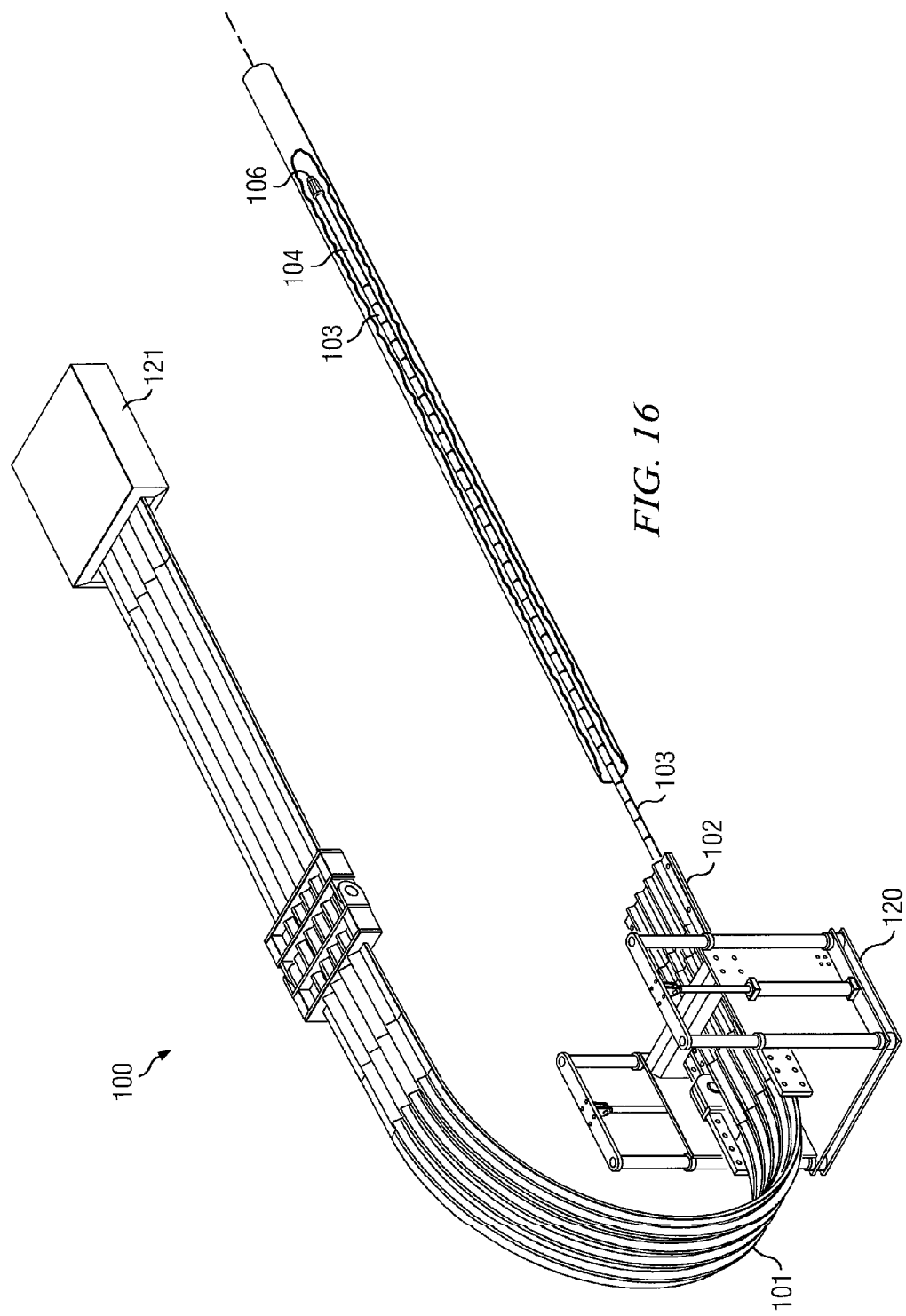
FIG. 16 is an isometric view of aspects of embodiments of the MLI.

With reference now to FIG. 16, a more scale-accurate representation of MLI assembly 100 is illustrated. Items depicted on FIG. 16 that are also depicted on FIGS. 14 and 15 have the same numeral. FIG. 16 depicts tubular W with a partial cutout, allowing KJL 103 (with stinger 104 and tooling head 106 on the distal end of KJL 103) to be seen extending into nearly the entire length of rotating tubular W. FIG. 16 further depicts guide tube 101 and stabbing guide 102.

Adjustment assembly 120 on FIG. 16 enables the positional adjustments described above with reference to FIGS. 14 and 15. More specifically, adjustment assembly 120 includes structure that enables (1) stabbing wheels 107 to move together and apart per directional arrows 108A and 108B on FIGS. 14 and 15, (2) stabbing guide 102 to move laterally per directional arrow 108C on FIG. 15, and (3) MLI assembly 100 to move horizontally and vertically per directional arrows H and V on FIG. 15.

Although adjustment assembly 120 (and components thereof) are illustrated and describe generally in this disclosure, it will be appreciated that the specifics of adjustment assembly 120, and the control thereof, rely on conventional hydraulic, pneumatic or electrical apparatus, much of which has been omitted from this disclosure for clarity.

FIG. 16 further illustrates hose box 121. It will be appreciated that as KJL assemblies 103 are fully extended all the way to the distal end of tubular W, and then retracted all the way out of tubular W, corresponding hoses 105 deployed inside KJL assemblies 103 require surplus length to accommodate such extension and retraction. Hose box 121 is a containment box for such surplus lengths of hoses 105.

Figure 17:
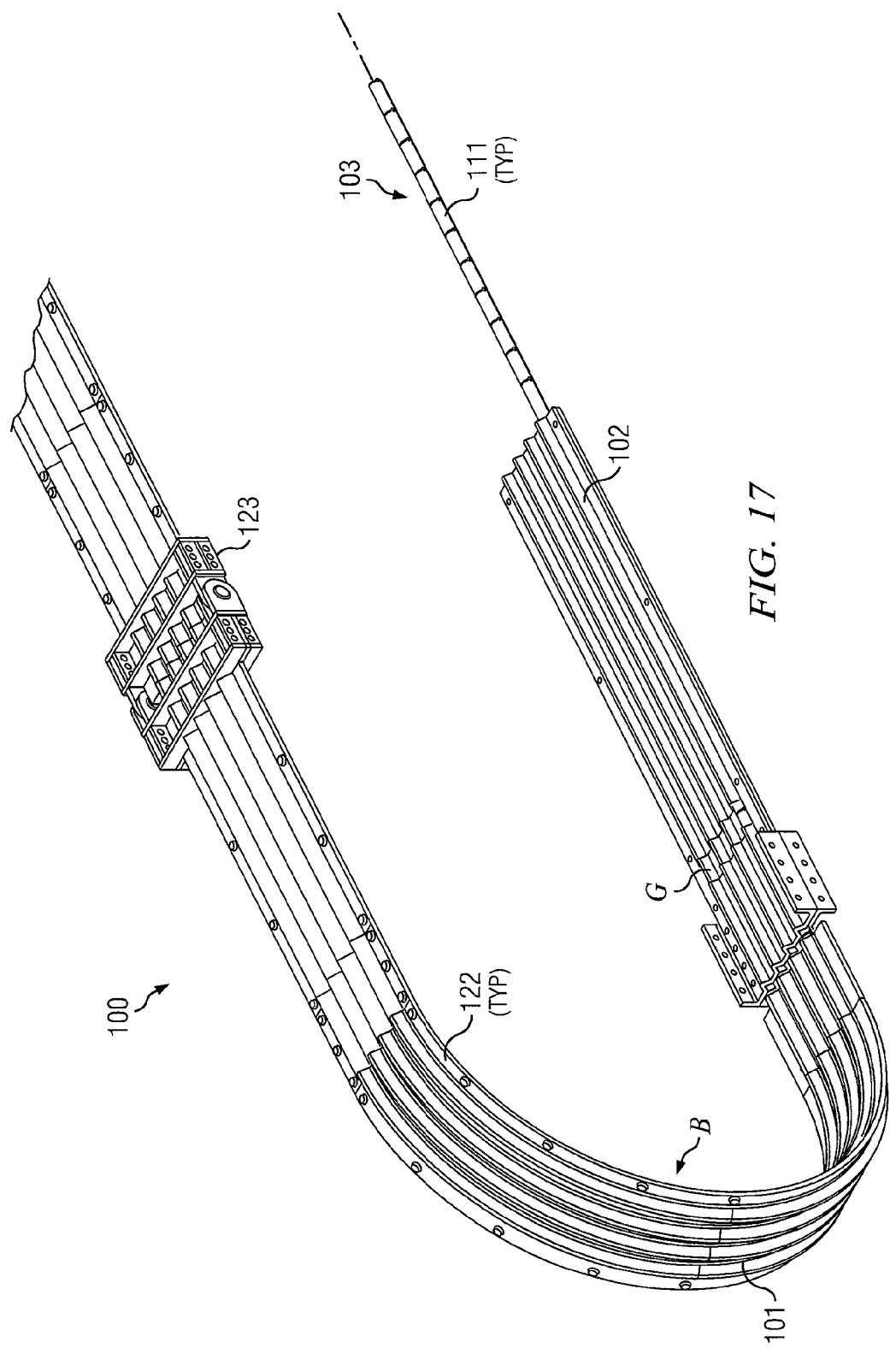
FIG. 17 is a general enlargement of MLI assembly 100 as illustrated on FIG. 16.

FIG. 17 is a general enlargement of MLI assembly 100 as illustrated on FIG. 16, particularly in the area around stabbing guide 102. Adjustment assembly 120 and tubular W on FIG. 16 have been omitted on FIG. 17 for clarity. As in other illustrations in this disclosure depicting aspects of MLI assembly 100, items depicted on FIG. 17 that are also depicted on FIGS. 14, 15 and/or 16 have the same numeral.

FIG. 17 illustrates stabbing guide 102 with one exemplary KJL 103 extended. Gaps G from FIG. 14 can also be seen on stabbing guide 102 on FIG. 17. It will be recalled from earlier disclosure describing FIG. 14 that the "treads" of stabbing wheels 107 (not shown on FIG. 17) contact the outer surface of KJL assemblies 103 through gaps G to enable, via rotation of stabbing wheels 107, extension and/or retraction of KJL assemblies 103.

FIG. 17 further illustrates guide tubes 101 as assemblies operable to be disassembled and reassembled. This aspect of guide tubes 101 enables, in part, MLI assembly 100 to be configured in either "curved tube" mode (as illustrated on FIG. 17) or "straight tube" mode (not illustrated) as further described below. It will be seen on FIG. 17 that in currently preferred embodiments, guide tubes 101 are separable along their travelling horizontal axis (or thereabouts) and are further operably held together during service with guide tube fasteners 122. Longitudinal sections of guide tubes 103 are further separable at guide tubes joints 123 (only one exemplary guide tube joint 123 fully illustrated on FIG. 17).

It will be seen from FIG. 17 that optimization of footprint of MLI assembly 100 may be assisted by deploying guide tubes 101 as illustrated in FIG. 17, with guide tubes 101 undergoing a u-turn of approximately 180 degrees at bend B during their travel. Although also not illustrated in FIG. 17, nothing in this disclosure should be construed to limit bend B to a u-turn of 180 degrees or thereabouts. Other angles of bend B are considered within the scope of this disclosure.

Other embodiments of the MLI assembly 100 (such other embodiments not illustrated) provide guide tubes 101 substantially straight, extending substantially horizontally up to the entrance to tubular W, and substantially parallel to the longitudinal axis of tubular W. It will be appreciated that such "straight tube" embodiments will require additional footprint. Some of such "straight tube" embodiments may also substitute rigid pipes for KJL assemblies 103. With momentary reference to FIG. 14, rigid pipes in "straight tube" embodiments (not illustrated) will surround hoses 105 instead of KJL assemblies 103 and stingers 104, and will further connect directly to tooling heads 106. It will be appreciated that extension and retraction of the rigid pipes may then be enabled via stabbing wheels 107 operating on the exterior surfaces of rigid pipes through gaps G in stabbing guide 102, per FIG. 14).

Figure 18:
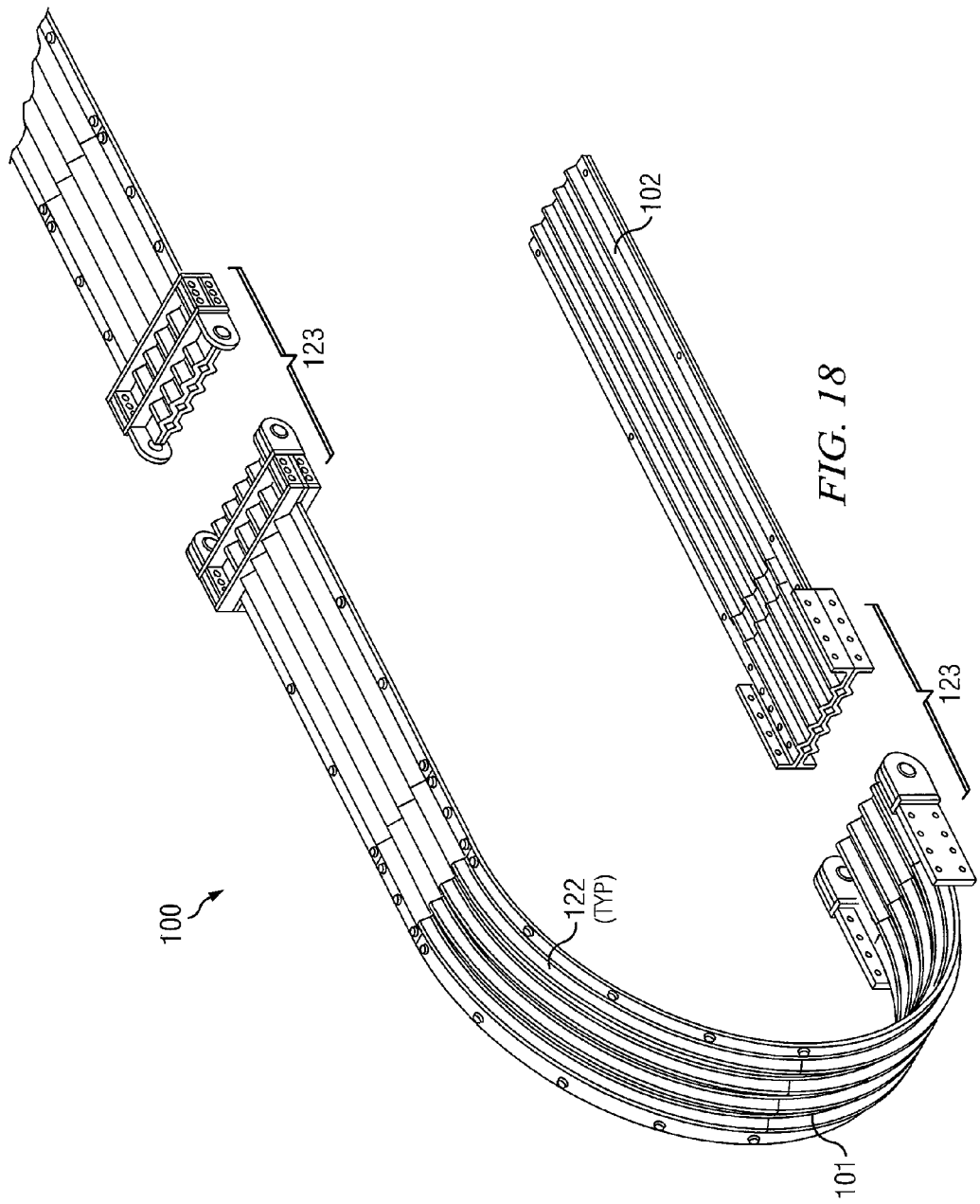
FIGS. 18 and 19 are exploded views of aspects also illustrated on FIG. 17.
Figure 19:
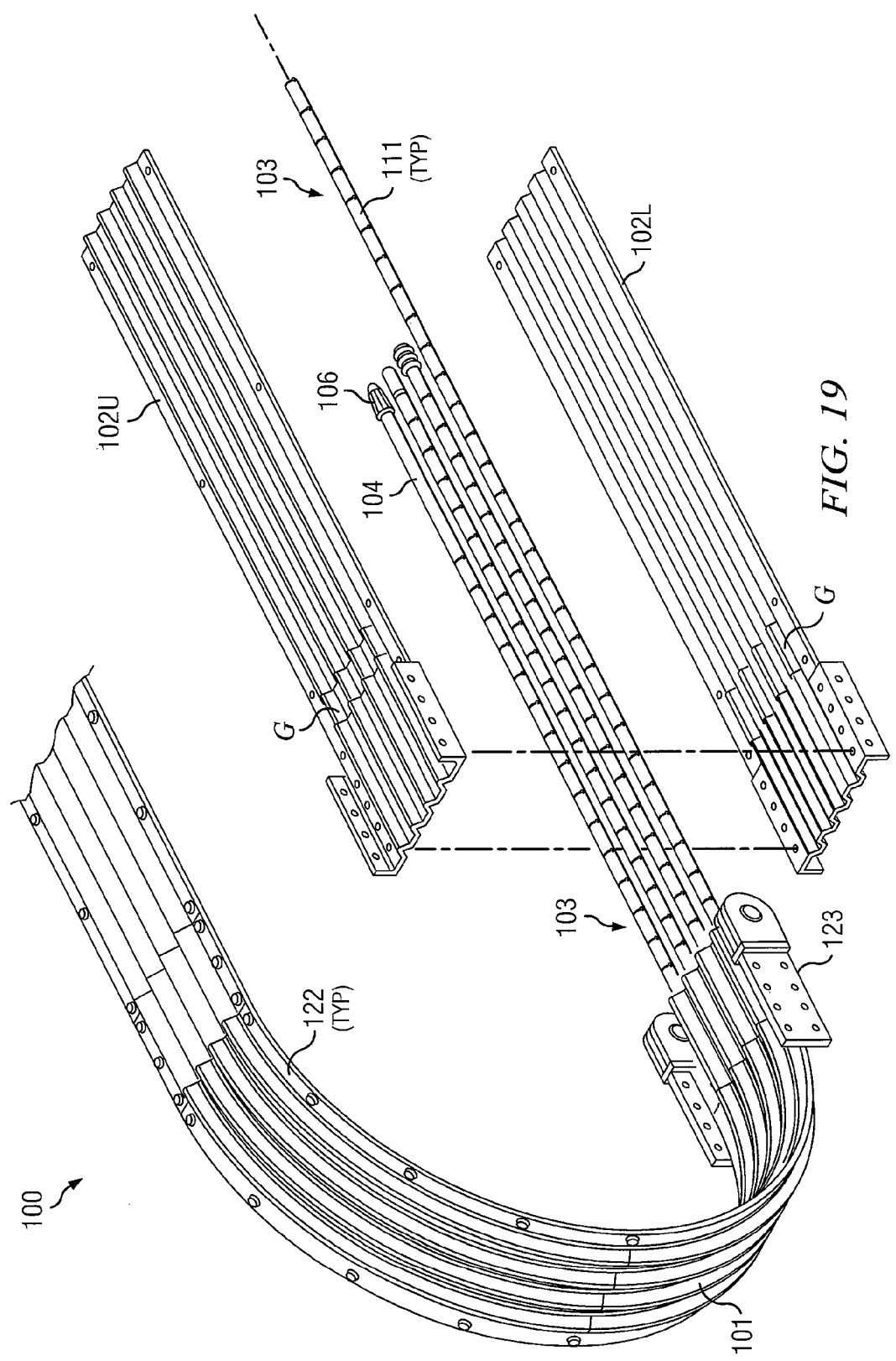

With reference now to FIGS. 18 and 19, guide tubes 101 and stabbing guide 102 are shown in partially "exploded" form in order to illustrate how certain embodiments of MLI assembly 100, now to be illustrated and described in more detail, may be "converted" back and forth, per user selection, between a "curved tube" mode (as illustrated in FIG. 17), and a "straight tube" mode as described above although not illustrated. As before, items depicted on FIGS. 18 and 19 that are also depicted on FIGS. 14 through 17 have the same numeral.

It will be recalled from earlier disclosure referring to FIG. 17 that "convertible" embodiments of MLI assembly 100 provide guide tubes 101 operable to be disassembled and reassembled in order to convert between "curved tube" and "straight tube" modes. FIG. 18 illustrates MLI assembly 100 in "curved tube" mode, with guide tube 101 and stabbing guide 102 disassembled at guide tube joints 123. It will be seen in the exemplary embodiment illustrated on FIG. 18 that two guide tube joints 123 are provided, one at the connection between guide tubes 101 and stabbing guide 102, and the other at a connection between pieces of guide tubes 101 above stabbing guide 102. It will be nonetheless understood that the number and location of guide tube joints 123 illustrated on FIG. 18 are exemplary only. Nothing in this disclosure should be interpreted to limit MLI assembly 101 to any particular number or location of guide tube joints 123.

FIG. 19 illustrates MLI assembly 100 in "curved tube" mode with upper and lower stabbing guide pieces 102U and 102L separated. As noted above with reference to FIG. 17, fasteners 122 may hold sections of guide tube 101 and stabbing guide 102 together at the traveling horizontal axis thereof. In such an embodiment, fasteners 122 may be unfastened in order enable disassembly. It will be appreciated with referenced to FIG. 19 that although not illustrated, sections of guide tubes 101 may also be separated at their traveling horizontal axis by unfastening fasteners 122 in analogous fashion to the manner in which FIG. 19 illustrates stabbing guide pieces 102U and 102L as separated.

By way of reference, with FIG. 19 illustrating stabbing guide pieces 102U and 102L as separated, FIG. 19 further illustrates KJL assemblies 103, stingers 104, tooling heads 106, KJL segments 111 and gaps G in more scale-accurate fashion than on FIGS. 14 and 15, where they were illustrated in more of a functional form.

Visualizing FIGS. 18 and 19 together, therefore, it will be appreciated that by disassembling and separating guide tubes 101 at their traveling horizontal axes per FIG. 19, and by separating pieces thereof at guide tube joints 123 per FIG. 18, guide tubes 101 may be disassembled and removed from MLI assembly 100.

Figure 20:
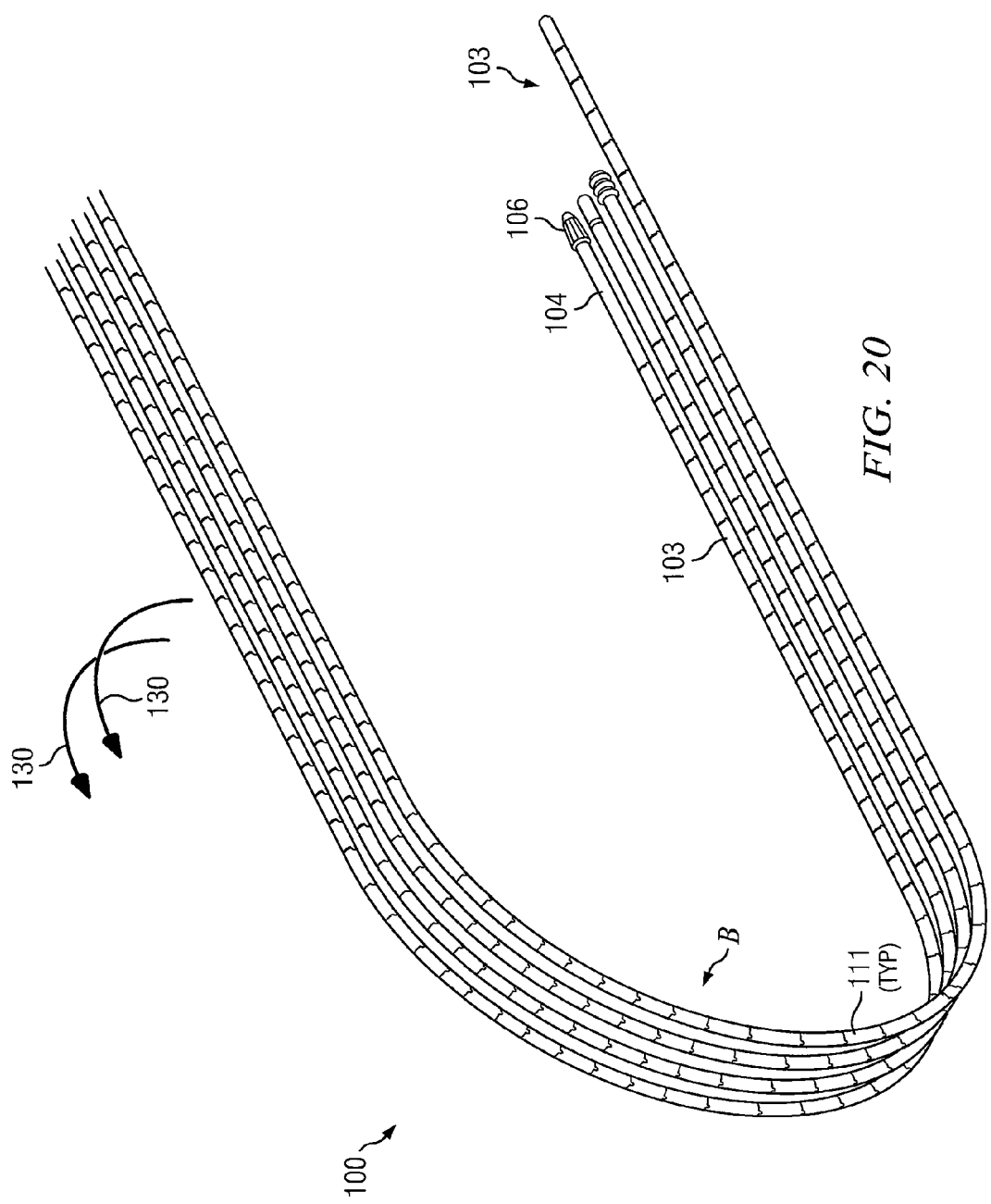
FIG. 20 is an isometric view of aspects of embodiments of KJL assemblies 103 in isolation.

Disassembly and removal of guide tubes 101 in turn exposes KJL assemblies 103 along their entire length, as illustrated on FIG. 20. As before, items depicted on FIG. 20 that are also depicted on FIGS. 14 through 19 have the same numeral. FIG. 20 further illustrates KJL assemblies 103 comprising KJL segments 111. In more detail, it will be recalled from earlier disclosure with reference to FIG. 14 that KJL assemblies 103 each comprise a concatenated and articulated series of hollow, generally trapezoidal KJL segments 111.

Referring back now to the general "conversion" procedure between "curved tube" and "straight tube" modes, it will be appreciated that FIG. 20 illustrates KJL assemblies 103 in "curved tube" mode. It will be further visualized from FIG. 20 that by following directional arrows 130, the articulated, generally trapezoidal nature of concatenated KJL segments 111 enables KJL assemblies 103 to be laid out horizontally straight from their previous "curved tube" configuration (per FIG. 20) once guide tubes 101 are disassembled and removed. It will be then understood that KJL assemblies 103 will be in "straight tube" configuration once laid out straight and horizontal. Rigid pipes (per earlier disclosure) or straight guide tubes in pieces (not illustrated) may then be installed around straight and horizontal KJL assemblies 103. MLI assembly 100 will then be in "straight tube" mode.

It will be appreciated that conversion back to "curved tube" mode requires generally the reverse process. KJL assemblies 103, in straight and horizontal configuration are exposed by removal of their surrounding rigid pipes or straight guide tubes. The articulated, generally trapezoidal nature of concatenated KJL segments 111 enables KJL assemblies 103 to be "rolled over" in the opposite direction of directional arrows 130 on FIG. 20. When "rolled over" to the user-desired bend B (per FIG. 20), KJL assemblies 103 will be in "curved tube" configuration. Guide tubes 101 may be reassembled around KJL assemblies 103 per the reverse of the disassembly process described above with reference to FIGS. 18 and 19. MLI assembly 101 will then be "curved tube" mode again.

FIGS. 21 and 22 illustrate, in conceptual and functional form, the preceding two paragraphs' disclosure of the currently preferred embodiment of "conversion" back and forth, per user selection, of "curved tube" and "straight tube" modes. As before, items on FIGS. 21 and 22 also shown on FIGS. 14 through 20 have the same numeral. On FIG. 21, with further reference to FIG. 20, MLI assembly 100 is in "curved tube" mode with KJL 103 curved around bend B. Stinger 104 and tooling head 106 are shown conceptually on FIGS. 21 and 22 for reference. FIGS. 21 and 22 further show, again conceptually and functionally rather than to scale, that KJL 103 comprises a concatenated string of articulated, generally trapezoidal KJL segments 111.

By following directional arrow 130 on FIG. 21, KJL 103 may be laid out flat and horizontal as shown on FIG. 22. The concatenated string of articulated, generally trapezoidal KJL segments 111 enables KJL to be laid out flat and horizontal, in configuration for "straight tube" mode.

FIG. 22 further shows that by following directional arrow 130R (the reverse of directional arrow 130 on FIG. 21), KJL 103 may be "rolled up" again to form bend B, as shown on FIG. 21. The concatenated string of articulated, generally trapezoidal KJL segments 111 enables KJL 103 to be rolled up, in configuration for "curved tube" mode.

The articulated, generally trapezoidal nature of KJL segments 111 will now be discussed in greater detail. FIG. 23 illustrates a currently preferred design of an individual KJL segment 111. As before, items on FIG. 23 also shown on FIGS. 14 through 22 have the same numeral.

It will be understood that FIG. 23 illustrates just one example of a design of a KJL segment 111. Many types of individual design of KJL segments 111 are available within the scope of this disclosure, and the design of KJL segment 111 on FIG. 23 is exemplary only. Likewise, the size (diameter), number and length of individual KJL segments 111 in a particular KJL 103 may be per user design according to curvature and other geometric parameters of a particular MLI deployment. Nothing in this disclosure should be interpreted to limit the MLI to any particular length, size (diameter), number or even uniformity of KJL segments 111 that may be included in KJL 103.

Referring now to FIG. 23, KJL segment 111 provides pins 139 at one end (one pin hidden from view) and lug holes 140 at the other end. By linking the pins 139 of one KJL segment 111 into the lug holes 140 of the next in line, a plurality of KJL segments 111 may be concatenated into an articulated string, as illustrated in FIGS. 21 and 22, and elsewhere in this disclosure.

KJL segment 111 on FIG. 23 also has opposing longitudinal outer surfaces $111_I$ and $111_O$ which, when a plurality of KJL segments 111 are articulated together into a string thereof, will form the inner and outer surfaces of curvature respectively of the rolled-up articulated string. KJL segment 111 on FIG. 23 further provides opposing faces $111_F$. Opposing faces $111_F$ are configured to slope towards one another. This sloping is illustrated on FIG. 23 at items 141A and 141B, where the planes of faces $111_F$ are illustrated to have angular deviation from a theoretical face plane that would be normal to the longitudinal axis of the KJL segment 111. In this way, the length of KJL segment 111 is less along longitudinal surface $111_I$ than it is along longitudinal surface $111_O$. Accordingly, when a plurality of KJL segments 111 are articulated into a string such that longitudinal surfaces $111_I$ and $111_O$ line up along the string, the shorter lengths of surfaces $111_I$ permit "rolling up" where surfaces $111_I$ form the innermost surface of curvature, and surfaces $111_O$ form the outermost surfaces of curvature.

Figure 24:
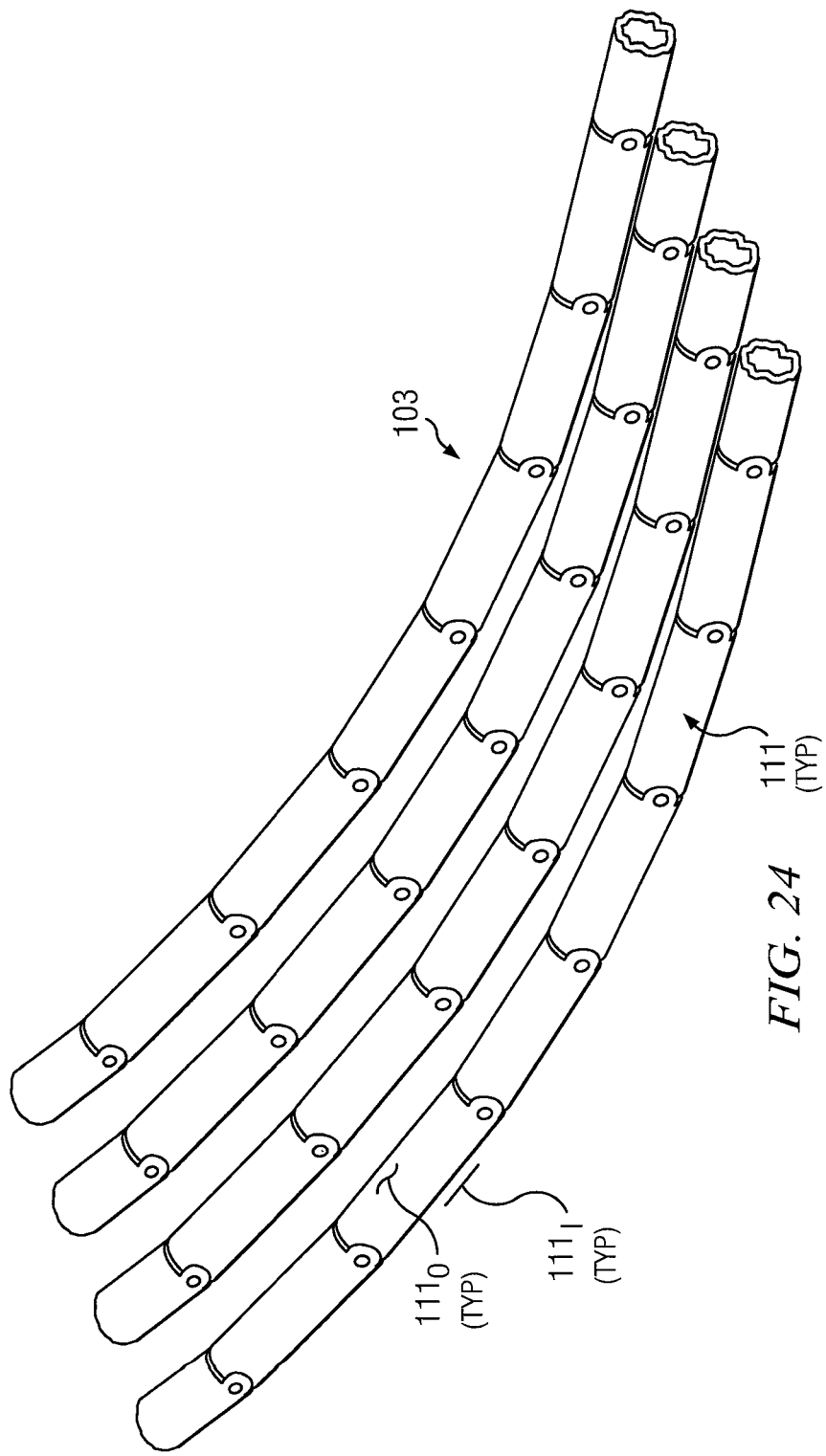

FIG. 24 illustrates KJL 103 comprising a concatenation of articulated KJL segments 111 designed per the example of FIG. 23. As before, items on FIG. 24 that are also shown on FIGS. 14 through 23 have the same numeral.

As described above with reference to FIG. 23, FIG. 24 shows that by linking the pins 139 of one KJL segment 111 into the lug holes 140 of the next in line, a plurality of KJL segments 111 may be concatenated into an articulated string. Further, the shorter lengths of longitudinal surfaces $111_I$ over longitudinal surfaces $111_O$ enable curvature when KJL 103 is "rolled up" so that surfaces $111_I$ form the innermost surface of curvature, and surfaces $111_O$ form the outermost surfaces of curvature.

For the avoidance of doubt, it is important to emphasize that although this disclosure has described immediately above (with reference to FIGS. 18 through 24) the optional feature on some MLI embodiments to "convert" between "curved tube" and "straight tube" modes, this disclosure is not limited to such "convertible" embodiments. Other embodiments may be deployed permanently in "curved tube" or "straight tube" modes.

Figure 25:
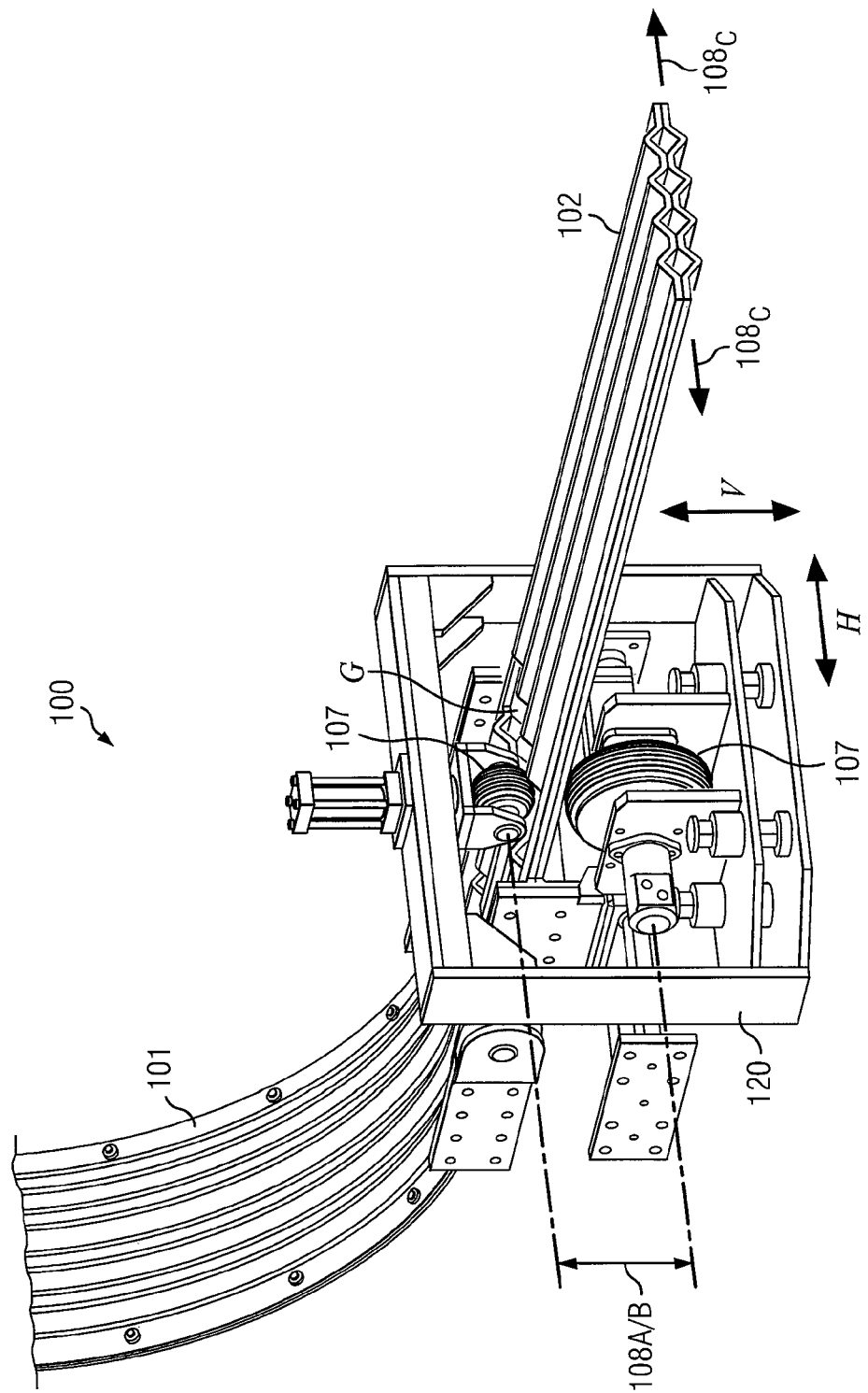
FIGS. 25 and 26 are isometric views illustrating aspects of embodiments of MLI assembly 100 and embodiments of adjustment assembly 120 in more detail.
Figure 26:
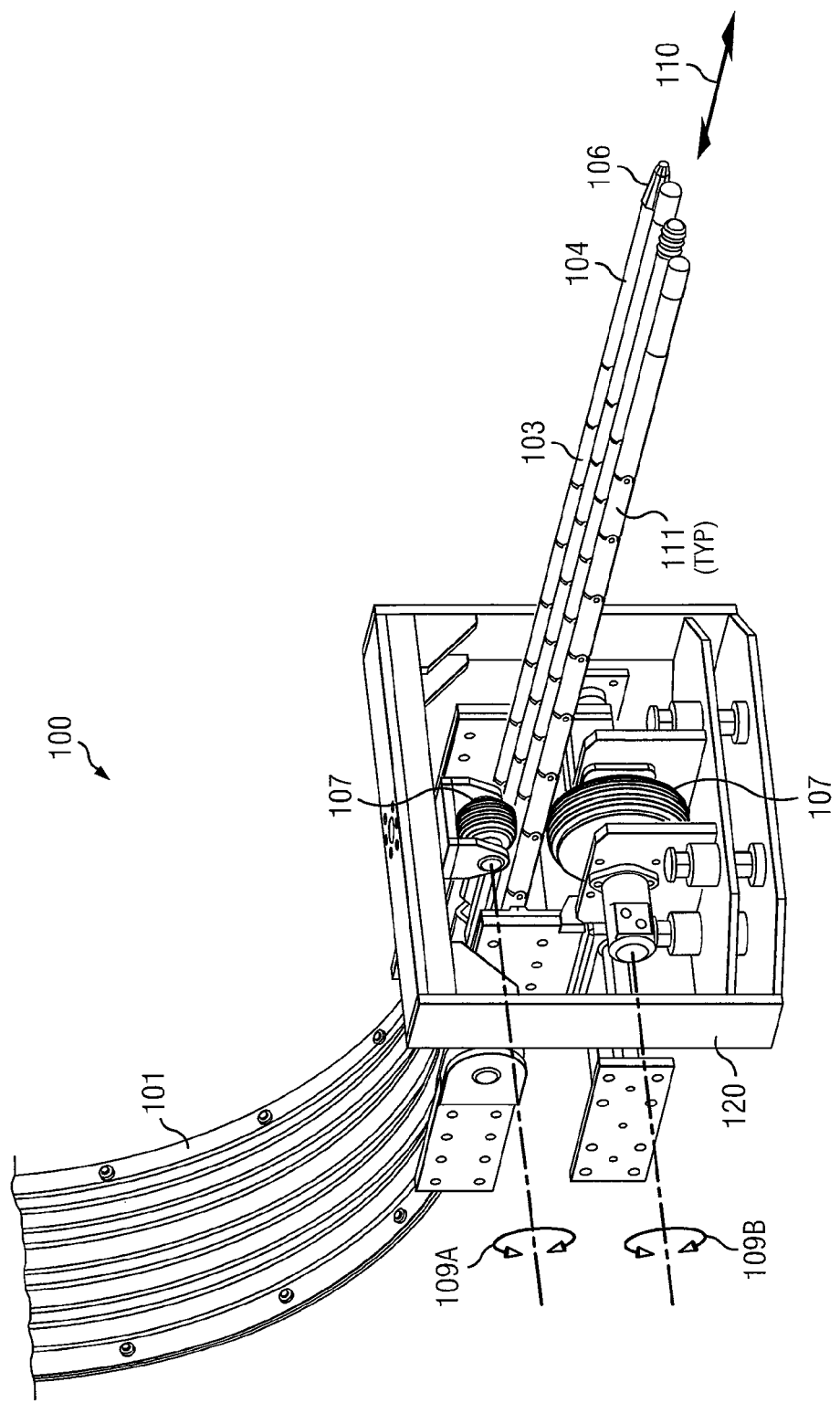

FIGS. 25 and 26 illustrate adjustment assembly 120 (also shown on FIG. 16) in more detail. As before, items shown on FIGS. 25 and 26 that are also shown on any other MLI-series or KJL-series illustration in this disclosure have the same numeral.

The primary difference between FIGS. 25 and 26 is that in FIG. 25, stabbing guide 102 is present, whereas in FIG. 26, it is removed. FIGS. 25 and 26 should be viewed in conjunction with FIGS. 14 and 15.

It will be recalled from earlier disclosure that FIGS. 14 and 15 illustrate, in a functional representation rather that a more scale-accurate representation, the operation of stabbing wheels 107 to enable extension and retraction of KJL 103 into and out of tubular W. FIGS. 14 and 15 further illustrate (again more in a functional sense than in a scale-accurate sense), by means of directional arrows 108A, 108B, 108C, 109A, 109B, 110, H and V, the manner in which stabbing wheels 107 may extend and retract KJL 103, and further, the manner in which MLI 100 may be adjusted positionally (1) to select a particular KJL 103 to be extended and retracted into and out of tubular W, and (2) to set a horizontal and vertical positions of the selected KJL 103 to suit location, diameter and wall thickness of tubular W.

FIGS. 25 and 26 illustrate similar disclosure, except in a more scale-accurate representation, and further with reference to adjustment assembly 120.

Looking first at FIG. 25, it will be seen that adjustment assembly 120 comprises stabbing wheels 107. The "treads" of each stabbing wheel 107 will be understood to be engaged, through gaps G in stabbing guide 102, on the outside surface of KJL 103 (hidden from view by stabbing guide 102). Adjustment assembly 120 may move stabbing wheels 107 together and apart in the direction of arrows 108A/B as shown on FIG. 25 in order to engage/disengage KJL 103 through gaps G. Once stabbing wheels 107 are disengaged, adjustment assembly 120 may also move stabbing guide 102 (and connected guide tubes 101) laterally in the direction of arrow 108C in order to bring a selected KJL 103 into position between stabbing wheels 107 for further extension and retraction operations. Further, adjustment assembly 120 may move the entire MLI assembly 100 in this area in the direction of arrows H and V in order to suit location, diameter and wall thickness of a particular tubular W (not illustrated).

The immediately preceding paragraph disclosed that, in accordance with currently preferred embodiments of adjustment assembly 120, lateral movement of stabbing guide 102 enables a selected KJL 103 to be brought into position between stabbing wheels 107. This disclosure is not limited in this regard, however. Other embodiments of adjustment assembly 120 (not illustrated) may move stabbing wheels 107 laterally, or move both stabbing guide 102 and stabbing wheels 107 laterally, in order to bring a selected KJL 103 into position between stabbing wheels 107.

Turning now to FIG. 26, the "treads" of stabbing wheels 107 may now be seen engaged on the outer surface of KJL 103. Adjustment assembly 120 may cause stabbing wheels 107 to rotate in the direction of arrows 109A and 109B in order to extend and retract KJL 103.

It will be appreciated that, with reference to FIGS. 25 and 26, adjustment assembly 120 may be configured to extend or retract KJL assemblies 103 in a range of sizes. In fact, nothing in this disclosure should be interpreted to limit KJL assemblies 103 (and corresponding KJL segments 111) to any particular size or length. While FIGS. 14 and 15 above illustrate a single hose 105 deployed in each KJL 103, it will be appreciated that this disclosure is not limited to any particular number of hoses 105 that may be deployed in a single KJL 103. Multiple hoses 105 may be deployed in any KJL 103, according to user selection and within the capacity of a particular size of KJL 103 to carry such multiple hoses 105.

Earlier disclosure with reference to FIGS. 14 and 15 described generally the concept that multiple hoses 105 may be deployed in a single KJL 103. The Scorpion System MLI contemplates a wide variety of hoses (and corresponding tooling at the distal end thereof) being available to MLI 100 for internal cleaning, inspection, data acquisition and other operations. Exemplary lances in a preferred embodiment are described above. Hoses suitable to serve such lances include (by way of example only, and without limitation): high volume air hoses for pneumatic tooling; high pressure water; steam; high temperature water; and conduits (e.g. pvc plastic) for data lines, electrical power lines, solid conductors, coils or antennae.

Generally, users are likely to select KJL size (diameter) according to the tooling intended to be deployed at the distal end of the KJL. Multiple hoses carried by a particular KJL will enable deployment of a multi-tool head at the distal end. Alternatively, multiple hoses carried in a particular KJL may be connected and disconnected to suit tooling at the distal end of the KJL as needed.

In addition to number of hoses, users are further generally likely to select KJL size (diameter) according to the size (diameter) of hose(s) intended to be carried Larger size (diameter) hoses may be preferable in long KJL assemblies in order to mitigate pressure loss and/or flow rate loss over the length of the hose. Similarly, larger size (diameter) conduits may be preferable in long KJL assemblies in order to carry larger diameter cables, which are less susceptible to voltage drop, current losses, or signal losses over greater length. Nothing in this disclosure should be interpreted, however, to limit the Scorpion System MLI to such an arrangement. According to user selection and design, a particular deployment of the Scorpion System MLI may have any number of KJL assemblies, in any arrangement of size (diameter) and associated length.

It will be appreciated that when the Scorpion System MLI is configured with a suite of KJL assemblies of differing size (diameter) and corresponding differing KJL segment length, guide tubes 101 and stabbing guide 102 (as illustrated on FIGS. 18 and 19, for example) may become more complex to manufacture, assemble and disassemble.

FIGS. 27 through 30 illustrate various views of Single Lance Reel (SLR) assembly $190_S$ and Multi-Lance Reel (MLR) assembly $190_M$. FIG. 31 illustrates aspects and features of MLR axle assembly $193_M$ on MLR assembly $190_M$ in more detail. As throughout this disclosure, items depicted on FIGS. 27 through 31 that are also depicted on other FIGURES in this disclosure have the same numeral.

Embodiments of the Scorpion System deploying either SLR assembly $190_S$ or MLR assembly $190_M$ on FIGS. 27 through 30 enable concatenated strings of KJL assemblies 103 to be rolled and unrolled, as required, onto or off a rotary "reel"-like assembly as such KJL assemblies 103 are selectably retracted or extended in and out of tubular W. It will be appreciated the primary difference between SLR assembly $190_S$ and MLR assembly $190_M$ is that SLR assembly $190_S$ provides "reel"-like structure for rolling up and unrolling a single KJL assembly 103, while MLR assembly $190_M$ provides "reel"-like structure for rolling up and unrolling multiple KJL assemblies 103 (each KJL assembly 103 capable of being rolled up or unrolled independently per user selection). FIGS. 27 through 31 illustrate embodiments of MLR assembly $190_M$ in which an example of four (4) KJL assemblies 103 are available to be independently rolled up or unrolled. Nothing in this disclosure should be interpreted, however, to limit MLR assembly $190_M$ to handling any particular number (two or more) of KJL assemblies 103.

SLR assembly $190_S$ and MLR assembly $190_M$ are thus alternative embodiments to the earlier described functionality provided by guide tubes 101 (as illustrated on FIGS. 14 through 26). Instead of holding and positioning concatenated strings of KJL assemblies 103 in an encased structure (as in guide tubes 101), SLR assembly $190_S$ and MLR assembly $190_M$ hold and position concatenated strings of KJL assemblies 103 by rolling them up onto a "reel"-like structure. As will be appreciated from FIGS. 27 through 30, therefore, embodiments deploying either SLR assembly $190_S$ or MLR assembly $190_M$ obviate any need for "curved tube" and "straight tube" modes (such as were described above with reference to guide tubes 101). In this way, embodiments deploying either SLR assembly $190_S$ or MLR assembly $190_M$ potentially permit substantial savings in footprint. Such SLR and MLR embodiments further simplify overall deployment of the Scorpion System by obviating the structural steel and other conventional infrastructure that, as described above (although not illustrated for clarity), is required to support and serve guide tubes 101.

Figure 27:
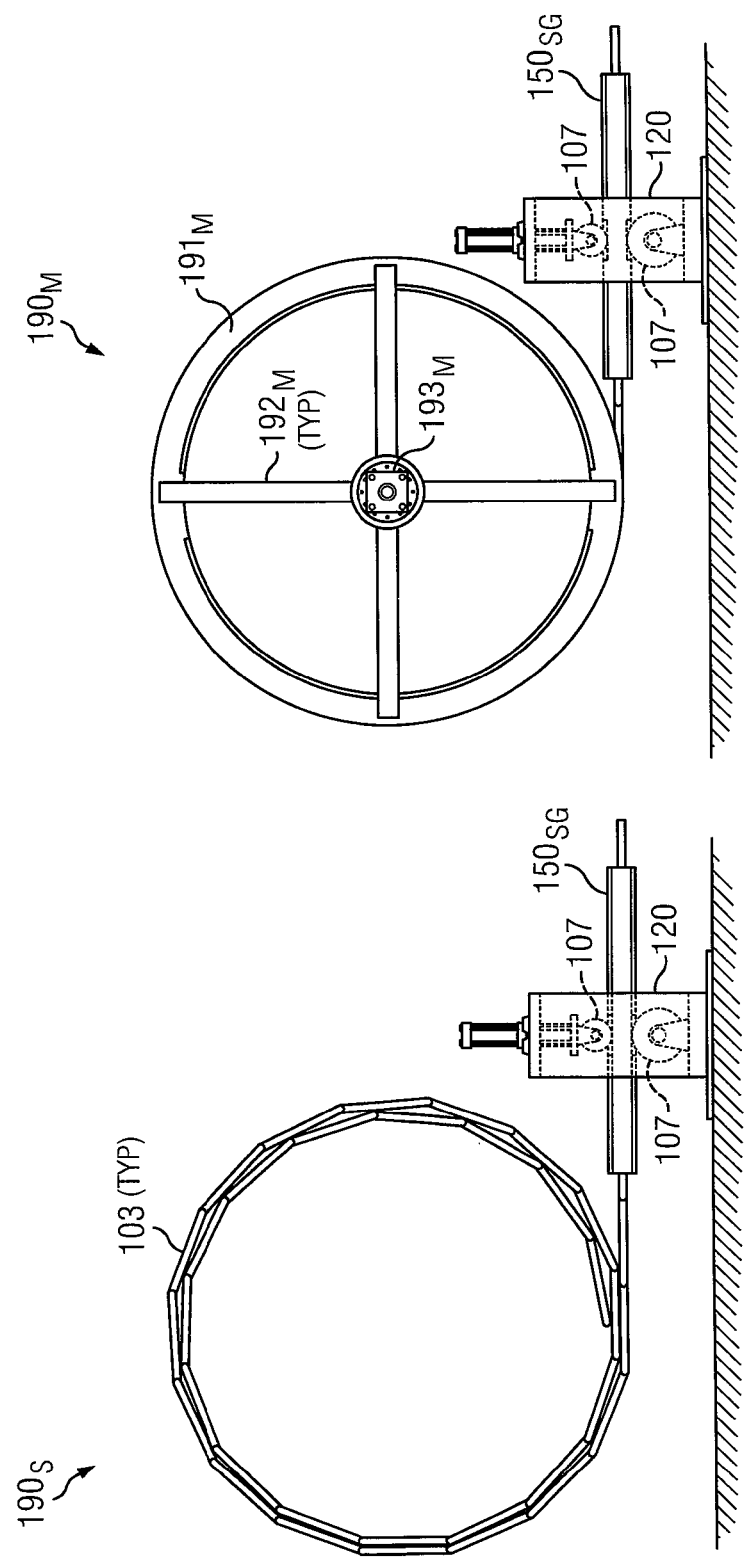
FIG. 27 is an elevation view of embodiments of SLR assembly $190_S$ and MLR assembly $190_M$.

Turning first to FIG. 27, SLR assembly $190_S$ is illustrated with a concatenated string of KJL assemblies 103 substantially fully "rolled up" ready for extension thereof during internal cleaning, inspection or other operations. Substantially all of the structure of SLR assembly $190_S$ has been removed for clarity on FIG. 27 in order to enable better appreciation of the functional operation of SLR assembly $190_S$ (and, by association, MLR assembly $190_M$). The embodiment of SLR assembly $190_S$ illustrated on FIG. 27 further shows stabbing guide $150_{SG}$ and an embodiment of adjustment assembly 120 (including stabbing wheels 107, hidden from view, refer FIGS. 25 and 26) positioned and disposed, per earlier disclosure, to extend and retract the concatenated string of KJL assemblies 103. It will be understood from the embodiment of SLR assembly $190_S$ illustrated on FIG. 27 that as stabbing wheels 107 on adjustment assembly 120 rotate and extend/retract KJL assemblies 103, the "reel"-like structure provided by SLR assembly $190_S$ (omitted for clarity on FIG. 27 but depicted, for example, on FIG. 28) unrolls and rolls up in corresponding fashion to "pay out" and "take up" the concatenated string of KJL assemblies 103.

FIG. 27 further illustrates MLR assembly $190_M$, which, as noted, operates in conceptually and functionally the same manner as SLR assembly 190S to "pay out" and "take up" any one of multiple concatenated strings of KJL assemblies 103 deployed thereon as such KJL assemblies 103 are extended/retracted independently per user selection. The embodiment of MLR assembly $190_M$ depicted on FIG. 27 is hiding the KJL assemblies 103 deployed thereon, but these KJL assemblies 103 may be seen by momentary reference to, for example, the view on FIG. 29. The embodiment of MLR assembly $190_M$ depicted on FIG. 27 illustrates MLR rim $191_M$, MLR spokes $192_M$ and MLR axle assembly $193_M$ in elevation view and in general form.

Figure 28:
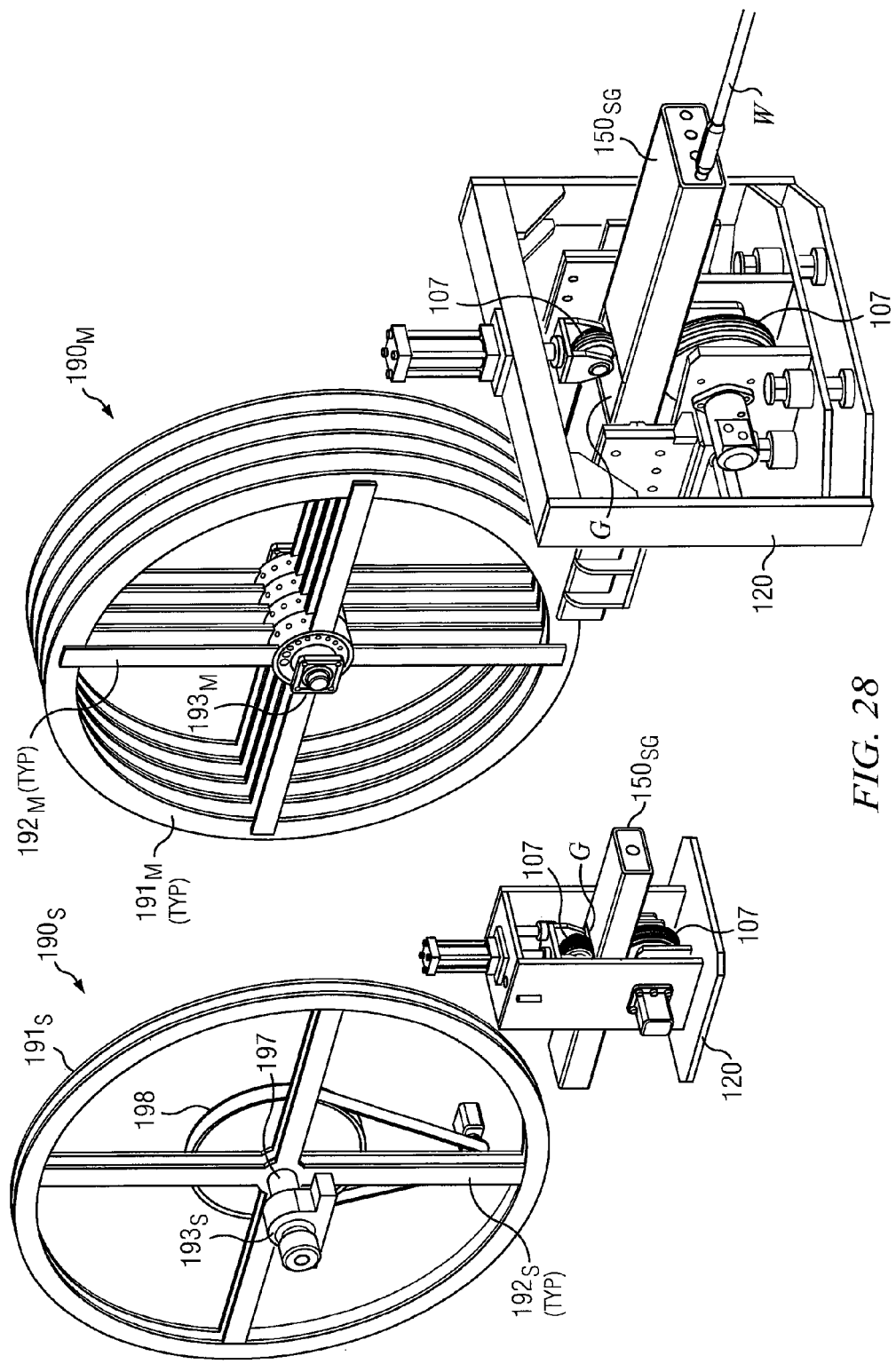
FIGS. 28, 29 and 30 are isometric views of embodiments of SLR assembly $190_S$ and MLR assembly $190_M$.

Reference is now made to FIG. 28, depicting SLR assembly $190_S$ and MLR assembly $190_M$ in a perspective view. KJL assemblies 103 (shown on 29 and 27, for example) have been omitted from SLR assembly $190_S$ and MLR assembly $190_M$ on FIG. 28 for clarity. Among other features, FIG. 28 contrasts the multiple independent reel structure of MLR assembly $190_M$ with the single reel structure of SLR assembly $190_S$. FIG. 28 also illustrates each of MLR assembly $190_M$ and SLR assembly $190_S$ having rims $191_M$ and $191_S$, spokes $192_M$ and $192_S$, and axle assemblies $193_M$ and $193_S$ (which features will be described in more detail further on in this disclosure).

In both MLR assembly $190_M$ and SLR assembly $190_S$ embodiments illustrated on FIG. 28, wheels 107 engage on KJL assemblies 103 via gap G in stabbing guide $150_{SG}$ (KJL assemblies 103 omitted on FIG. 28 for clarity, as noted above). Consistent with earlier disclosure associated with, for example, FIG. 14, rotation of wheels 107 causes KJL assemblies 103 to extend and retract into and out of tubular W. It will be understood from FIG. 27 and now FIG. 28 that as KJL assemblies 103 extend and retract into and out of tubular W, MLR and SLR assemblies $190_M$ and $190_S$ "pay out" and "take up" the concatenated string of KJL assemblies 103 using "reel"-like structure on which KJL assemblies 103 are unrolled and rolled up.

It will be further appreciated with reference to FIG. 28 that on MLR assembly $190_M$, any selected one of the multiple strings of KJL assemblies 103 deployed thereon may be "paid out" and "taken up" independently of the other strings of KJL assemblies 103 also deployed thereon (such non-selected strings of KJL assemblies 103 remaining motionless while the selected one is "paid out" and/or "taken up"). MLR axle assembly $193_M$, in conjunction with MLR rims $191_M$ and MLR spokes $192_M$, provides structure to enable independent "paying out" or "taking up" of any string of KJL assemblies 103 deployed, and will be described in greater detail further on with reference to FIG. 31. This structure on MLR assembly $190_M$ enabling independent "paying out" or "taking up" of any string of KJL assemblies 103 deployed thereon enables MLR assembly $190_M$ to be compatible with earlier disclosure (see FIGS. 14, 15, 25 and 26 and associated disclosure including stabbing wheels 107 and adjustment assembly 120, for example) in which any one of multiple strings of KJL assemblies 103 may be user-selected at any particular time for extension into and retraction out of tubular W. It will be further understood that particularly with regard to MLR assembly $190_M$, as adjustment assembly 120 moves concatenated strings of KJL assemblies 103 from side to side to bring a selected string thereof between stabbing wheels 107, MLR assembly $190_M$ may be disposed to make corresponding lateral movements.

Figure 29:
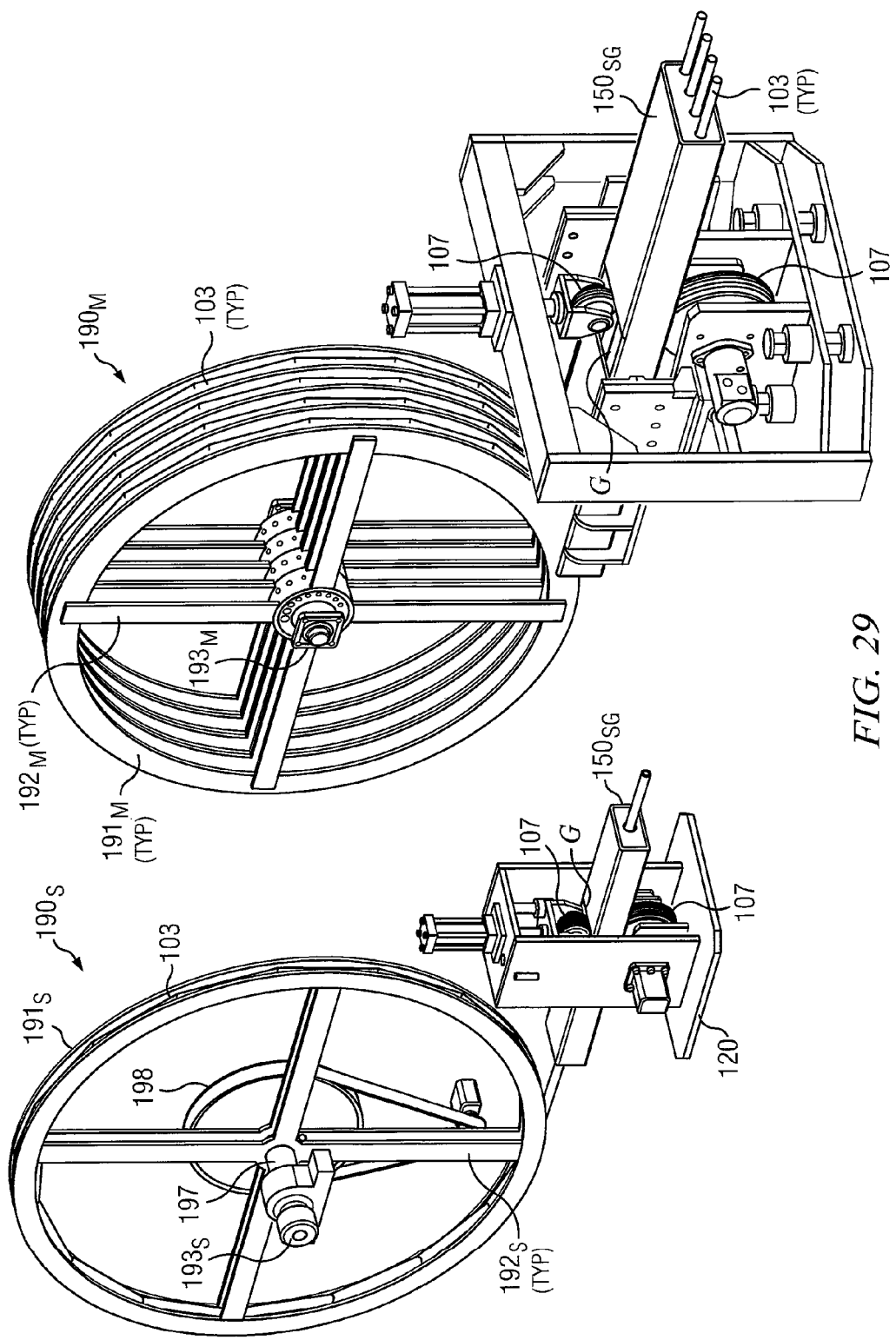

FIG. 29 illustrates MLR and SLR assemblies $190_M$ and $190_S$ in similar fashion to FIG. 28, except FIG. 29 also shows concatenated strings of KJL assemblies 103 deployed on MLR and SLR assemblies $190_M$ and $190_S$ (such strings of KJL assemblies 103 omitted for clarity on FIG. 28). Disclosure above referring to FIGS. 27 and 28 applies equally with reference to FIG. 29.

Figure 30:
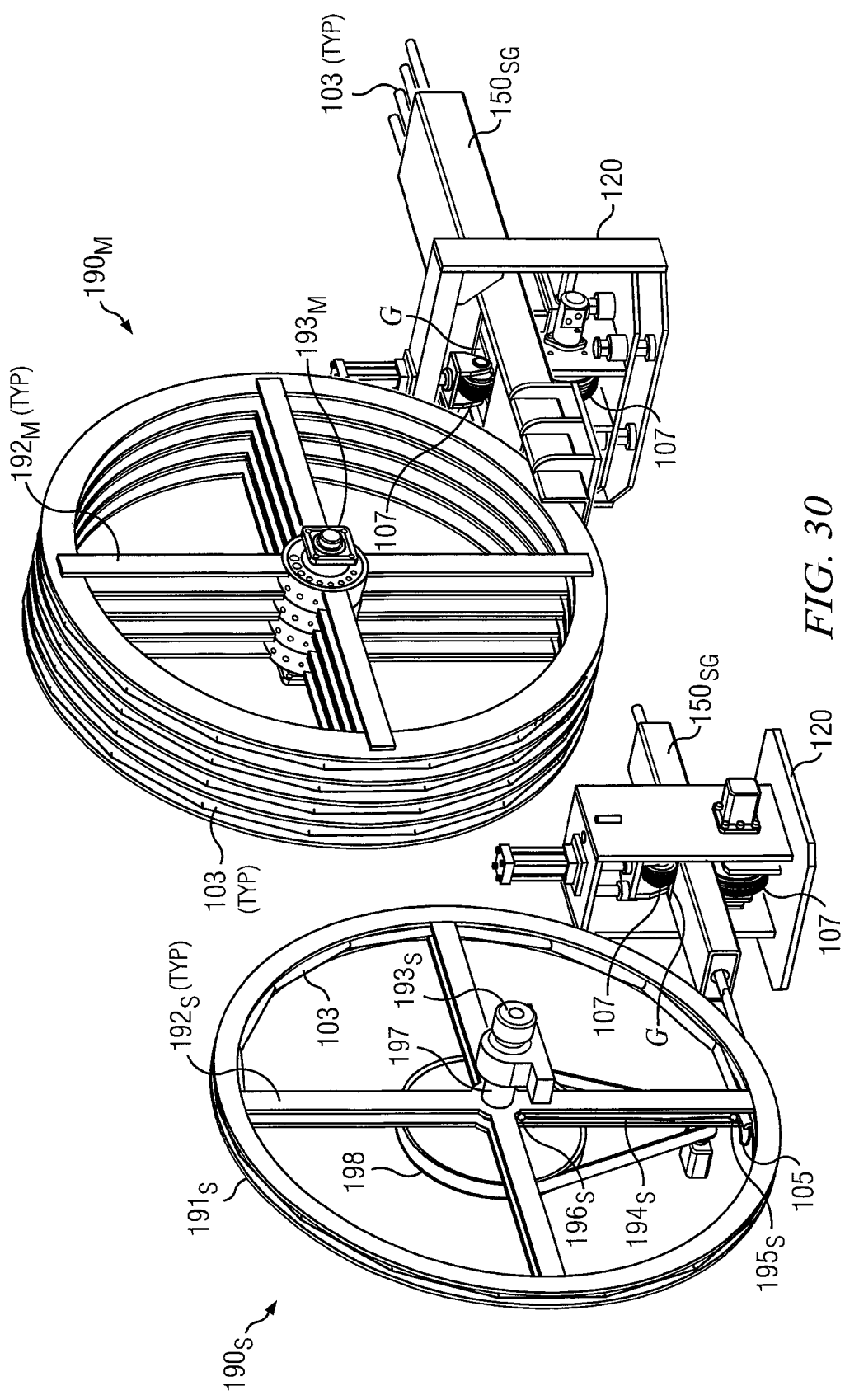

FIG. 30 illustrates MLR and SLR assemblies $190_M$ and $190_S$ in similar fashion to FIG. 29, except shown from a different perspective angle. FIG. 30 further shows SLR assembly $190_S$ with parts of SLR rim $191_S$ removed so that KJL assemblies 103 can be seen more clearly deployed thereon.

The following disclosure regarding deployment of KJL assemblies 103 on SLR rim $191_S$ is also illustrative of corresponding deployment of each of the multiple KJL assemblies 103 acting independently on MLR rims $191_M$, although such structure on MLR rims $191_M$ is hidden from view on FIG. 30. It will be seen on FIG. 30 that the first KJL assembly 103 in the concatenated string thereof is anchored to SLR rim $191_S$ with the distal end of the first KJL assembly 103 near any one of SLR spokes $192_S$. Anchoring may be by any conventional removable anchoring structure, such as threaded bolts, for example, wherein KJL assemblies 103 may be periodically removed from SLR rim $191_S$ for maintenance. In preferred embodiments, SLR rim $191_S$ provides sidewalls whose spacing is selected to be wide enough to enable a string of KJL assemblies 103 to roll up and unroll comfortably between the sidewalls to permit a helical spooling. In this way, unwanted bending, twisting or shear stresses on the couplings between individual KJL assemblies 103 are minimized as strings thereof are rolled up and unrolled. Other embodiments may provide SLR rim $191_S$ to be narrow enough for successive rolls of KJL assemblies 103 to stack vertically on top of each other rather than "sliding down" partially or completely side by side Preferred embodiments of SLR assembly $190_S$ and MLR assembly $190_M$ as illustrated on FIG. 30 are advantageously sized so that approximately two (2) revolutions thereof will extend a string of KJL assemblies 103 from "fully rolled up" to "fully paid out" (and vice versa). Nothing in this disclosure should be interpreted, however, to limit the choice of size of SLR assembly $190_S$ and/or MLR assembly $190_M$ in this regard.

As noted above, it will be understood that, although not fully depicted on FIG. 30 (because MLR rims $191_M$ on MLR assembly $190_M$ are not partially removed on FIG. 30), the preceding disclosure regarding KJL assemblies 103 deployed on SLR assembly $190_S$ as shown on FIG. 30 is illustrative of each of the KJL assemblies 103 deployed on MLR assembly $190_M$.

It will be further recalled from earlier disclosure that in preferred embodiments, KJL assemblies 103 encase at least one hose 105 that serves tooling head 106 on a distal end of each string of KJL assemblies 103. Refer back, for example, to FIG. 14 with associated disclosure herein. Referring now to FIG. 30 again, it will be appreciated that in the illustrated embodiment, hose(s) 105 within KJL assemblies on SLR assembly $190_S$ terminate at SLR rim $191_S$. SLR spoke hose(s) $194_S$ connect to hose(s) 105 at SLR rim hose connection $195_S$ and extend along a selected SLR spoke $192_S$ to SLR axle hose connection $196_S$ near or on SLR axle assembly $193_S$.

It will be further appreciated that preferred embodiments of SLR assembly $190_S$ provide connection structure as described above and illustrated on FIG. 30 (including SLR rim hose connection $195_S$, SLR spoke hose(s) $194_S$ and SLR axle hose connection $196_S$) in order to facilitate maintenance and replacement of hose(s) 105 in KJL assemblies 103. Nothing in this disclosure should be interpreted to limit the type, location or manner of connection of hose(s) 105 across SLR assembly $190_S$ in other embodiments thereof.

With continuing reference to FIG. 30, SLR axle assembly $193_S$ comprises a conventional rotary union 197. A remote source or reservoir of fluids or other material to be carried and ultimately delivered by hose(s) 105 within KJL assemblies 103 may thus be connected to rotary union 197 on SLR axle assembly $193_S$ (such remote source/reservoir and connection omitted on FIG. 30 for clarity). The fluids or other material flow through rotary union 197 and into hose(s) 105 within KJL assemblies 103 via SLR axle hose connection $196_S$, SLR spoke hose(s) $194_S$ and SLR rim hose connection $195_S$.

FIG. 30 further illustrates SLR drive 198 on SLR assembly $190_S$. SLR drive 198 may be any conventional drive mechanism, and this disclosure is not limited in this regard. In presently preferred embodiments of SLR assembly $190_S$, SLR drive 198 is a direct drive.

SLR drive 198 is provided on SLR assembly $190_S$ to cooperate with stabbing wheels 107 in extending and retracting strings of KJL assemblies 103. In preferred embodiments, stabbing wheels 107 are the primary extending and retraction mechanism (see, for example, FIG. 14 and associated disclosure above). In embodiments deploying SLR assembly $190_S$, however, SLR drive 198 assists stabbing wheels 107 to keep mild tension in strings of KJL assemblies 103 as they are "rolled up" and "paid out". SLR drive 198 may also provide additional power to assist stabbing wheels 107 with extension and retraction of KJL assemblies 103 when required.

It will be recalled from earlier disclosure that FIG. 30 shows SLR assembly $190_S$ with parts of SLR rim $191_S$ removed so that KJL assemblies 103, hose(s) 105 and associated structure can be seen more clearly deployed thereon. The preceding disclosure regarding deployment of KJL assemblies 103 on SLR rim $191_S$ and the structure connecting hose(s) 105 to SLR axle assembly $193_S$ is also illustrative of corresponding deployment of each of the multiple KJL assemblies 103 and associated hoses 105 acting independently on MLR rims $191_M$, although such structure on MLR rims $191_M$ is hidden from view on FIG. 30. In preferred embodiments of MLR assembly $190_M$, although not specifically illustrated, each string of KJL assemblies 103 terminates near a selected MLR spoke $192_M$. Although again hidden from view, it will be understood that hose(s) 105 deployed within each string of KJL assemblies 103 are advantageously connected to MLR axle assembly $193_M$ via MLR rim hose connections, MLR spoke hoses and MLR axle hose connection.

It will be further appreciated that, consistent with similar disclosure with respect to SLR assembly $190_S$ above, preferred embodiments of MLR assembly $190_M$ provide connection structure as described immediately above (including MLR rim hose connections, MLR spoke hoses and MLR axle hose connection identified above but hidden from view on FIG. 30) in order to facilitate maintenance and replacement of hose(s) 105 in KJL assemblies 103. Nothing in this disclosure should be interpreted to limit the type, location or manner of connection of hose(s) 105 across MLR assembly $190_M$ in other embodiments thereof.

FIG. 31 illustrates features and components of an embodiment of MLR axle assembly $193_M$ in more detail. By way of background, it will be appreciated from earlier disclosure that on MLR assembly $190_M$, each string of KJL assemblies 103 deployed thereon is free to be "paid out" or "taken up" independently according to user selection. It will be further recalled that in preferred embodiments (as illustrated on FIG. 30, for example) four (4) independent strings of KJL assemblies 103 are deployed on a single MLR assembly $190_M$. A conventional rotary union, such as rotary union 197 disclosed above on SLR axle assembly $193_S$, is thus not operable for analogous deployment on MLR axle assembly $193_M$, since up to four (4) independent supplies of fluids or other materials need to be carried independently and separately from their respective remote sources or reservoirs via MLR axle assembly $193_M$ to a corresponding hose 105 within one of the independently extensible/retractable strings of KJL assemblies 103 deployed on MLR assembly $190_M$. A conventional rotary union will typically provide structure for only a single supply of fluid through the union.

FIG. 31 illustrates aspects of MLR axle assembly $193_M$ in which, consistent with preferred embodiments illustrated elsewhere in this disclosure, four (4) separate and independent supplies of fluids or other materials may be carried through MLR axle assembly $193_M$. As noted earlier, this disclosure's example to illustrate and describe MLR assembly $190_M$ (and associated MLR axle assembly $193_M$) as providing four (4) separate and independent supplies of fluids or other materials to each of four (4) independently-operable strings of KJL assemblies 103 is an exemplary embodiment only. Nothing in this disclosure should be interpreted to limit MLR assembly $190_M$ (and MLR axle assembly $193_M$) to provide for more or fewer than four (4) separate and independently-operable strings of KJL assemblies 103.

With continuing reference to FIG. 31, MLR axle assembly $193_M$ comprises stationary axle 161, on which four (4) axle spools $162_A$, $162_B$, $162_C$ and $162_D$ are separated by spool seals 163. Spool seals 163 may be any suitable seal between independently rotating parts, such as conventional swivel seals, and this disclosure is not limited in this regard. Axle spools $162_A$, $162_B$, $162_C$ and $162_D$ are each free to rotate separately and independently on axle 161. Viewing FIGS. 27 and 31 together, it will be appreciated that MLR spokes $192_M$ on FIG. 27 advantageously attach to MLR axle assembly $193_M$ via bolting or other similar conventional means to axle spools $162_A$, $162_B$, $162_C$ and $162_D$, as illustrated on FIG. 31.

Referring again to FIG. 31, axle 161 further comprises inlet ports $164_A$ and $164_E$ at one end, and inlet ports $164_C$ and $164_D$ at the other end. Axle spools $162_A$, $162_B$, $162_C$ and $162_D$ each provide a corresponding outlet port $165_A$, $165_B$, $165_C$ and $165_D$. Inlet ports $164_A$ through $164_D$ each connect to a corresponding one of outlet ports $165_A$ through $165_D$ via individual and separate pathways through the interior of axle 161 and axle spools $162_A$ through $162_D$, respectively (such pathways not illustrated). Such pathways may be of any convenient conventional design, such as drilling out each pathway in the core of axle 161 beginning at an inlet port $164_A$ through $164_D$, and emerging in a radial direction at the circumference of axle 161 in line with the circumference of rotation above of the corresponding outlet port $165_A$ through $165_D$ on axle spools $162_A$ through $162_D$. Each axle spool $162_A$ through $162_D$ may then provide a semi-circular (or other shaped profile) groove on its internal circumference in line with its corresponding outlet port $165_A$ through $165_D$, and to which groove each corresponding outlet port $165_A$ through $165_D$ is connected. Such connection may, in some embodiments, include a semi-circular (or other shaped profile) annular groove around the outer circumference of axle 161 that coincides with the grooves on the internal circumference of axle spools $162_A$ through $162_D$ under outlet ports $165_A$ through $165_D$. In such embodiments, the grooves on each surface (outer surface of axle 161 and internal surface of axle spools $162_A$ through $162_D$) may combine to form a ring groove as part of the flow passageway between inlet ports $164_A$ through $164_D$ and corresponding outlet ports $165_A$ through $165_D$. Rotary seals may be provided between axle 161 and axle spools $162_A$ through $162_D$ either side of the groove. In this way, fluids or other material may enter into a selected one of inlet ports $164_A$ through $164_D$ and exit out of a corresponding one of outlet ports $165_A$ through $165_D$, via its drilled pathway in axle 161 and the sealed rotating groove under the corresponding one of axle spools $162_A$ through $162_D$. Preferred embodiments may advantageously hold and pass fluids or other materials in and through the immediately foregoing pathway structure at pressures up to 20 kpsi.

With reference now to FIGS. 27 and 30 and associated disclosure above, and with continuing reference to FIG. 31, it will be appreciated that outlet ports $165_A$ through $165_D$ may be connected to hose(s) 105 deployed within each string of KJL assemblies 103 deployed on MLR assembly $190_M$ via MLR axle hose connections, MLR spoke hoses and MLR rim hose connections (such connection structure hidden from view on FIGS. 27 and 30, but analogous to SLR axle hose connection $196_S$, SLR spoke hose $194_S$ and SLR rim hose connection $195_S$ illustrated and described above with respect to SLR assembly $190_S$ on FIG. 30). It will the therefore understood from the foregoing disclosure that each hose 105 deployed within each independently extendable and retractable string of KJL assemblies 103 deployed on MLR assembly $190_M$ may be addressed and supplied with fluid (or other materials) via a corresponding designated stationary inlet port $164_A$ through $164_D$ located on axle 161.

In exemplary embodiments, the drive structure on MLR assembly $190_M$ provides separate and independently operable drives, such as conventional chain and sprocket drives or belt and pulley drives, to rotate each MLR rim $191_M$ independently, in order to enable each corresponding string of KJL assemblies 103 to be extended or retracted independently, per user selection. It will be appreciated from the structure of MLR axle assembly $193_M$ as illustrated on FIG. 31 that direct drive structure (such as suggested above for SLR drive 198 in preferred embodiments of SLR assembly $190_S$ as illustrated on FIG. 30) is not optimal to provide independent drive structure to at least interior spools $162_B$ and $162_C$. Conventional belt or chain drives are more suitable to drive at least interior spools $162_B$ and $162_C$. Some embodiments of MLR $190_M$ may provide direct drive structure to drive end spools $162_A$ and $162_D$ on MLR axle assembly $193_M$, while other embodiment may provide other conventional drives, such as belt or chain drives, on end spools $162_A$ and $162_D$.

For the avoidance of doubt, it will be understood that throughout this disclosure, certain conventional structure has been omitted for clarity. For example, and without limitation, features of MLI assembly 100 are, in either "curved tube" or "straight tube" mode, advantageously supported by structural steel and other conventional support means, all of which has been omitted for clarity. Operation of MLI assembly 100 (including at adjustment assembly 120) is advantageously accomplished using conventional hydraulic, pneumatic or electrical apparatus, all of which has been also omitted for clarity.

Currently preferred embodiments of MLI assembly 100 may further be controlled to operate in user-selected options of manual, semi-automatic and automatic modes. A paradigm for optimal Scorpion System operating efficiency includes being able to program the MLI to run automatically. That is, to repeat a cycle of tubular interior processing operations (including cleaning and data acquisition operations) as a series of tubulars W are automatically and synchronously: (1) placed into position at the beginning of the cycle, (2) ejected at the end of the cycle, and then (3) replaced to start the next cycle. In automatic mode, the user may specify the sequence of operations of KJL assemblies 103 in a cycle on each tubular W. The cycle of lance operations will then be enabled and controlled automatically, including insertion and retraction of KJL assemblies 103 in sequence in and out of the tubular W, with corresponding repositioning of guide tubes 101 and stabbing guide 102 with respect to tubular W between each lance operation. The cycle may be repeated in automatic mode, as tubulars W are sequentially placed into position. In semi-automatic mode, the operation may be less than fully automatic in some way. For example, a cycle may be user-specified to only run once, so that tubulars W may be manually replaced between cycles. In manual mode, the user may dictate each lance operation individually, and the MLI may wait for further instruction after each lance operation.

Although the present invention and its advantages have been described in detail, it should be understood that various changes, substitutions and alternations can be made herein without departing from the spirit and scope of the invention as defined by the appended claims.

We claim:

1. A Data Acquisition System for determining the state of a tubular, the tubular having a substantially cylindrical shape with a longitudinal axis, internal and external diameters, internal and external cylindrical surfaces, and a length between first and second ends, the tubular further disposed to rotate about its longitudinal axis, the Data Acquisition System comprising: a buggy configured to travel parallel to the longitudinal axis of the tubular; a line scan camera mounted on the buggy and generally pointed at the external cylindrical surface of the tubular, wherein the line scan camera has a field of view observing at least a partial external slice of the tubular as the tubular rotates, wherein the partial external slice includes a view of the external cylindrical surface of the tubular that observes at least one external longitudinal edge of the tubular, the line scan camera further disposed to generate a plurality of pixelated line scan images, such that each pixelated line scan image is disposed to identify the at least one external longitudinal edge of the of the tubular via differentiation between (a) material pixels that depict the tubular and (b) non-material pixels that do not depict the tubular; a range finding laser also mounted on the buggy and pointed at the external cylindrical surface of the tubular, the laser disposed to generate a plurality of laser samples as the buggy travels, each laser sample representing a measured distance from the laser to the external surface of the tubular; the line scan camera and laser in combination disposed to generate a plurality of external diameter samples as the buggy travels, each external diameter sample including (1) a representation of the percentage of material pixels among total material plus non-material pixels for a line scan image generated at a corresponding sampled location along the length of the tubular and (2) a camera distance from the line scan camera to the tubular at the sampled location wherein the camera distance is determined from selected ones of the laser samples; and a data processor receiving rotational information regarding the tubular's rotation, the rotational information comprising the absolute position of a known reference point on the tubular at a particular moment in time together with the rotational speed of the tubular at such moment, the data processor further configured to process at least some of the external diameter samples in association with the rotational information in order to map external diameter variation data over a corresponding portion of the external cylindrical surface of the tubular.

2. The Data Acquisition System of claim 1, in which the data processor is further configured to process at least some of the external diameter samples in association with selected ones of the laser samples in order to enhance the external diameter variation data with corresponding tubular external surface contour variation data.

3. The Data Acquisition System of claim 1, in which:
(a) the data processor also receives tool parameter information, the tool parameter information comprising a set of adjustable tool parameters, each adjustable tool parameter in the set thereof corresponding to a present state of an adjustable feature on at least one tool also mounted on the buggy and disposed to operate on the external cylindrical surface of the tubular;
(b) the data processor is further configured to control adjustment of tool parameters within the set thereof in response to laser samples, and
(c) the adjustment of tool parameters by the data processor causes corresponding adjustment of tool features.

4. The Data Acquisition System of claim 1, in which the data processor is further configured to process at least some of the plurality of laser samples in association with the rotational information in order to map tubular straightness variation data over a corresponding portion of the external cylindrical surface of the tubular.

5. The Data Acquisition System of claim 1, in which the data processor is further configured to process at least some of the external diameter samples in association with the rotational information in order to map tabular straightness variation data over a corresponding portion of the external cylindrical surface of the tubular.

6. The Data Acquisition System of claim 1, further comprising at least one additional fixed range finding laser pointed at the external cylindrical surface of the tabular and mounted at a preselected location along the length of the tabular between the first and second ends, each fixed laser disposed to combine with the laser mounted on the buggy to form a caliper pair thereof, each caliper pair disposed to measure caliper data, the caliper data comprising laser samples taken by both the fixed laser and the buggy-mounted laser at the preselected location at which the fixed laser is mounted, the data processor further configured to process the caliper data to generate tubular external diameter data at the preselected location at which the fixed laser mounted.

7. The Data Acquisition System of claim 6, in which the data processor is further configured to process the caliper data to generate tubular out-of-round data at the preselected location at which the fixed laser is mounted.

8. The Data Acquisition System of claim 1 in which the data processor processes selected ones of the laser samples in association with corresponding rotational information in real time.

9. The Data Acquisition System of claim 1 in which the data processor is further configured to process at least some of the plurality of laser samples in order to identify the first and second ends along the length of the tubular.

10. The Data Acquisition System of claim 1 in which the data processor is further configured to display selected ones of the laser samples in association with corresponding rotational information using visual media.

11. The Data Acquisition System of claim 10, in which the visual media comprise at least one format selected from the group consisting of:
(a) a graph; and
(b) a user-magnifiable data representation whose level of data detail varies with magnification; and
(c) a Gaussian swath displaying measured temperature variations as different colors.

12. The Data Acquisition System of claim 1 in which the data processor is further configured to generate a data signature of the tubular from at least some of the laser samples processed in association with corresponding rotational information.

13. The Data Acquisition System of claim 12, in which the data processor is further configured to generate at least one outcome selected from the group consisting of:
(a) a comparison of the data signature with earlier date signatures of the tubular;
(b) a comparison of the data signature with a standard data signature representing a reference paradigm; and
(c) a unique identifier of the tubular based at least in part on the data signature.

14. The Data Acquisition System of claim 1 in which the data processor further generates a machine-readable rotational bar code from at least some of the laser samples processed in association with corresponding rotational information, and in which the machine-readable rotational bar code comprises a data signature of the tubular.

15. A Data Acquisition System for determining the state of a tubular, the tubular having a substantially cylindrical shape with a longitudinal axis, internal and external diameters, internal and external cylindrical surfaces, and a length between first and second ends, the tubular further disposed to rotate about its longitudinal axis, the Data Acquisition System comprising: a buggy configured to travel parallel to the longitudinal axis of the tubular; a line scan camera mounted on the buggy and generally pointed at the external cylindrical surface of the tubular, wherein the line scan camera has a field of view observing at least a partial external slice of the tubular as the tubular rotates, wherein the partial external slice includes a view of the external cylindrical surface of the tubular that observes at least one external longitudinal edge of the tubular, the line scan camera further disposed to generate a plurality of pixelated line scan images, such that each pixelated line scan image is disposed to identify the at least one external longitudinal edge of the of the tubular via differentiation between (a) material pixels that depict the tubular and (b) non-material pixels that do not depict the tubular; a range finding laser also mounted on the buggy and pointed at the external cylindrical surface of the tubular, the laser disposed to generate a plurality of laser samples as the buggy travels, each laser sample representing a measured distance from the laser to the external surface of the tubular; the line scan camera and laser in combination disposed to generate a plurality of external diameter samples as the buggy travels, each external diameter sample including (1) a representation of the percentage of material pixels among total material plus non-material pixels for a line scan image generated at a corresponding sampled location along the length of the tubular and (2) a camera distance from the line scan camera to the tubular at the sampled location wherein the camera distance is determined from selected ones of the laser samples; a thermal imaging camera mounted on the buggy and pointed at the external cylindrical surface of the tubular, the thermal imaging camera disposed to generate a plurality of thermal image as the buggy travels; and a data processor receiving rotational information regarding the tubular's rotation, the rotational information comprising the absolute position of a known reference point on the tubular at a particular moment in time together with the rotational speed of the tubular at such moment, the data processor further configured to process (1) at least some of the external diameter samples in association with the rotational information in order to map external diameter variation data over a corresponding, portion of the external cylindrical surface of the tubular, and (2) at least some of the plurality of thermal images in association with the rotational information in order to map surface thermography data over a corresponding portion of the external cylindrical surface of the tubular.

16. The Data Acquisition System of claim 15, in which the data processor is further configured to process at least some of the laser samples in association with selected ones of the thermal images in order to enhance the surface thermography data with corresponding tubular external surface contour variation data.

17. The Data Acquisition System of claim 15,
in which the data processor is further configured to process at least some of the external diameter samples in association with selected ones of the thermal images in order to enhance the surface thermography data, with corresponding external diameter variation data.

18. The Data Acquisition System of claim 15, in which the thermal imaging camera generates thermal images from portions of the external cylindrical surface of the tubular whose surface temperature is above ambient.

19. The Data Acquisition System of claim 15 in which the data processor processes the surface thermography data in real time.

* * * * *